US008914115B2

(12) United States Patent
Giftakis et al.

(10) Patent No.: US 8,914,115 B2
(45) Date of Patent: Dec. 16, 2014

(54) SELECTING THERAPY CYCLE PARAMETERS BASED ON MONITORED BRAIN SIGNAL

(75) Inventors: Jonathon E. Giftakis, Maple Grove, MN (US); Paul H. Stypulkowski, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 292 days.

(21) Appl. No.: 12/843,665

(22) Filed: Jul. 26, 2010

(65) Prior Publication Data

US 2011/0137371 A1    Jun. 9, 2011

Related U.S. Application Data

(60) Provisional application No. 61/266,424, filed on Dec. 3, 2009.

(51) Int. Cl.
*A61N 1/18* (2006.01)

(52) U.S. Cl.
USPC .......................................................... 607/45

(58) Field of Classification Search
USPC .......................................................... 607/45
See application file for complete search history.

(56) References Cited

U.S. PATENT DOCUMENTS

| | | | |
|---|---|---|---|
| 5,978,702 | A | 11/1999 | Ward et al. |
| 6,066,163 | A | 5/2000 | John |
| 6,263,237 | B1 | 7/2001 | Rise |
| 6,463,328 | B1 | 10/2002 | John |
| 6,622,036 | B1 | 9/2003 | Suffin |
| 6,671,555 | B2 | 12/2003 | Gielen et al. |
| 6,708,064 | B2 | 3/2004 | Rezai |
| 7,006,872 | B2 | 2/2006 | Gielen et al. |
| 7,024,247 | B2 | 4/2006 | Gliner et al. |
| 7,231,245 | B2 | 6/2007 | Greenwald et al. |
| 7,242,983 | B2 | 7/2007 | Frei et al. |
| 7,277,758 | B2 | 10/2007 | DiLorenzo |
| 7,353,064 | B2 | 4/2008 | Gliner et al. |

(Continued)

FOREIGN PATENT DOCUMENTS

| | | |
|---|---|---|
| WO | 01/76469 A2 | 10/2001 |
| WO | WO 2008/013722 | 1/2008 |
| WO | WO 2009/129486 | 10/2009 |

OTHER PUBLICATIONS

Erwin B. Montgomery, Jr., M.D, "Deep Brain Stimulation Programming," Feb. 20, 2006, 37 pages.

(Continued)

*Primary Examiner* — Paula J Stice
(74) *Attorney, Agent, or Firm* — Shumaker & Sieffert, P.A.

(57) ABSTRACT

Bioelectrical brain signals may be monitored at one more regions of the brain of a patient by a medical device. The monitored bioelectrical signals may be used to select one or more therapy cycle parameters, e.g., on cycle duration and/or off cycle duration, for therapy delivered to treat a patient disorder. In one example, the off cycle duration of a therapy may be selected based on the washout period determined from sensed brain signals of the patient following delivery of therapy during an on cycle. In another example, the on cycle duration and/or off cycle duration of a therapy may be selected to maintain the value of one or more characteristics of a brain signal (e.g., cortical activity) of patient within a threshold range of a target value defined for the characteristic that is associated with effective treatment of the patient disorder.

36 Claims, 23 Drawing Sheets

(56) References Cited

U.S. PATENT DOCUMENTS

| | | | |
|---|---|---|---|
| 7,353,065 | B2 | 4/2008 | Morrell |
| 7,418,290 | B2 | 8/2008 | Devlin et al. |
| 7,532,935 | B2 | 5/2009 | Maschino et al. |
| 7,623,927 | B2 | 11/2009 | Rezai |
| 8,027,730 | B2 | 9/2011 | John et al. |
| 2001/0031993 | A1 | 10/2001 | Salo et al. |
| 2002/0013612 | A1 | 1/2002 | Whitehurst |
| 2002/0151939 | A1 | 10/2002 | Rezai |
| 2003/0083724 | A1 | 5/2003 | Jog et al. |
| 2003/0181954 | A1 | 9/2003 | Rezai |
| 2004/0093983 | A1 | 5/2004 | Mishima et al. |
| 2004/0111127 | A1 | 6/2004 | Gliner |
| 2004/0172091 | A1 | 9/2004 | Rezai |
| 2005/0010262 | A1 | 1/2005 | Rezai et al. |
| 2005/0043774 | A1 | 2/2005 | Devlin et al. |
| 2005/0081847 | A1 | 4/2005 | Lee et al. |
| 2005/0216064 | A1 | 9/2005 | Heruth et al. |
| 2005/0216071 | A1 | 9/2005 | Devlin et al. |
| 2006/0058627 | A1 | 3/2006 | Flaherty et al. |
| 2006/0116742 | A1 | 6/2006 | De Ridder |
| 2006/0217781 | A1 | 9/2006 | John et al. |
| 2006/0259099 | A1 | 11/2006 | Goetz et al. |
| 2006/0264957 | A1 | 11/2006 | Cragg et al. |
| 2007/0027499 | A1 | 2/2007 | Maschino et al. |
| 2007/0027500 | A1 | 2/2007 | Maschino et al. |
| 2007/0028212 | A1 | 2/2007 | Meijer et al. |
| 2007/0060973 | A1* | 3/2007 | Ludvig et al. ............ 607/45 |
| 2007/0067001 | A1 | 3/2007 | Lozano et al. |
| 2007/0100392 | A1* | 5/2007 | Maschino et al. ......... 607/45 |
| 2007/0123758 | A1 | 5/2007 | Miesel et al. |
| 2007/0129769 | A1 | 6/2007 | Bourget et al. |
| 2007/0142874 | A1 | 6/2007 | John |
| 2007/0150024 | A1 | 6/2007 | Leyde et al. |
| 2007/0161919 | A1 | 7/2007 | DiLorenzo |
| 2007/0167991 | A1 | 7/2007 | DiLorenzo |
| 2007/0173901 | A1 | 7/2007 | Reeve |
| 2007/0208212 | A1 | 9/2007 | DiLorenzo |
| 2007/0213785 | A1* | 9/2007 | Osorio et al. ............ 607/45 |
| 2007/0213786 | A1 | 9/2007 | Sackellares et al. |
| 2007/0265489 | A1 | 11/2007 | Fowler et al. |
| 2007/0265536 | A1 | 11/2007 | Giftakis et al. |
| 2007/0293901 | A1 | 12/2007 | Rousso et al. |
| 2008/0004660 | A1 | 1/2008 | Assaf et al. |
| 2008/0033502 | A1 | 2/2008 | Harris et al. |
| 2008/0046036 | A1 | 2/2008 | King et al. |
| 2008/0058874 | A1 | 3/2008 | Westlund et al. |
| 2008/0154332 | A1 | 6/2008 | Rezai |
| 2008/0183097 | A1 | 7/2008 | Leyde et al. |
| 2008/0188906 | A1 | 8/2008 | Barolat et al. |
| 2008/0249431 | A1 | 10/2008 | Bier et al. |
| 2008/0255632 | A1 | 10/2008 | Rezai |
| 2008/0269631 | A1 | 10/2008 | Denison et al. |
| 2009/0082641 | A1 | 3/2009 | Giftakis et al. |
| 2009/0099627 | A1 | 4/2009 | Molnar et al. |
| 2009/0264957 | A1 | 10/2009 | Giftakis et al. |
| 2009/0264967 | A1 | 10/2009 | Giftakis et al. |
| 2010/0114237 | A1 | 5/2010 | Giftakis et al. |
| 2010/0121213 | A1 | 5/2010 | Giftakis et al. |
| 2010/0121214 | A1 | 5/2010 | Giftakis et al. |
| 2010/0228310 | A1 | 9/2010 | Shuros et al. |
| 2010/0256707 | A1 | 10/2010 | Ridder et al. |
| 2010/0324628 | A1 | 12/2010 | Westlund et al. |
| 2011/0307030 | A1 | 12/2011 | John |

OTHER PUBLICATIONS

Wright et al., "Cortical excitability predicts seizures in acutely drug-reduced temporal lobe epilepsy patients," Neurology, 2006;67:1646-1651.

U.S. Appl. No. 61/266,424, filed Dec. 3, 2009 entitled "Selecting Therapy Cycle Parameters Based on Monitored Brain Signal,".

International Search Report and Written Opinion dated Mar. 21, 2011 for corresponding PCT Application No. PCT/US2010/058688, 14 pages.

* cited by examiner

176 ⟶

| THERAPY PROGRAM (170) | CORTICAL ACTIVITY SUPPRESSION (172) | WASHOUT PERIOD DURATION (174) | SELECTED ON CYCLE/ OFF CYCLE (178) | POWER USAGE RATING (180) |
|---|---|---|---|---|
| PROGRAM A | 50% | 10 MIN | 1 MIN/5 MIN | 6 |
| PROGRAM B | 60% | 16 MIN | 1 MIN/8 MIN | 8 |
| PROGRAM C | 80% | 20 MIN | 45 SEC/12MIN | 9 |
| • | • | • | • | • |
| • | • | • | • | • |
| • | • | • | • | • |
| • | • | • | • | • |
| PROGRAM N | 60% | 12 MIN | 2 MIN/6 MIN | 5 |

FIG. 24

SELECTING THERAPY CYCLE PARAMETERS BASED ON MONITORED BRAIN SIGNAL

This application claims the benefit of U.S. Provisional Application No. 61/266,424 by Giftakis et al., entitled, "SELECTING THERAPY CYCLE PARAMETERS BASED ON MONITORED BRAIN SIGNAL" and filed on Dec. 3, 2009, the entire content of which is incorporated herein by reference.

TECHNICAL FIELD

The disclosure relates to medical devices and, more particularly, to selection of therapy parameters for a medical device.

BACKGROUND

Implantable medical devices, such as electrical stimulators or therapeutic agent delivery devices, may be used in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agent, insulin, pain relieving agent or anti-inflammatory agent to a target tissue site within a patient. A medical device may be used to deliver therapy to a patient to treat a variety of symptoms or patient conditions such as chronic pain, tremor, Parkinson's disease, other types of movement disorders, seizure disorders (e.g., epilepsy), urinary or fecal incontinence, sexual dysfunction, obesity, mood disorders, gastroparesis or diabetes. In some therapy systems, an implantable electrical stimulator delivers electrical therapy to a target tissue site within a patient with the aid of one or more electrodes, which may be deployed by medical leads. In addition to or instead of electrical stimulation therapy, a medical device may deliver a therapeutic agent to a target tissue site within a patient with the aid of one or more fluid delivery elements, such as a catheter or a therapeutic agent eluting patch.

During a programming session, which may occur during implant of the medical device, during a trial session, or during a follow-up session after the medical device is implanted in the patient, a clinician may generate one or more therapy programs that provide efficacious therapy to the patient, where each therapy program may define values for a set of therapy parameters. A medical device may deliver therapy to a patient according to one or more stored therapy programs. In the case of electrical stimulation, the therapy parameters may define characteristics of the electrical stimulation waveform to be delivered. Where electrical stimulation is delivered in the form of electrical pulses, for example, the parameters may include an electrode combination, an amplitude, which may be a current or voltage amplitude, a pulse width, and a pulse rate for the pulses. The therapy parameters may also define one or more therapy timing parameters. For example, for cycled therapy, the therapy parameters may include one or more therapy cycle parameters, such as, e.g., on cycle duration and off cycle duration. In the case of a therapeutic agent delivery device, the therapy parameters may include a dose (e.g., a bolus or a group of boluses) size, a frequency of bolus delivery, a concentration of a therapeutic agent in the bolus, a type of therapeutic agent to be delivered to the patient (if the medical device is configured to deliver more than one type of agent), a lock-out interval, and so forth.

SUMMARY

In general, the disclosure relates to systems, devices, and methods for controlling delivery of therapy to a patient based on one or more monitored bioelectrical brain signals of the brain of a patient. The therapy may be delivered to the patient via a medical device to treat a patient disorder. The bioelectrical brain signals (also referred to herein as brain signals) may be indicators of the brain state of a patient. In some examples, at least one parameter of a therapy cycle (e.g., off cycle duration and/or on cycle duration) is selected based on the brain state of a patient determined based on the sensed brain signals.

In some examples, the at least one therapy cycle parameter is selected to maintain a target brain state of the patient, while also minimizing the power usage of the therapy delivered to the patient. In some examples, the at least one therapy cycle parameter is selected based on the washout period characteristic (e.g., duration) for a particular set of therapy parameters, where the washout period characteristic is determined based on the sensed brain signal. The therapy cycle parameters may be selected during a programming session during which one or more therapy program are defined for delivery of chronic therapy to the patient from a medical device. In some examples, therapy cycle parameters may be adjusted, e.g., automatically or semi-automatically, by a medical device based on the behavior of a brain signal sensed during therapy.

In one example, the disclosure is directed to a method comprising monitoring a brain signal of a patient, selecting at least one parameter of a therapy cycle on the monitored brain signal of the patient, wherein the at least one parameter of the therapy cycle includes at least one of an on cycle duration or an off cycle duration, and controlling delivery of the therapy to the patient according to the at least one selected parameter of the therapy cycle.

In another example, the disclosure is directed to a system comprising a sensing module configured to monitor a brain signal of a patient, a therapy module configured to deliver therapy to the patient, and a processor configured to select at least one parameter of a therapy cycle based on the monitored brain signal of the patient and control the therapy module to deliver the therapy to the patient according to the at least one selected parameter of the therapy cycle, wherein the at least one parameter of the therapy cycle includes at least one of an on cycle duration or an off cycle duration.

In another example, the disclosure is directed to a system comprising means for monitoring a brain signal of a patient, means for selecting at least one parameter of a therapy cycle on the monitored brain signal of the patient, and means for controlling delivery of the therapy to the patient according to the at least one selected parameter of the therapy cycle, wherein the at least one parameter of the therapy cycle includes at least one of an on cycle duration or an off cycle duration.

In another example, the disclosure is directed to a computer-readable storage medium comprising instructions that cause a programmable processor to monitor a brain signal of a patient, select at least one parameter of a therapy cycle on the monitored brain signal of the patient, and control delivery of the therapy to the patient according to the at least one selected parameter of the therapy cycle, wherein the at least one parameter of the therapy cycle includes at least one of an on cycle duration or an off cycle duration.

In another aspect, the disclosure is directed to a computer-readable storage medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein. The computer-readable storage medium may be an article of manufacture, and may be non-transitory.

The details of one or more examples of the disclosure are set forth in the accompanying drawings and the description below. Other features, objects, and advantages will be apparent from the description and drawings, and from the claims.

BRIEF DESCRIPTION OF DRAWINGS

FIG. 24 is a table illustrating example metrics associated with an example therapy system.

DETAILED DESCRIPTION

Figure 1:
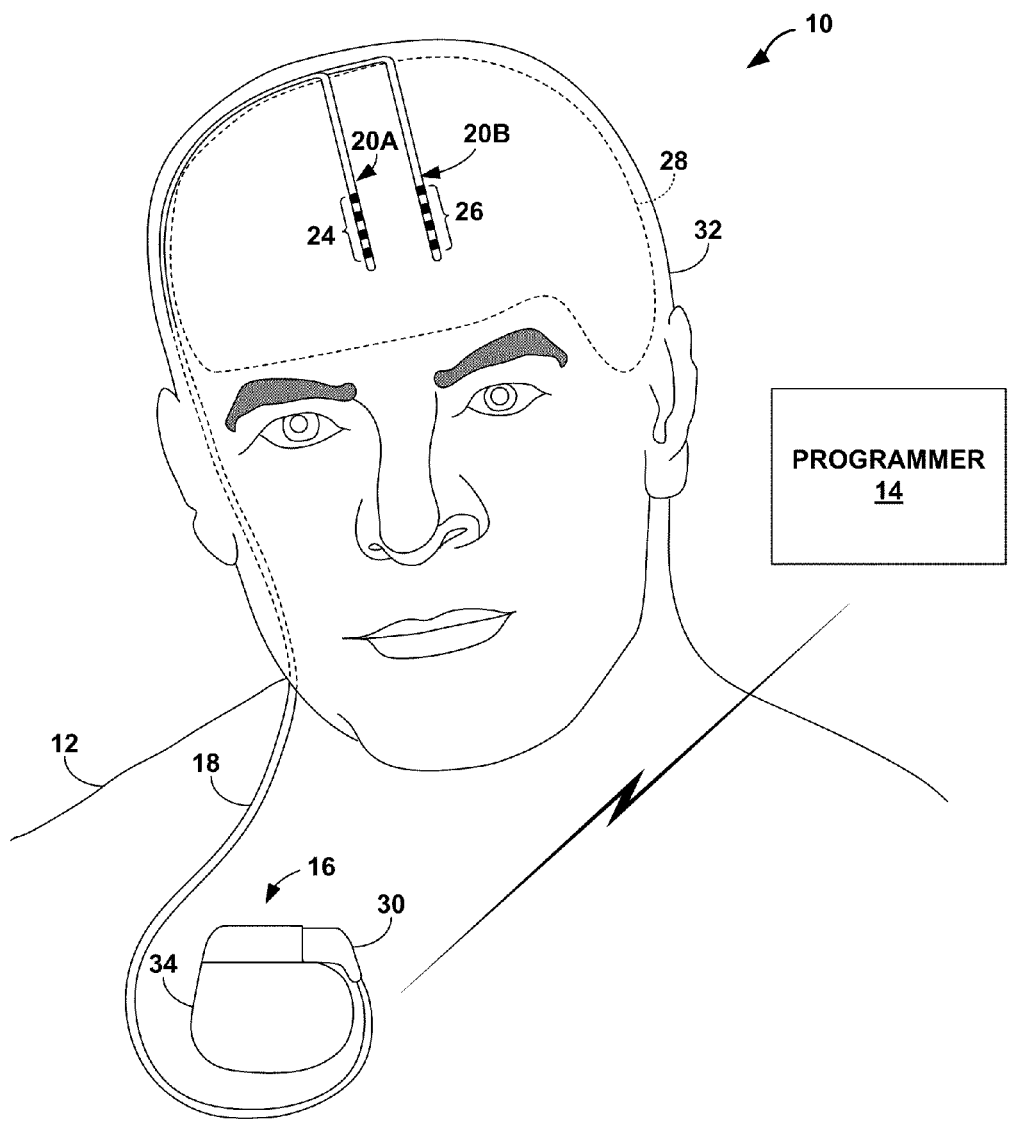
FIG. 1 is a conceptual diagram illustrating an example deep brain stimulation (DBS) system for delivery of an example electrical stimulation therapy to a tissue site within a brain of a patient.

FIG. 1 is a conceptual diagram illustrating an example therapy system 10 that delivers therapy to patient 12 to manage a disorder of patient 12. In some examples, therapy system 10 may deliver therapy to patient 12 to manage a seizure disorder (e.g., epilepsy) of patient 12 that is characterized by the occurrence of seizures. Therapy system 10 may be used to manage the seizure disorder of patient 12 by preventing the onset of seizures, minimizing the severity of seizures, shortening the duration of seizures, minimizing the frequency of seizures, and the like. Patient 12 ordinarily will be a human patient. In some cases, however, therapy system 10 may be applied to other mammalian or non-mammalian non-human patients. While examples of the disclosure are described in some cases with regard to management of seizure disorders, in other examples, therapy system 10 may also provide therapy to manage symptoms of other patient conditions, such as, but not limited to, psychological disorders, mood disorders, movement disorders or other neurogenerative impairment. In one example, therapy system 10 may provide therapy to patient 12 to manage Alzheimer's disease.

Therapy system 10 includes medical device programmer 14, implantable medical device (IMD) 16, lead extension 18, and one or more leads 20A and 20B (collectively "leads 20) with respective sets of electrodes 24, 26. IMD 16 includes a therapy module that includes a stimulation generator that generates and delivers electrical stimulation therapy to one or more regions of brain 28 of patient 12 via a subset of electrodes 24, 26 of leads 20A and 20B, respectively. In the example shown in FIG. 1, therapy system 10 may be referred to a deep brain stimulation (DBS) system because IMD 16 provides electrical stimulation therapy directly tissue within brain 28, e.g., a tissue site under the dura mater of brain 28. In other examples, leads 20 may be positioned to deliver therapy to a surface of brain 28 (e.g., the cortical surface of brain 28). In some examples, delivery of stimulation to one or more regions of brain 28, such as an anterior nucleus, thalamus or cortex of brain 28, provides an effective treatment to manage a disorder of patient 12. In some examples, IMD 16 may provide cortical stimulation therapy to patient 12, e.g., by delivering electrical stimulation to one or more tissue sites in the cortex of brain 28. In some examples, IMD 16 may provide vagal nerve stimulation (VNS) therapy to patient 12 by delivering electrical stimulation to one or more vagal nerve tissue sites.

In the example shown in FIG. 1, IMD 16 may be implanted within a subcutaneous pocket above the clavicle of patient 12.

In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. Generally, IMD 16 is constructed of a biocompatible material that resists corrosion and degradation from bodily fluids. IMD 16 may comprise a hermetic housing 34 to substantially enclose components, such as a processor, therapy module, and memory.

Leads 20 are implanted within the right and left hemispheres, respectively, of brain 28 in order deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. Different neurological or psychiatric disorders may be associated with activity in one or more of regions of brain 28, which may differ between patients. For example, in the case of major depressive disorder (MDD), bipolar disorder, obsessive compulsive disorder (OCD) or other anxiety disorders, leads 20 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, or any combination thereof. Target tissue sites not located in brain 28 of patient 12 are also contemplated.

As another example, in the case of a seizure disorder or Alzheimer's disease, for example, leads 20 may be implanted to deliver electrical stimulation to regions within the Circuit of Papez, such as, e.g., the anterior thalamic nucleus, the internal capsule, the cingulate, the formix, the mammillary bodies, the mammillothalamic tract (mammillothalamic fasciculus), and/or hippocampus. As will be described in further detail below, in some examples, IMD 16 may deliver therapy to the anterior thalamic nucleus, hippocampus, or other suitable brain region to control a brain state of patient 12 (e.g., as indicated by bioelectrical brain signals sensed within the Circuit of Papez) in a manner that effectively treats a disorder of patient 12. For example, in the case of a seizure disorder, IMD 16 may deliver therapy to a region of brain 28 via a selected subset of electrodes 24, 26 to suppress cortical activity within the anterior thalamic nucleus, hippocampus, or other brain region associated with the occurrence of seizures (e.g., a seizure focus of brain 28). Conversely, in the case of Alzheimer's disease, IMD 16 may deliver therapy to a region of brain 28 via electrodes 24, 26 to increase cortical activity within the anterior thalamic nucleus, hippocampus, or other brain region associated with Alzheimer's disease. As another example, in the case of depression (e.g., MDD), IMD 16 may deliver therapy to a region of brain 28 via electrodes 24, 26 to increase cortical activity within one or more regions of brain 28 to effective treat the patient disorder. As another example, IMD 16 may deliver therapy to a region of brain 28 via electrodes 24, 26 to decrease cortical activity within one or more regions of brain 28, such as, e.g., the frontal cortex, to treat the disorder.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

Leads 20 may deliver electrical stimulation to treat any number of neurological disorders or diseases in addition to seizure disorders, such as movement disorders or psychiatric disorders. Examples of movement disorders include a reduction in muscle control, motion impairment or other movement problems, such as rigidity, bradykinesia, rhythmic hyperkinesia, nonrhythmic hyperkinesia, dystonia, tremor, and akinesia. Movement disorders may be associated with patient disease states, such as Parkinson's disease or Huntington's disease. Examples of psychiatric disorders include MDD, bipolar disorder, anxiety disorders, post traumatic stress disorder, dysthymic disorder, and OCD. As described above, examples of the disclosure are primarily described with regard to treating a seizure disorder (e.g., epilepsy). Treatment of other patient disorders via delivery of therapy to brain 28 is contemplated.

Leads 20 may be implanted within a desired location of brain 28 via any suitable technique, such as through respective burr holes in a skull of patient 12 or through a common burr hole in the cranium 32. Leads 20 may be placed at any location within brain 28 such that electrodes 24, 26 of leads 20 are capable of providing electrical stimulation to targeted tissue during treatment. Electrical stimulation generated from the stimulation generator (not shown) within the therapy module of IMD 16 may help prevent the onset of events associated with the patient's disorder or mitigate symptoms of the disorder. For example, electrical stimulation therapy delivered by IMD 16 to a target tissue site within brain 28 may help minimize the occurrence of seizures or minimize the duration, severity or frequency of seizures if patient 12 has a seizure disorder by helping patient 12 maintain a brain state (e.g., as characterized by the bioelectrical activity within a region of brain 28) in which the likelihood of a seizure is reduced from that of a baseline brain state of patient 12 or a brain state in which a relatively severe seizure is not likely. A relatively severe seizure, e.g., a tonic-clonic seizure, may be characterized by changes in muscle tone and involuntary movements, or by a particular duration of time in which the symptoms of a seizure are observed, a loss of consciousness, or other parameters.

The exact therapy parameter values of the stimulation therapy that helps prevent or mitigate seizures, such as the amplitude or magnitude of the stimulation signals, the duration of each signal, the waveform of the stimuli (e.g., rectangular, sinusoidal or ramped signals), the frequency of the signals, and the like, may be specific for the particular target stimulation site (e.g., the region of the brain) involved as well as the particular patient and patient condition.

In the examples shown in FIG. 1, electrodes 24, 26 of leads 20 are shown as ring electrodes. Ring electrodes may be relatively easy to program and are typically capable of delivering an electrical field to any tissue adjacent to leads 20. In other examples, electrodes 24, 26 of leads 20 may have different configurations. For example, electrodes 24, 26 of leads 20 may have a complex electrode array geometry that is capable of producing shaped electrical fields. The complex electrode array geometry may include multiple electrodes (e.g., partial ring or segmented electrodes) around the perimeter of each lead 20, rather than a ring electrode. In this manner, electrical stimulation may be directed to a specific direction from leads 20 to enhance therapy efficacy and reduce possible adverse side effects from stimulating a large volume of tissue. In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In alternative examples, leads 20 may have shapes other than elongated cylinders as shown in FIG. 1. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs. A therapy program may define one or more electrical stimulation parameter values for therapy generated and delivered from IMD 16 to brain 28 of patient 12. Where IMD 16 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities.

In addition, where IMD 16 delivers electrical stimulation pulses in cycles rather than on a substantially continuous basis whereby stimulation is constantly delivered to patient 12, a therapy may be characterized by one or more therapy cycle parameters that are selected for delivery of the electrical stimulation to patient 12 from IMD 16 via electrodes 24, 26. A therapy cycle defines the timing with which stimulation signals defined by a set of stimulation parameters (e.g., voltage or current amplitude, frequency, and/or electrode combination) are delivered. Therefore, the therapy cycle differs from the stimulation parameters with which IMD 16 generates stimulation signals. Example therapy cycle parameters for a therapy may include on cycle duration and an off cycle duration. In such examples, when IMD 16 is activated for delivery of therapy to patient 12, IMD 16 may alternately deliver electrical stimulation to one or more tissue sites of brain via a selected subset of electrodes 24 and/or 26 during an on cycle and temporarily suspend delivery of the electrical stimulation to the one or more tissue sites during an off cycle. During the off cycle, minimal to no therapy is delivered to patient 12. The effectiveness (e.g., the mitigation of patient symptoms, the prevention or minimization of the occurrence of seizures, the duration in which the effects of the stimulation therapy persist, and the like) of the therapy provided by system 10 in managing the disorder of patient 12 may depend on the electrical stimulation parameters, as well as the cycle timing parameters of the therapy.

In addition to delivering therapy to manage a disorder of patient 12, therapy system 10 monitors one or more bioelectrical brain signals of patient 12. For example, IMD 16 may include a sensing module that senses bioelectrical brain signals within one or more regions of brain 28. In the example shown in FIG. 1, the signals generated by electrodes 24, 26 are conducted to the sensing module within IMD 16 via conductors within the respective lead 20A, 20B. As described in further detail below, in some examples, a processor of IMD 16 or another device (e.g., programmer 14) monitors the bioelectrical signals within brain 28 of patient 12 and controls delivery of electrical stimulation therapy to brain 28 via a selected subset of electrodes 24, 26 according to one or more therapy cycle parameters selected based on the monitored bioelectrical brain signals to provide therapy to patient 12 in manner that effectively treats a patient condition (e.g., a seizure disorder) of patient 12.

In some examples, the sensing module of IMD 16 may receive the bioelectrical signals from electrodes 24, 26 or other electrodes positioned to monitored brain signals of patient 12. Electrodes 24, 26 may also be used to deliver electrical stimulation from the therapy module to target sites within brain 28 as well as sense brain signals within brain 28. However, IMD 16 can also use separate sensing electrodes to sense the bioelectrical brain signals. In some examples, the sensing module of IMD 16 may sense bioelectrical brain signals via one or more of the electrodes 24, 26 that are also used to deliver electrical stimulation to brain 28. In other examples, one or more of electrodes 24, 26 may be used to sense bioelectrical brain signals while one or more different electrodes 24, 26 may be used to deliver electrical stimulation.

Depending on the particular stimulation electrodes and sense electrodes used by IMD 16, IMD 16 may monitor brain signals and deliver electrical stimulation at the same region of brain 28 or at different regions of brain 28. In some examples, the electrodes used to sense bioelectrical brain signals may be located on the same lead used to deliver electrical stimulation, while in other examples, the electrodes used to sense bioelectrical brain signals may be located on a different lead than the electrodes used to deliver electrical stimulation. In some examples, a brain signal of patient 12 may be monitored with external electrodes, e.g., scalp electrodes. Moreover, in some examples, the sensing module that senses bioelectrical brain signals of brain 28 (e.g., the sensing module that generates an electrical signal indicative of the activity within brain 28) is in a physically separate housing from outer housing 34 of IMD 16. However, in the example shown in FIG. 1 and the example primarily referred to herein for ease of description, the sensing module and therapy module of IMD 16 are enclosed within a common outer housing 34.

The bioelectrical brain signals monitored by IMD 16 may reflect changes in electrical current produced by the sum of electrical potential differences across brain tissue. Examples of the monitored bioelectrical brain signals include, but are not limited to, an electroencephalogram (EEG) signal, an electrocorticogram (ECoG) signal, a local field potential (LFP) sensed from within one or more regions of a patient's brain and/or action potentials from single cells within the patient's brain. As will be described in further detail below, therapy system 10 may control delivery of therapy to brain 28 of patient 12 based on the monitored brains signals of patient 12. The monitored brain signals of a patient may be used to characterize the brain state of patient 12. Example characteristics of the brain signals which may characterize the brain state of a patient may include, for example, time domain characteristics (e.g., an amplitude) or a frequency domain characteristic (e.g., an energy level in one or more frequency bands) of the brain signals sensed by IMD 16 within all or specific regions of brain 28 of patient 12. For example, the characteristic of the brain signals may be an absolute amplitude value or a root mean square amplitude value. In addition, the amplitude value may comprise an average, peak, mean or instantaneous amplitude value over a period of time or a maximum amplitude or an amplitude in a particular percentile of the maximum (e.g., an amplitude value that represents 95% of the maximum amplitude value). In some examples, cortical activity derived from the sensed brain signal of patient 12 may be used to characterize the brain state of patient 12.

In some examples, a patient's brain state may be characterized by assessment of brain signals evoked by stimulation. A number of techniques that include analysis of brain signals evoked by stimulation can be used. For example, the paper authored by Wright et al., entitled "Cortical excitability predicts seizures in acutely drug-reduced temporal lobe epilepsy patients," (Neurology 2006; 67: 1646-1651) describes the use of paired pulse transcranial magnetic stimulation (TMS) to produced motor evoked potentials (MEPs) in the neuromuscular system of a patient. By varying the time interval between the two TMS pulses, and by comparing the magnitudes of the MEPs, Wright indicates that changes in cortical excitability may be inferred. The changes in cortical excitability were found to correlate with the likelihood of seizure occurrence.

In a similar fashion, in some examples, one or more characteristics of the sensed evoked brain signals used to predict the likelihood of an event may be used to characterize the brain state of a patient. U.S. Pat. Nos. 6,671,555 and 7,006,872 to Gielen et al., entitled "CLOSED LOOP NEUROMODULATION FOR SUPPRESSION OF EPILEPTIC ACTIVITY," and filed on Apr. 27, 2001 and Mar. 13, 2003, respectively, the entire content of both of which is incorporated herein by reference, describe methods for predicting the likelihood of occurrence of an impending neurological episode, e.g., by analyzing response field potentials evoked by stimuli delivered to a structure of the brain. In some examples, a system may be configured to deliver pairs of electric stimuli to the brain of a patient, measure the evoked response field potentials to each stimulus, and compare the response to the first stimulus to the response to the second stimulus. The time interval between the stimuli can be varied, and based upon the comparison of the two responses the likelihood of an event, such as, e.g., an epileptic event, can be predicted. In a similar fashion, one or more characteristics of the sensed evoked brain signals used to predict the likelihood of an event may be used to characterize the brain state of a patient. Other example methodologies for characterizing the brain state of a patient are contemplated.

Specific brain states within brain 28 of patient 12 may be identified as desirable or undesirable with regard to the disorder of patient 12. The brain state may indicate, for example, the possibility of the onset of one or more symptoms of the patient condition. For example, for seizure disorder, a brain state may be characterized by the level of cortical activity within, for example, the hippocampus, which is associated with a high risk of the occurrence of a seizure event (e.g., the onset of seizure or the onset of a specific type of seizure, such as a seizure associated with a motor component). The level of cortical activity within brain 28 can be indicated by, for example, an amplitude of a bioelectrical brain signal, the variance of the bioelectrical brain signal over time, or a frequency domain characteristic (e.g., an energy level within one or more specific frequency bands) of the bioelectrical brain signal. As another example, for Alzheimer's disease, a brain state may be characterized by the level of cortical activity within, for example, the hippocampus, which is associated with memory loss. In each case, such brain states may be considered undesirable brain states, and the therapy delivered by IMD 16 to brain 28 may be configured change the level of cortical activity from an undesired level to a desired level.

IMD 16 may deliver therapy to the brain 28 in a manner that influences the brain signals within one or more regions of brain 28. IMD 16 delivers therapy to brain 28 via a selected subset of electrodes 24, 26 to change one or more characteristics of a brain signal exhibited in one or more regions of brain 28 that is associated with an undesired baseline brain state (e.g., a baseline brain state exhibited by patient 12 in the absence of therapy) to characteristics associated with a desired brain state. In a desired brain state, the bioelectrical brain signals sensed via the sensing module of IMD 16 may be indicative of a patient state in which the patient condition is treated, e.g., one or more of symptoms of the patient disorder or mitigated or even eliminated. Once brain 28 exhibits the desired brain state, IMD 16 can sense brain signals of patient 12 to monitor the brain state of patient 12 and control therapy delivery to brain 28 to maintain maintains the desirable brain state, e.g., rather than returning to an undesired brain state. In other examples, IMD 16 controls therapy delivery to brain 28 upon determining that the patient's brain state has changed from the desirable brain state. In these examples, the brain state of patient 12 as indicated by bioelectrical brain signals can be used to control therapy delivery to patient 12 in a pseudo-closed loop manner.

As described above, in some examples, IMD 16 may deliver therapy to brain 28 of patient 12 according to a cycle including alternating on cycles and off cycles. In the case of electrical stimulation pulses, during an on cycle, the therapy module of IMD 16 actively generates and delivers stimulation pulses to brain 28 via a selected subset of electrodes 24, 26. The electrical stimulation delivered during the on cycle may be characterized by stimulation parameters, e.g., pulse rate, pulse width, pulse amplitude, electrode combination, and the like, which may be defined by a therapy program. During the off cycle following the on cycle, IMD 16 may temporally suspend delivery to electrical stimulation to brain 28 of patient. IMD 16 may automatically resume delivery of electrical stimulation to brain 28 via electrodes 24, 26 upon expiration of the off cycle during the subsequent on cycle.

Following the delivery of electrical stimulation during an on cycle, the influence that the delivered electrical stimulation has on bioelectrical brain signals may not immediately terminate, but, instead, the effects on the bioelectrical signals from the delivered stimulation may dissipate during what may be referred to as a washout period. In general, a washout period is the period of time following delivery of therapy to patient 12 (e.g., following an on cycle) during which one or more carryover effects from the therapy delivery substantially dissipates. In the case of electrical stimulation therapy, the carryover effect generally refers to a physiological effect from delivery of electrical stimulation signals that persist after termination of the signals. An example physiological effect in the change in one or more characteristics (e.g., amplitude, variance or frequency domain characteristic) of a bioelectrical brain signal resulting from the delivery of stimulation. The end of the washout period associated with a therapy program may be the time at which at least one of the physiological effects resulting from the delivery of electrical stimulation therapy to patient 12 according to the therapy program have substantially dissipated, such that patient 12 returns to a baseline condition. The baseline condition may be, for example, the brain state defined by one or more characteristics of bioelectrical brain signals prior to delivery of therapy according to the therapy program, or prior to the delivery of any therapy to patient 12. In some examples, the baseline brain state of a patient may be considered an undesirable brain state.

One type of characteristic of the washout period may include the duration of the washout period, i.e., the time it takes for a physiological signal to return to a particular brain state, which may be a baseline state. In terms of bioelectrical brain signals, the duration of the washout period may be the time it takes for a bioelectrical brain signal to return to a particular brain state, which may be referred to in some cases as a baseline brain state. The baseline brain state may be based on one or more bioelectrical brain signal characteristics within a region of brain 28 prior to delivery of stimulation according to a particular therapy program or prior to any therapy delivery. As described above, characteristic of the bioelectrical brain signal that may be used to define the baseline brain state (or other brain state) may include a time domain characteristic (e.g., an amplitude) or a frequency domain characteristic (e.g., an energy level in one or more frequency bands) of brain signals monitored by sensing module of IMD 16 using one or more of electrodes 24, 26. In some examples, the level of cortical activity in a brain may be derived from the brain signal and used to define the brain state of patient 12.

As described in further detail below, in some examples, IMD 16 monitors a brain signal of patient 12 within one or more target regions of brain 28 and selects at least one parameter of a therapy cycle based on the monitored brain signal. For example, IMD 16 may monitor a brain signal within a region of interest in brain 28 during an off cycle, following delivery of electrical stimulation to brain 28 via a selected subset of electrodes 24, 26 during an on cycle, to monitor the dissipation of the carryover effects during the washout period. Based on the monitored brain signal and the washout period resulting from the delivery of stimulation during the on cycle, a processor of IMD 16 may select the duration of the off cycle such that delivery of electrical stimulation is resumed prior to the return of patient 12 to a baseline brain state, e.g., prior to the end of the washout period. In some examples, the off cycle duration may be selected such that patient 12 maintains bioelectrical brain signals that are within a threshold degree of a target brain state associated with effective treatment of the patient disorder.

The technique for selecting one or more therapy cycle parameters that is based on a washout period characteristic of therapy delivery may be used during a programming session to select desired or optimized therapy cycle parameters for a particular therapy program. For example, during a programming session, IMD 16 may monitor one or more bioelectrical brain signals within brain 28 via a selected subset of electrode 24, 26 to determine the washout period and carryover effects during an off cycle following delivery of electrical stimulation according to the particular therapy program during one or more on cycles. Based on the characteristics of the brain signal during the washout period, a clinician can select an off cycle duration that is specific to the therapy program and on cycle duration, whereby the off cycle duration is selected such that patient 12 maintains a desired brain state with the specific on cycle and off cycle duration pairing. Because carryover effects and washout period associated with a particular therapy program may depend on the on cycle duration of the therapy, the process for selecting an off cycle duration may be repeated for different on cycle durations. Moreover, this technique can be used to select a preferred on cycle duration for a particular therapy program. In this manner, cycle parameters may be selected for a particular therapy program, which may be used to deliver from IMD 16 to brain 28 to effectively manage a patient disorder by controlling the brain state of patient 12.

Alternatively or additionally, cycle parameters may be automatically or semi-automatically (e.g., initiated and/or authorized by a user) adjusted for a given therapy program by IMD 16 on a dynamic basis, e.g., while IMD 16 provides chronic therapy to patient 12 to treat a patient disorder. For example, when IMD 16 is configured to deliver electrical stimulation therapy to patient 12 according to a particular therapy cycle (e.g., including a pattern of on cycles and off cycles of respective durations), IMD 16 can monitor one or more bioelectrical brain signals of patient 12, e.g., during an off cycle of the therapy, and automatically or semi-automatically adjust the off cycle duration based on the monitored brain signal. IMD 16 may be configured to make adjustments to the cycle parameters during the provision of chronic therapy on a continuous or periodic basis. The patient condition or disorder may progress, regress or otherwise change during the course of therapy delivery by IMD 16. Therefore, dynamically changing the cycle parameters of a therapy cycle can be useful to accommodate any changes in the patient condition that may benefit from different cycle parameters. For epilepsy patients with infrequent seizures, or seizures that cluster at certain time periods, this may result in dynamic off cycles that substantially correspond to the inter-seizure interval, during which time likelihood of seizure occurrence is low.

In some examples, IMD 16 adjusts the off cycle duration by increasing the duration of the off cycle, for example, if, with the current therapy cycle parameters, the subsequent on cycle begins prior to the carryover effects on the brain signal nearing an undesirable brain state. By ending the off cycle and beginning the following on cycle prior to the carryover effects on the brain signal reaching an undesirable brain state, IMD 16 may be unnecessarily resuming delivery of stimulation to patient 12 rather than allowing the carryover effects on the brain signals resulting from delivered stimulation to dissipate to the baseline brain, or within some threshold amount of the baseline brain state, during the off cycle. In such a case, a processor of IMD 16 can increase the duration of the off cycle of the therapy such that the on cycle does not resume until just prior to the carryover effects on the brain signal of patient 12 dissipating and/or the brain signal reaches an undesirable state. In this manner, system 10 may decrease the power consumption of the therapy delivery by IMD 16 to patient 12 while maintaining effective treatment of the patient disorder.

Conversely, in some examples, IMD 16 may monitor the brain signal of patient 12 and adjust the off cycle duration by decreasing the duration of the off cycle, for example, if the subsequent on cycle begins after the carryover effects on the brain signal dissipate and/or the brain signals indicate patient 12 reaches an undesirable brain state prior to the onset of the next therapy on cycle. In such a case, a processor of IMD 16 can decrease the off cycle duration such that the on cycle resumes prior to the carryover effects of the brain signal reaching an undesirable state. In this way, IMD 16 can actively adjust the therapy cycle parameters to continuously maintain a desirable brain state of patient 12.

In some examples, IMD 16 may monitor one or more brain signals of brain 28 during cycled delivery of therapy to patient 12 and adjust one or more cycle parameters to maintain the brain state within one or more regions of brain 28 at a target brain state. The target brain state may be indicated by one or more characteristics of a brain signal associated with a patient state in which one or more symptoms of the patient condition are substantially minimized or even eliminated, or a patient state in which the possibility of the occurrence of a patient event (e.g., an onset of any type of seizure or a particular type of seizure, an onset of a particular patient mood state, and the like) is substantially minimized compared to a baseline patient state in which no therapeutic effects of therapy delivery are observed. In this manner, the target brain state can be indicated by one or more characteristics of a brain signal associated effective treatment of a patient disorder.

During an on cycle, the stimulation delivered to brain 28 of patient 12 may influence brain signals, e.g., by suppressing or increasing cortical activity, to exhibit characteristics consistent with a target brain state. Following the on cycle, IMD 16 may monitor the brain signal(s) and adjust the off cycle duration, if necessary, in a manner that allows patient 12 to maintain the target brain state. For example, IMD 16 may monitor the brain signal(s) of patient 12 during the off cycle and time the delivery of therapy to patient 12 (e.g., resume delivery of stimulation to brain 28) such that therapy is delivered prior to the dissipation of the carryover effects from the previous on cycle or within some threshold thereof (e.g., prior to the point that brain state of the patient is no longer in the target brain state). In some examples, IMD 16 may alternatively or additionally adjust the on cycle duration in a similar fashion to ensure that stimulation is delivered to brain 28 for a duration that drives the brain signals of the patient to a target brain state.

In some examples of the disclosure, one or more therapy cycle parameters may be selected based on specific therapy parameters values, e.g., as defined by a therapy program, and specific patient attributes. Compared to the application of substantially the same therapy cycle parameters to a plurality of patients, examples of the disclosure may allow therapy cycle parameters to be tailored to account for specific patient attributes and specific therapy parameters. In some the examples of the disclosure, the therapy delivered via IMD 16 may not be controlled to respond to detection or prediction of actual seizure events (other patient events), but generally patient brain state that are associated with a higher likelihood of the patient event occurring (or not occurring).

External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 24, 26 on leads 20, the position of leads 20 within brain 28, initial programs defining therapy parameter values, and any other information that may be useful for programming into IMD 16. Programmer 14 may also be capable of completing functional tests (e.g., measuring the impedance of electrodes 24, 26 of leads 20).

The clinician may also store therapy programs within IMD 16 with the aid of programmer 14. During a programming session, the clinician may determine one or more therapy programs that may provide efficacious therapy to patient 12 to address symptoms associated with the seizure disorder (or other patient condition). For example, the clinician may select one or more electrode combinations with which stimulation is delivered to brain 28. During the programming session, patient 12 may provide feedback to the clinician as to the efficacy of the specific program being evaluated or the clinician may evaluate the efficacy based on one or more physiological parameters of patient (e.g., heart rate, respiratory rate or muscle activity). Programmer 14 may assist the clinician in the creation/identification of therapy programs by providing a methodical system for identifying potentially beneficial therapy parameter values. In some examples, programmer 14 may display selected cycle parameters for one or more therapy programs to allow a clinician to evaluate one or more therapy programs based on the cycle parameters. In some examples, the processor of programmer 14 may calculate and display one or more therapy metrics for evaluating and comparing therapy programs available to delivery of therapy from IMD 16 to patient. An example of such a display is illustrated in FIG. 24.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Programmer 14 may also provide an indication to patient 12 when therapy is being delivered, when patient input has triggered a change in therapy or when the power source within programmer 14 or IMD 16 needs to be replaced or recharged. For example, programmer 14 may include an alert LED, may flash a message to patient 12 via a programmer display, generate an audible sound or somatosensory cue to confirm patient input was received, e.g., to indicate a patient state or to manually modify a therapy parameter.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

Figure 2:
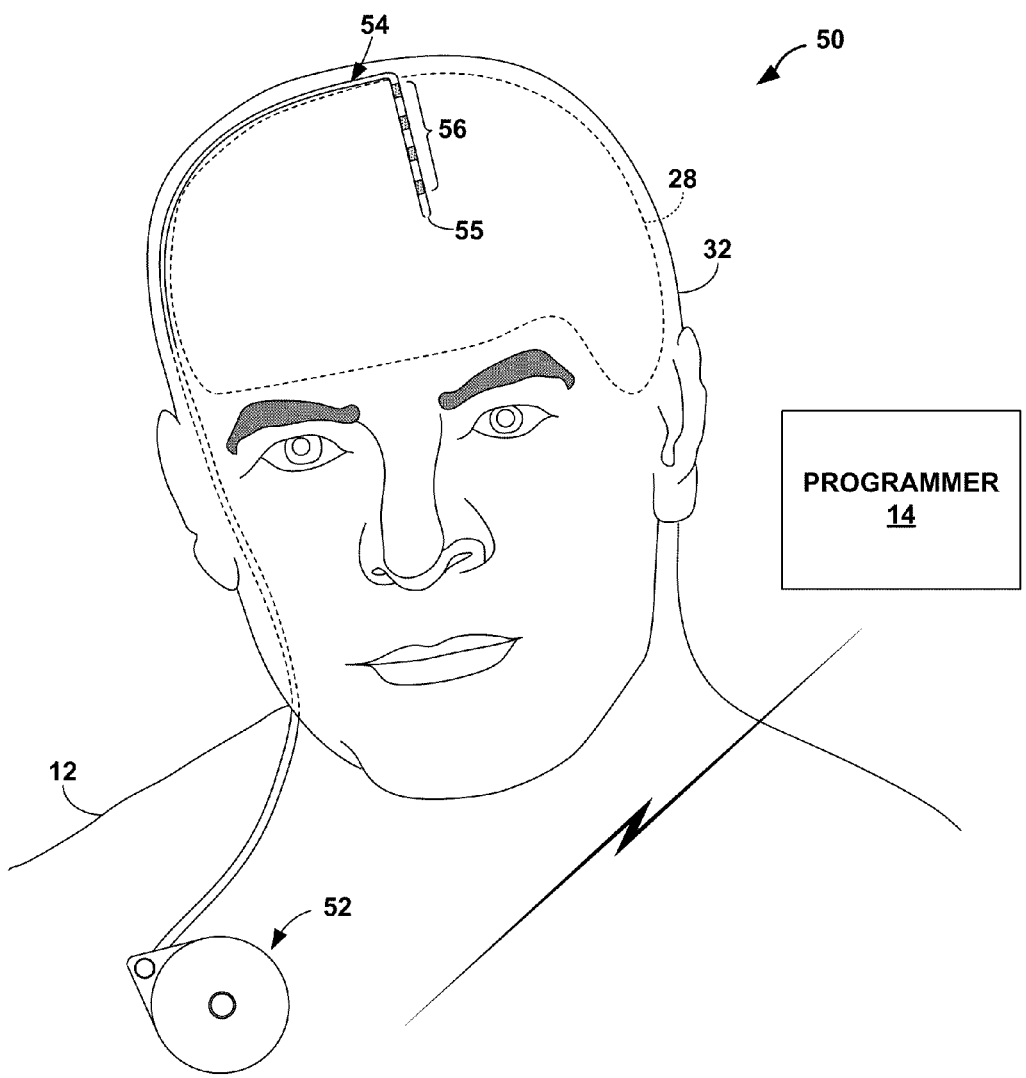
FIG. 2 is a conceptual diagram illustrating an example therapy system for delivery of a therapeutic agent to a tissue site within a brain of a patient.

FIG. 2 is a conceptual diagram illustrating an example therapy system 50 for delivery of a therapeutic agent to a tissue site within brain 28 of a patient 12. Therapy system 50 includes IMD 52 and catheter 54, which includes a plurality of electrodes 56 for sensing one or more bioelectrical brain signals within brain 28 of patient 12. IMD 52 is configured to deliver at least one therapeutic agent, such as a pharmaceutical agent (e.g., anti-seizure medication or Alzheimer's medication), anti-inflammatory agent, gene therapy agent, or the like, to a target tissue site within brain 28 of patient 11 via catheter 54, which is in fluid communication with IMD 52. Catheter 54 may be coupled to IMD 52 either directly or with the aid of an extension (not shown in FIG. 1).

In some examples, IMD 52 includes a fluid pump or another device that delivers a therapeutic agent in some metered or other desired flow dosage to the therapy site within patient 12 from a reservoir within IMD 52 via catheter 54. For treatment of Alzheimer's disease, drug therapy may be intended to slow progression of the disease. The type of drug selected for a particular patient's therapy can be dependent on the stage of progression. For early stages, cholinesterase inhibitors may be delivered to the patient, which include, e.g., donepezil, galantamine, and rivastigmine. For moderate to severe Alzheimer's, memantine may be delivered in isolation, or adjunctive to cholinesterase inhibitors. Examples of pharmaceutical agents that IMD 52 may deliver to patient 12 to manage a patient disorder (e.g., seizure disorder) include, but are not limited to, adenosine, lorazepam, carbamazepine, oxcarbazepine, valproate, divalproex sodium, acetazolamide, diazepam, phenytoin, phenytoin sodium, felbamate, tiagabine, levetiracetam, clonazepam, lamotrigine, primidone, gabapentin, phenobarbital, topiramate, clorazepate, ethosuximide, and zonisamide. Other therapeutic agents may also provide effective therapy to manage the patient's seizure disorder, e.g., by minimizing the severity, duration, and/or frequency of the patient's seizures. In other examples, IMD 52 delivers a therapeutic agent to tissue sites within patient 12 other than brain 28.

Electrodes 56 are configured to sense bioelectrical signals within brain 28 of patient 12 to allow system 50 to monitor one or more bioelectrical brain signals within brain 28. As described above, one or more cycle parameters of a therapy may be selected based on the monitored brain signals of patient 12. Additionally or alternatively, one or more therapy parameters values (e.g., therapeutic delivery rate) defined by a therapy program may be adjusted based on the monitored brains signal. In some examples, electrodes 56 may be substantially similar to one or more of electrodes 24, 26 (FIG. 1). Although FIG. 2 illustrates catheter 54 including four sense electrodes 56, in other examples, a catheter may include any suitable number of sense electrodes, such as one, two, three or greater than four. In addition, although sense electrodes 56 are located proximal to the fluid delivery port 55 of catheter 54 in the example shown in FIG. 2, in other examples, one or more of sense electrodes 56 may be distal to fluid delivery port 55 of catheter 54. Catheter 54 may include more than one fluid delivery port. Thus, in some examples, one or more sense electrodes 56 may be located between fluid delivery ports of catheter 54.

Although the examples of this disclosure are primarily described with regard to the treatment of a patient condition via delivery of electrical stimulation, such examples may be similarly applied to the delivery of a therapeutic agent to a tissue site of patient, e.g., the brain of patient. In one example, for the treatment of a seizure disorder, IMD 52 may deliver a therapeutic agent, such as, e.g., adenosine, to target a seizure focus in brain 28 of patient 12. In cases of cycled therapy delivery, IMD 52 may delivery the therapeutic agent to brain 28 for one or more on cycles, during which time IMD 52 may actively deliver the therapeutic agent to brain 28 substantially continuously or periodically. IMD 52 may monitor the brain signals of the patient 12 via electrodes 56 at various time periods (before, during and/or after) to determine the effects of the delivery of the therapeutic agent to brain 28. In one example, the change (e.g., suppression) in cortical activity of brain 28 due in part to the delivery of the therapeutic agent may be monitored via electrodes 56. Based on the monitored brain signals, one or more therapy cycle parameters of a therapy delivered to patient 12 (e.g., on cycle duration and/or off cycle duration) may be selected, e.g., using one or more the example techniques described in this disclosure. Such a process may be utilized during an initial programming session after implantation of IMD 52. Additionally or alternatively, such therapy cycle parameter selection may occur periodically (e.g., on a daily or weekly basis) at any point during the time period that IMD 52 is used to treat the patient condition via delivery of a therapeutic agent.

In general, while the remainder of the disclosure describes various systems, devices, and techniques for monitoring one or more bioelectrical brain signals of patient 12 and providing therapy to patient 12 based on the monitored brain signals with respect to therapy system 10 of FIG. 1, the systems, devices, and techniques described herein are also applicable to therapy system 50 (FIG. 2), as well as any other therapy system that may include one or more electrodes for sensing bioelectrical brain signals within brain 28 of patient 12.

Figure 3:
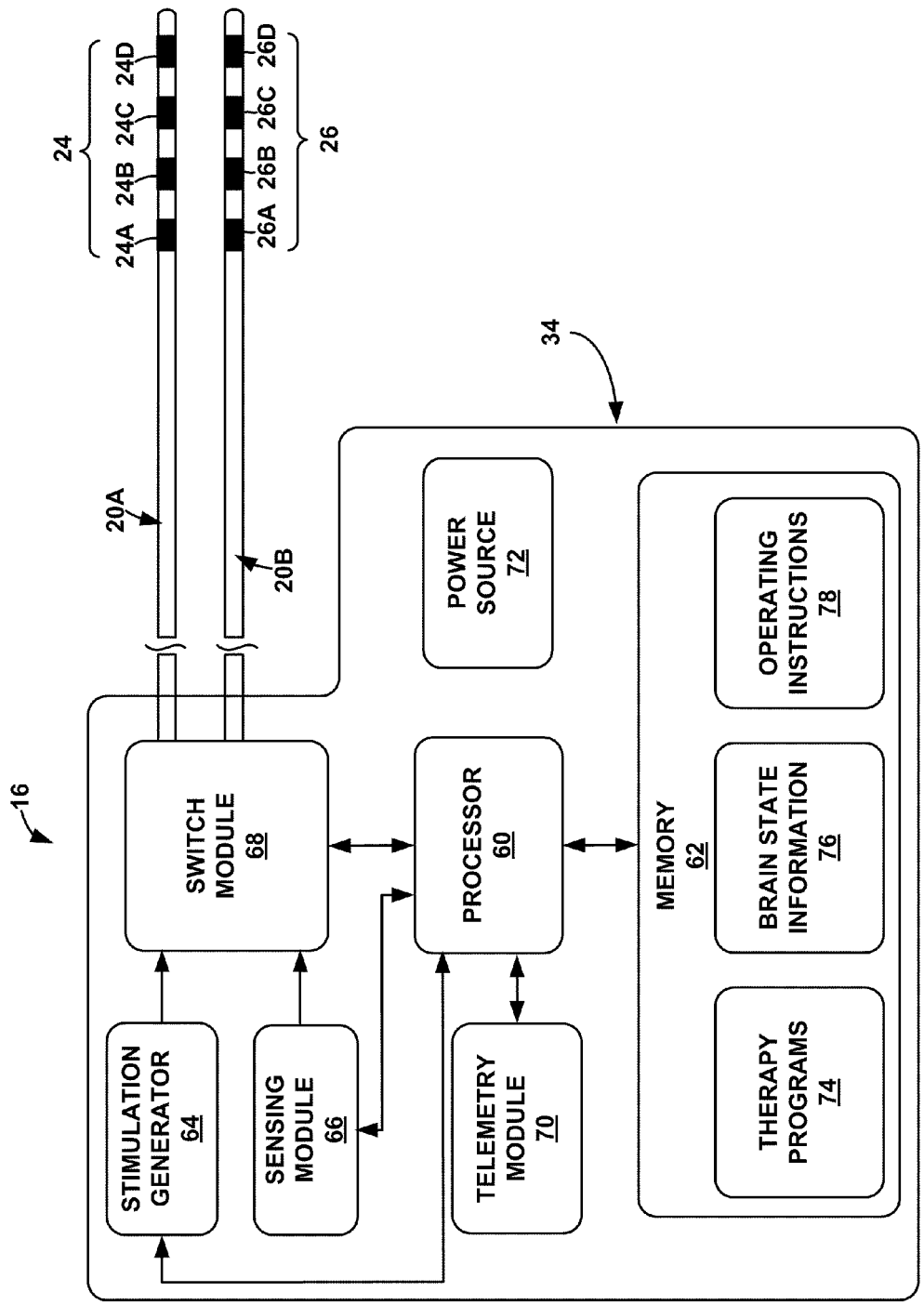
FIG. 3 is functional block diagram illustrating components of an example medical device.

FIG. 3 is functional block diagram illustrating components of IMD 16. In the example shown in FIG. 3, IMD 16 includes processor 60, memory 62, stimulation generator 64, sensing module 66, switch module 68, telemetry module 70, and power source 72. Memory 62 may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 3, memory 62 stores therapy programs 74, brain state information 76, and operating instructions 78 in separate memories within memory 62 or separate areas within memory 62. Each stored therapy program 74 defines a particular program of therapy in terms of respective values for electrical stimulation parameters, such as a stimulation electrode combination, electrode polarity, current or voltage amplitude, and, if stimulation generator 64 generates and delivers stimulation pulses, the therapy programs may define values for a pulse width, and pulse rate of a stimulation signal. In examples when IMD 16 delivers electrical stimulation therapy on a cyclic basis (as compared to a substantially continuous basis), memory 62 stores cycle parameter information, such as, on cycle time duration and off cycle duration. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Brain state information 76 stored by memory 62 includes brain signal data generated by sensing module 66 via at least one of electrodes 24, 26 and, in some cases, at least a portion of outer housing 34 of IMD 16, an electrode on outer housing 34 of IMD 16 or another reference. For example, the bioelectrical brain signals generated by one or more of the electrodes 24, 26 that indicates a brain state within one or more regions of brain 28 may be stored by memory 62 as brain state information. In addition, information relating to whether a sensed brain signal correlates to a desirable or undesirable brain state (e.g., a target brain state or a baseline brain state) may be stored by memory 62 as brain state information 76. In some examples, processor 60 may detect the brain state of patient 12 based on bioelectrical brain signals sensed by sensing module 66 via a subset of electrodes 24, 26. Thus, in some examples, processor 60 stores the bioelectrical brain signals as brain state information 76. Operating instructions 78 guide general operation of IMD 16 under control of processor 60, and may include instructions for monitoring brains signals within one or more brain regions via electrodes 24, 26 and/or selecting one or more therapy cycle parameters based on the monitored brain signals.

Stimulation generator 64, under the control of processor 60, generates stimulation signals for delivery to patient 12 via selected combinations of electrodes 24, 26. In some examples, stimulation generator 64 generates and delivers stimulation signals to one or more target regions of brain 28 (FIG. 1), e.g., anterior nucleus of the thalamus, of patient 12 via a select combination of electrodes 24, 26, where the stimulation signals have a frequency in a range of about 3 Hertz (Hz) to about 250 Hz, a voltage of about 0.1 volts to about 10.5 volts, and a pulse width of about 60 microseconds to about 450 microseconds. In some examples, the stimulation signals have a frequency of 120 Hz, a voltage of about 4 volts, and a pulse width of about 100 microseconds. In addition, in some examples, the stimulation signals have a frequency of 145 Hz, a voltage of about 5 volts, and a pulse width of about 145 microseconds. In some examples, stimulus frequencies below approximately 40 Hz (such as, e.g., between approximately 5 Hz and 40 Hz, between approximately 5 Hz and 10 Hz, approximately 10 Hz, or approximately 5 Hz) may be used to increase cortical excitability, while in some examples, stimulus frequencies greater than 40 Hz (such as, e.g., between approximately 40 Hz and 160 Hz, between approximately 80 Hz and 160 Hz, approximately 80 Hz, or approximately 160 Hz) may be used to suppress cortical excitability (see, e.g., FIG. 13A).

In addition, IMD 16 can deliver the stimulation signals using any suitable therapy cycle parameters, which includes the duration of an on cycle during which stimulation therapy is delivered to patient 12 and the duration of an off cycle during which stimulation therapy is not delivered to patient 12. For example, a therapy cycle may have an on cycle of about thirty seconds to about five minutes (e.g., about one minute) and an off cycle of about thirty seconds to about five minutes (e.g., about five minutes).

Other target tissue sites within brain 28 for stimulation signals or other types of therapy, other stimulation parameter values, and other therapy cycles are contemplated. Other ranges of therapy parameter values may also be useful, and may depend on the target stimulation site within patient 12, which may or may not be within brain 28. While stimulation pulses are described, stimulation signals may be of any form, such as continuous-time signals (e.g., sine waves) or the like.

In each of the examples described herein, if stimulation generator 64 shifts the delivery of stimulation energy between two therapy programs and/or two different electrode combinations, processor 60 of IMD 16 may provide instructions that cause stimulation generator 64 to time-interleave stimulation energy between the electrode combinations of the two therapy programs, as described in commonly-assigned U.S. Patent Application Publication No. 2006/0259099 by Steven Goetz et al., entitled, "SHIFTING BETWEEN ELECTRODE COMBINATIONS IN ELECTRICAL STIMULATION DEVICE," and filed on Apr. 10, 2006, the entire content of which is incorporated herein by reference. In the time-interleaved shifting example, the amplitudes of the stimulation signals delivered via the electrode combinations of the first and second therapy program are ramped downward and upward, respectively, in incremental steps until the amplitude of the second electrode combination reaches a target amplitude. The incremental steps may be different between ramping downward or ramping upward. The incremental steps in amplitude can be of a fixed size or may vary, e.g., according to an exponential, logarithmic or other algorithmic change. When the second electrode combination reaches its target amplitude, or possibly before, the first electrode combination can be shut off. Other techniques for shifting the delivery of stimulation signals between two therapy programs and/or electrode combinations may be used in other examples.

Processor 60 may include any one or more of a microprocessor, a controller, a digital signal processor (DSP), an application specific integrated circuit (ASIC), a field-programmable gate array (FPGA), discrete logic circuitry, and the functions attributed to processor 60 herein may be embodied as firmware, hardware, software or any combination thereof.

Processor 60 controls stimulation generator 64 according to therapy programs 74 stored in memory 62 to apply particular stimulation parameter values specified by one or more programs, such as amplitude, pulse width, and pulse rate.

Figure 4:
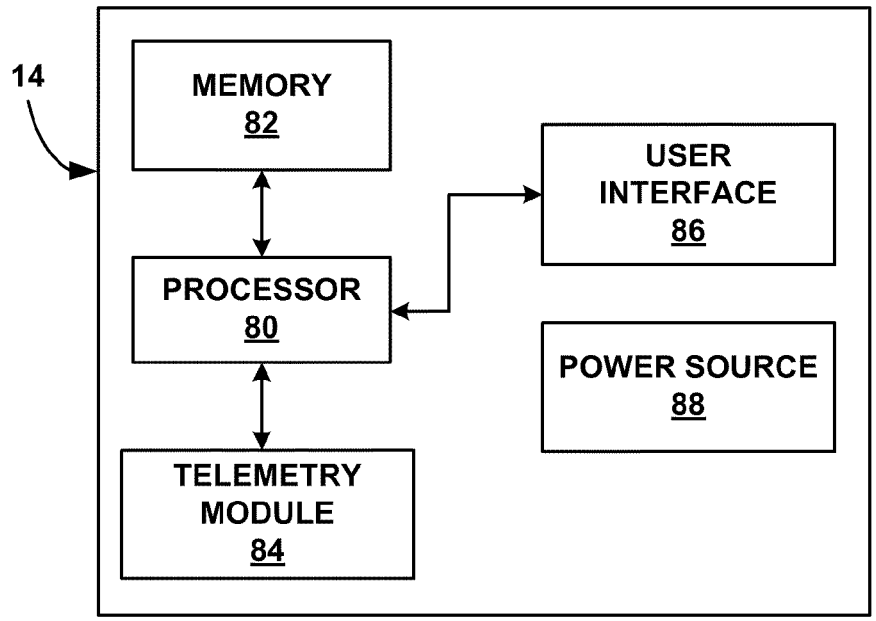
FIG. 4 is a functional block diagram illustrating components of an example medical device programmer.

In the example shown in FIG. 4, the set of electrodes 24 of lead 20A includes electrodes 24A, 24B, 24C, and 24D, and the set of electrodes 26 of lead 20B includes electrodes 26A, 26B, 26C, and 26D. Processor 60 may control switch module 68 to apply the stimulation signals generated by stimulation generator 64 to selected combinations of electrodes 24, 26. In particular, switch module 68 may couple stimulation signals to selected conductors within leads 20, which, in turn, deliver the stimulation signals across selected electrodes 24, 26. Switch module 68 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 64 is coupled to electrodes 24, 26 via switch module 68 and conductors within leads 20. In some examples, however, IMD 16 does not include switch module 68.

Stimulation generator 64 may be a single channel or multi-channel stimulation generator. In particular, stimulation generator 64 may be capable of delivering, a single stimulation pulse, multiple stimulation pulses or continuous signal at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing module 66 is configured to sense bioelectrical brain signals of patient 12 via a selected subset of electrodes 24, 26 or with one or more electrodes 24, 26 and at least a portion of a conductive outer housing 34 of IMD 16, an electrode on an outer housing of IMD 16 or another reference. Processor 60 may control switch module 68 to electrically connect sensing module 66 to selected electrodes 24, 26. In this way, sensing module 66 may selectively sense bioelectrical brain signals with different combinations of electrodes 24, 26 (and/or a reference other than an electrode 24, 26). As previously described, processor 60 may monitor the brain state of patient 12 via the sensed bioelectrical brain signals. In some examples, processor 60 may select one or more cycle parameters (e.g., on cycle duration, off cycle duration) and/or adjust one or more stimulation parameters values defined by a program (e.g., pulse rate, pulse width, pulse amplitude, electrode configuration) based on one or more characteristics of the bioelectrical brain signals monitored by sensing module 66. Although sensing module 66 is incorporated into a common housing 34 with stimulation generator 64 and processor 60 in FIG. 4, in other examples, sensing module 66 is in a separate outer housing from outer housing 34 of IMD 16 and communicates with processor 60 via wired or wireless communication techniques.

Telemetry module 70 supports wireless communication between IMD 16 and an external programmer 14 or another computing device under the control of processor 60. Processor 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14. For example, processor 60 may transmit brain state information 76 to programmer 14 via telemetry module 70.

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

FIG. 4 is a functional block diagram illustrating components of an example medical device programmer 14 (FIG. 1). Programmer 14 includes processor 80, memory 82, telemetry module 84, user interface 86, and power source 88. Processor 80 controls user interface 86 and telemetry module 84, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 14 through user interface 86. User interface 86 includes a display (not shown), such as a LCD or LED display or other type of screen, to present information related to the therapy, such as information related to bioelectrical signals sensed via a plurality of sense electrode combinations. In addition, user interface 86 may include an input mechanism to receive input from the user. The input mechanisms may include, for example, buttons, a keypad (e.g., an alphanumeric keypad), a peripheral pointing device or another input mechanism that allows the user to navigate though user interfaces presented by processor 80 of programmer 14 and provide input.

If programmer 14 includes buttons and a keypad, the buttons may be dedicated to performing a certain function, i.e., a power button, or the buttons and the keypad may be soft keys that change function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display. In other examples, user interface 86 also includes audio circuitry for providing audible instructions or sounds to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In some examples, at least some of the control of therapy delivery by IMD 16 may be implemented by processor 80 of programmer 14. For example, in some examples, processor 80 may receive sensed brain signal information from IMD 16 or from a sensing module that is separate from IMD 16. The separate sensing module may, but need not be, implanted within patient 12. Brain signal information may include, for example, a time domain characteristic (e.g., an amplitude) or a frequency domain characteristic (e.g., an energy level in one or more frequency bands) of brain signals monitored by sensing module 66 using one or more of electrodes 24, 26 (FIG. 3). Based on the monitored brain signal information, processor 80 may determine the brain state of patient 12 and control delivery of therapy from IMD 16 to patient 12 based on the determined brain state. For example, processor 80 may select one or more cycle timing parameters (e.g., off cycle time period and/or on cycle time period of therapy) based on the brain state of patient 12. Processor 80 may select the one or cycle timing parameters such that the therapy delivered via IMD 16 to patient 12 allows patient 12 to maintain a desirable brain state or evoke a change from an undesirable brain state to a desirable brain state.

Memory 82 may include instructions for operating user interface 86 and telemetry module 84, and for managing power source 88. Memory 82 may also store any therapy data retrieved from IMD 16 during the course of therapy, brain state information, and adjustment to one or more cycle timing parameters. The clinician may use this therapy data to determine the progression of the patient condition in order to plan future treatment for the seizure disorder (or other patient condition) of patient 12. Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 88 delivers operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate. Power source 88 may include circuitry to monitor power remaining within a battery. In this manner, user interface 86 may provide a current battery level indicator or low battery level indicator when the battery needs to be replaced or recharged. In some cases, power source 88 may be capable of estimating the remaining time of operation using the current battery.

Figure 5:
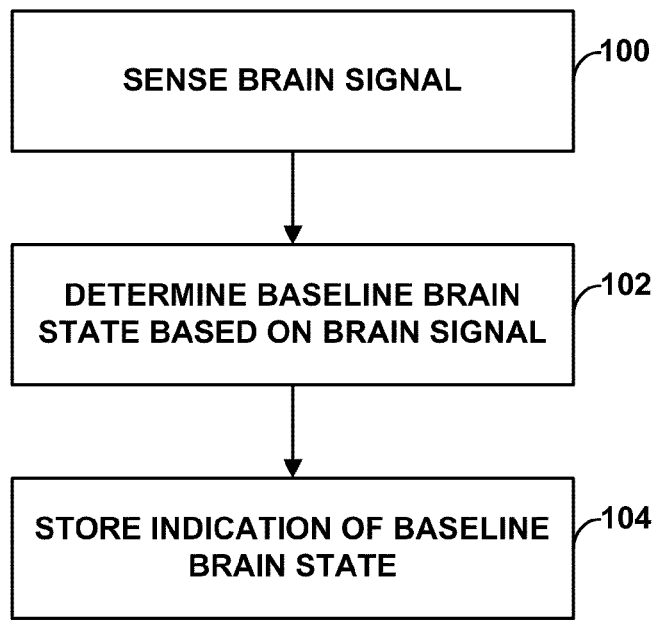
FIG. 5 is a flow diagram illustrating an example technique for determining a baseline brain state of a patient.

FIG. 5 is a flow diagram illustrating an example technique for determining a baseline brain state of patient 12. While the technique shown in FIG. 5, as well as the other figures are described with respect to processor 60 of IMD 16, in other examples, a processor of another device, such as processor 80 of programmer 14 (FIG. 4) can perform any part of the techniques described herein, alone or in combination with another device.

In accordance with the technique shown in FIG. 5, processor 60 of IMD 16 controls sensing module 66 to sense a brain signal of patient 12, e.g., via one or more of electrodes 24, 26 on leads 20 (100). Processor 60 of IMD 16 determines the baseline brain state of patient 12 based on one or more characteristics of the sensed brain signal (102). Processor 60 of IMD 16 then stores an indication of the baseline brain state as brain state information 76 in memory 62 (104).

Processor 60 may determine the baseline brain state of patient 12 by analyzing the bioelectrical behavior of brain signals within the sensed region when unaffected by delivery of stimulation therapy from stimulation generator 64 of IMD 16. For example, processor 60 can determine the baseline brain state of patient 12 prior to any therapy delivery by IMD 16 or after a washout period resulting from therapy delivery (e.g., after any carryover effects from stimulation therapy have substantially dissipated). In some cases, the baseline brain state may represent the patient condition that is undesirable (e.g., a brain state in which one or more symptoms associated with the patient disorder to be treated via therapy are observed or a brain state in which a patient event is likely to occur), and therapy may be delivered to patient 12 to improve the baseline brain state or otherwise mitigate the effects of the baseline state.

In some examples, the bioelectrical behavior of a region of brain 28 may be characterized by a frequency domain characteristic and/or a time domain characteristic of a brain signal sensed within the region. Processor 60 may identify one or more characteristics of the sensed brain signals and store the identified characteristic(s) as indicators of the baseline brain state. In such as case, the baseline brain state of may be used as a reference brain state useful for determining the changes to bioelectrical brain activity within the region of brain 28 in which the brain signal used to determine the baseline brain state was sensed. In some examples, processor 60 defines the brain state based on the level of cortical activity derived from the sensed brain signal. The level of cortical activity can be indicated by any suitable signal characteristic. For example, the level of cortical activity within brain 28 of patient 12 can be indicated by the average, peak, mean or instantaneous amplitude of a sensed bioelectrical brain signal over a predetermined period of time (e.g., the average amplitude over a period of time of about one second to about five minutes) or the peak-to-peak variability of the bioelectrical brain signal, or variability of one or more frequency domain characteristics (e.g., the average, peak, mean or instantaneous energy level within a selected frequency band over predetermined period of time) over time. As other examples, the level of cortical activity within brain 28 of patient 12 can be indicated by variance between the instant, median, or mean amplitude of a bioelectrical brain signal over time, whereby the variance may be between subsequent slots of time or between a sensed bioelectrical brain signal and a stored average, peak, mean or instantaneous of the amplitude determined based on a prior period of time.

In some examples, the baseline brain state determined by processor 60 can also be used to determine the length of a washout period following delivery of electrical stimulation from stimulation generator 64 to brain 28, which may be delivered to brain 28 via one or more of electrodes 24, 26 during an on cycle.

An example of a frequency domain characteristic of a brain signal may include power level (or energy level) within a particular frequency band. The power level may be determined based on, for example, a spectral analysis of a bioelectrical brain signal. The spectral analysis may indicate the distribution over frequency of the power contained in a signal, based on a finite set of data. An example of a time domain characteristic of a brain signal may include an amplitude of the brain signal.

In some examples, the frequency domain characteristic may comprise a relative power level in a particular frequency band. Thus, while "power levels" within a selected frequency band of a sensed brain signal are generally referred to herein, the power level may be a relative power level. A relative power level may include a ratio of a power level in a selected frequency band of a sensed brain signal to the overall power of the sensed brain signal. The power level in the selected frequency band may be determined using any suitable technique. In some examples, processor 60 of IMD 16 may average the power level of the selected frequency band of a sensed brain signal over a predetermined time period, such as about ten seconds to about two minutes, although other time ranges are also contemplated. In other examples, the selected frequency band power level may be a median power level over a predetermined range of time, such as about ten seconds to about two minutes. The activity within the selected frequency band of a brain signal, as well as other frequency bands of interest, may fluctuate over time. Thus, the power level in the selected frequency band at one instant in time may not provide an accurate and precise indication of the energy of the brain signal in the selected frequency band. Averaging or otherwise monitoring the power level in the selected frequency band over time may help capture a range of power levels, and, therefore, a better indication of the patient's pathological state in the particular brain region sensed by IMD 16.

The overall power of a sensed bioelectrical brain signal may be determined using any suitable technique. In one example, processor 60 of IMD 16 (or another device, such as programmer 14) may determine an overall power level of a sensed bioelectrical brain signal based on the total power level of a swept spectrum of the brain signal. To generate the swept spectrum, the processor may control sensing module 26 to tune to consecutive frequency bands over time, and the processor may assemble a pseudo-spectrogram of the sensed bioelectrical brain signal based on the power level in each of the extracted frequency bands. The pseudo-spectrogram may be indicative of the energy of the frequency content of the bioelectrical brain signal within a particular window of time.

As will be described in further detail below, a process similar to that of the example in FIG. 5 may be used by processor 60 to determine a target brain state of patient 12. In such a case, the target brain state may represent the patient brain state that is desirable, e.g., because the target brain state is defined based on one or more characteristics of sensed brain signals that coincide with effective treatment of the patient disorder. The target brain state may be achieved by delivering electrical stimulation to a region of brain 28. Using the target brain state, processor 80 may control delivery of electrical stimulation to brain 28 in a manner that maintains the brain state of patient 12 within a threshold range of the target brain state rather than a baseline brain state.

Figure 6:
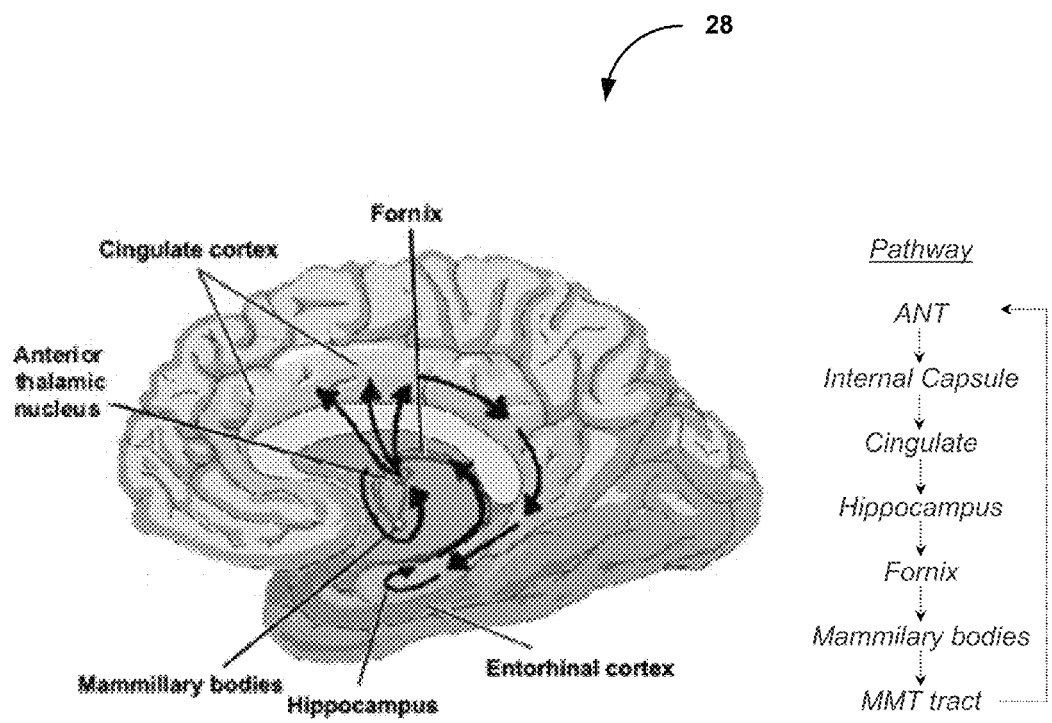
FIG. 6 is a conceptual diagram illustrating example physiological regions of a brain of a patient.

FIG. 6 is a conceptual diagram illustrating example regions of brain 28 of patient 12 and, in particular, regions of brain 28 included in the Circuit of Papez (also referred to as the Papez Circuit). The regions of the brain 28 within the Circuit of Papez are involved in the cortical control of emotion as well as storing memory. In addition, this circuit is known to be involved in the generation and spread of seizure activity. The Circuit of Papez is one of the major pathways of the limbic system, and includes the anterior thalamic nucleus (AN), internal capsule, cingulate, hippocampus (HC), formix, mammilary bodies, and mammillothalamic tract (MMT). The regions of brain 28 within the Circuit of Papez may be considered to be functionally related, such that activity within one part of the Circuit of Papez may affect activity within another part of the Circuit of Papez.

In some examples, electrodes 24, 26 may be implanted to deliver electrical stimulation therapy generated via stimulation generator 64 (FIG. 3) and/or monitor bioelectrical brain signals within one or more regions of the brain in the Circuit of Papez, such as, e.g., the anterior thalamic nucleus, the internal capsule, the cingulate, the formix, the mammillary bodies, the mammillothalamic tract, and/or hippocampus. In some examples, a disorder of patient 12 may be effectively managed by controlling or influence the brain state of patient 12 defined by one or more characteristics of bioelectrical signals sensed within one or more regions of the Circuit of Papez. For example, with respect to seizure disorders, therapy may be delivered from IMD 16 to regions within the Circuit of Papez to suppress cortical activity within regions of the Circuit of Papez, such as, e.g., the HC. Suppression of cortical activity within the HC via therapy may reduce the likelihood of a seizure by patient 12. As another example, for treatment of Alzheimer's disease, therapy may be delivered from IMD 16 to regions within the Circuit of Papez to increase cortical activity within the regions of the Circuit of Papez, such as, e.g., the HC. Increasing cortical activity within the HC via therapy may reduce symptoms of Alzheimer's disease such as memory loss.

The delivery of stimulation in the AN may be useful as the AN is a central site of the Circuit of Papez, and, as a result, stimulating the AN can help target a plurality of seizure foci that may be present in the Circuit of Papez even if the seizure focus is not in the AN. Such a relationship may help minimize the burden on a clinician in indentifying a useful target stimulation site by locating the exact seizure focus. This can be referred to as a remote stimulation approach. Moreover, stimulating in the AN can be less invasive to the patient because the leads can be relatively easily implanted in the AN compared to, e.g., the HC, although leads can be implanted in the HC as well. One or more of the plots described below may illustrate that delivering stimulation to the AN may provide benefits to other regions of the Circuit of Papez.

In some examples, a target brain state is indicated by one or more characteristics of a bioelectrical brain signal that is indicative of a particular level of cortical activity in which symptoms of a patient condition are managed or a level of cortical activity that indicates a state in which the likelihood of the onset of a patient event (e.g., a seizure) is minimized compared to a baseline patient state in which no therapy is delivered to patient 12 or no therapeutic effects of therapy delivery are observed. Processor 60, alone or with the aid of a clinician, can determine the target brain state at any suitable time, e.g., prior to any delivery of stimulation by IMD 16 or after any carryover effects from stimulation therapy have substantially dissipated. Processor 60 of IMD 16 can control stimulation generator 64 based on the target brain state. For example, processor 60 of IMD 16 may monitor brain signals within one or more regions of the Circuit of Papez of brain 28 to monitor the brain state of patient 12 and control stimulation generator 64 to generate and deliver therapy to at least a portion of the Circuit of Papez to evoke bioelectrical brain signals that are within a threshold value of the target brain state.

In some examples, processor 60 of IMD 16 adjusts the off cycle duration of a therapy cycle such that the delivery of therapy to patient 12 is withheld when the carryover effects of therapy delivered during the previous on cycle cause the maintenance of the target brain state. Processor 60 can select the off cycle duration such that therapy is delivered prior to dissipation of carryover effects or once the monitored brain signals are outside of a threshold range of the target brain state. In this way, selection of the off cycle duration allows processor 60 to control delivery of stimulation to brain 28 to evoke brain signals within the threshold range of the target brain state.

The threshold range of the target brain state can be predetermined by a clinician and can be specific to patient 12 or more general to more than one patient. In examples in which the brain state is indicated by a time domain characteristic or a frequency domain characteristic (e.g., an amplitude) of the bioelectrical brain signal, the threshold range is about 1% to about 25% of a deviance from the characteristic indicative of the target brain state, such as about 1% to about 10%. However, other threshold ranges are contemplated and can be selected based on a particular patient and/or patient condition. In general, the threshold range is selected to indicate a brain state in which any therapeutic benefits of therapy delivery by IMD 16 are still observed. For example, the threshold range can be selected such in the brain states observed within the window defined by the threshold range that, the symptoms of the patient condition mitigated by the therapy delivery are still mitigated and are still relatively minor compared to the baseline patient state. As another example, threshold range can be selected such in the brain states observed within the window defined by the threshold range, the possibility of the onset of a patient event are still minimized despite a deviance from the target brain state.

As described above, system 10 may be configured to deliver electrical stimulation to brain 28 and monitor brain signals of patient 12 at the same or different regions in brain 28. As illustrated in FIG. 6, regions within the Circuit of Papez may be connected to one another via neurological pathways such that activity within one region of brain 28 may affect activity within another region of brain 28. As such, electrical stimulation delivered from IMD 16 to a particular region of the Circuit of Papez may influence brain signals in one or more other regions of the Circuit of Papez. In the case of influencing bioelectrical brain signal activity within the HC of the Circuit of Papez, electrodes 24, 26 may be implanted to deliver electrical stimulation directly to the HC or may be implanted to deliver electrical stimulation to another region of the Circuit of Papez, e.g., the AN, to treat a patient disorder. Additionally, sensing module 66 may monitor brain signals via electrodes 24, 26 positioned within the HC, AN or other region in the Circuit of Papez, which may or may not be the same region that stimulation is delivered to brain 28.

Figure 7A:
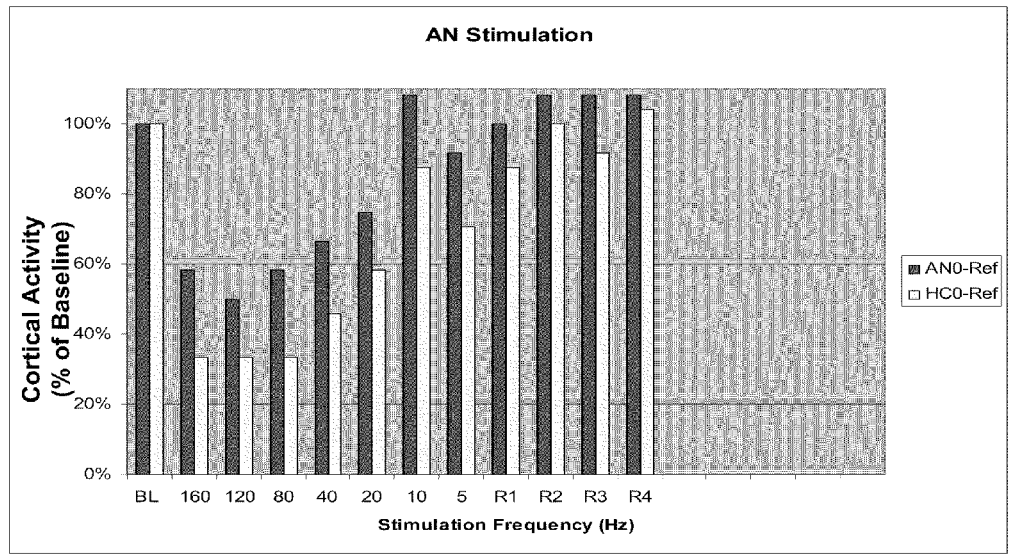
FIGS. 7A and 7B are plots illustrating changes to cortical activity sensed at both the anterior thalamic nucleus and hippocampus regions of the brain evoked by example electrical stimulation to the anterior thalamic nucleus of an ovine subject.
Figure 7B:
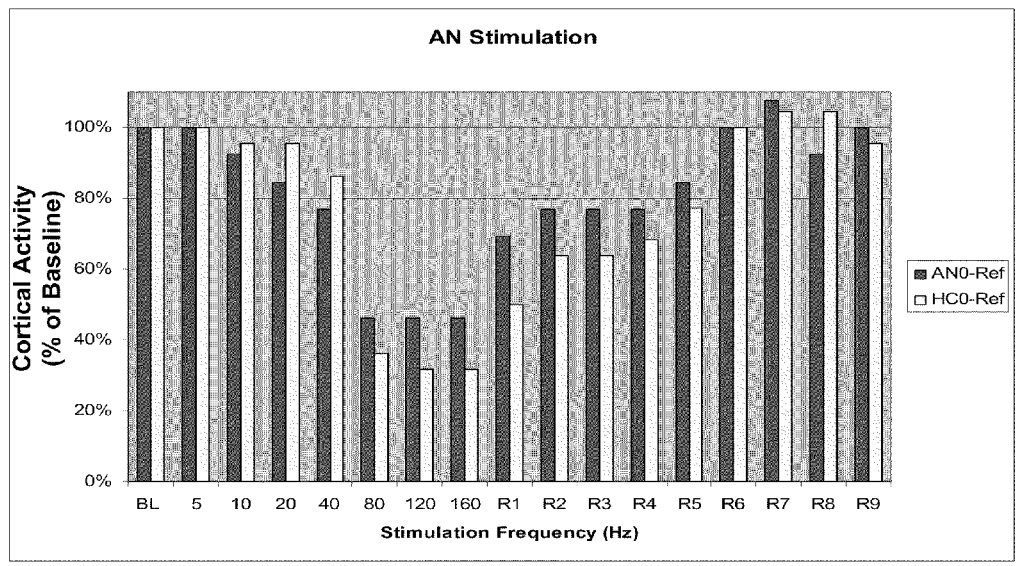

FIGS. 7A and 7B are plots illustrating changes to cortical activity sensed at both the AN of the thalamus and HC regions of a brain of an ovine subject, where the cortical activity is evoked by example electrical stimulation to the AN of the thalamus. In the example shown in FIG. 7A, stimulation pulses were delivered to the AN of the ovine subject in ten-second bursts at frequencies of about 160 Hz, about 120 Hz, about 80 Hz, about 40 Hz, about 20 Hz, about 10 Hz, and about 5 Hz, progressing in that order as the plot moves from left to right when viewing FIG. 7A. In FIG. 7B, stimulation pulses were delivered to the AN in ten-second bursts at frequencies of about 5 Hz, about 10 Hz, about 20 Hz, about 40 Hz, about 80 Hz, about 120 Hz, and about 160 Hz, progressing in that order as the plot moves from left to right when viewing FIG. 7B. For each stimulation frequency, a single, ten-second burst was delivered, followed by a 50-second "off" period. The pulse width of the stimulation was approximately 120 microseconds and the pulse amplitude was approximately 10 volts.

In conjunction with the therapy delivery, cortical activity was monitored in the both the AN and HC of the brain of the ovine subject to determine the changes evoked by the delivery of stimulation pulses to the AN. Cortical activity was also monitored during multiple consecutive one-minute recovery periods (labeled R1, R2, R3 and so forth in FIGS. 7A and 7B) following delivery of stimulation therapy at the final frequency value (i.e., stimulation at about 5 Hz in FIG. 7A and 160 Hz in FIG. 7B). To evaluate the changes to cortical activity, brain signals were monitored in both the AN and HC prior to delivery of the electrical stimulation to determine a baseline cortical activity (labeled "BL" in FIGS. 7A and 7B) for each region, and FIGS. 7A and 7B are plots illustrating changes in cortical activity evoked by the delivery of electrical stimulation to the AN for the described stimulation conditions relative to the baseline cortical activity in each of the HC and AN.

As illustrated by the plots of FIGS. 7A and 7B, the suppression of cortical activity increased as the frequency of the stimulation to the AN increased. Furthermore, the plots of FIGS. 7A and 7B illustrate a correlation between changes to the cortical activity sensed at the AN and changes to the cortical activity sensed at the HC. This correlation between HC and AN with regard to the changes in cortical activity evoked by delivery of electrical stimulation to the AN indicates that bioelectrical brain signals sensed in the AN can be used to determine changes in the bioelectrical brain signals in the HC evoked by delivery of electrical stimulation to the AN. Therefore, it is believed that leads 20 may be implanted in brain 28 of patient 12 such that stimulation generator 64 delivers electrical stimulation via a selected subset of electrodes 24, 26 to the AN and sensing module 66 monitors brain signals via a selected subset of electrodes 24, 26 in the AN to detect changes to the bioelectrical signals, e.g., suppression of to cortical activity, in the HC evoked by the electrical stimulation delivered to the AN.

In other examples, system 10 may be configured to deliver electrical stimulation directly to the AN via a first set of electrodes and directly sense brain signals via a second set of electrodes located in the HC, where the first and second sets of electrodes are carried by a separate or common leads and have at least one different electrode. However, such a configuration may be more invasive than a configuration in which a single set of electrodes in the AN are used to deliver therapy to the AN and monitor brain signals to detect changes to the brain signal evoked by the therapy delivery. The physiological relationship described with regard to FIGS. 6, 7A and 7B is not limited to the AN and HC or Circuit of Papez in general, but may also be a characteristic of regions of common neurological pathways of the brain.

Figure 8A:
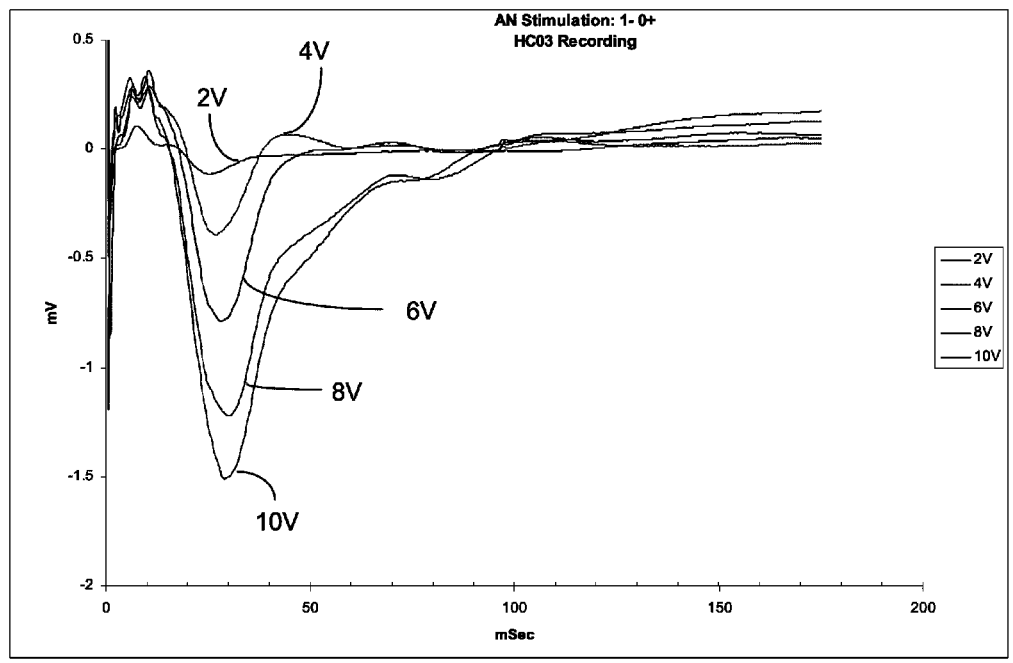
FIGS. 8A and 8B are plots illustrating example evoked potentials in the hippocampus region resulting from stimulation of the anterior thalamic nucleus region of an ovine subject.
Figure 8B:
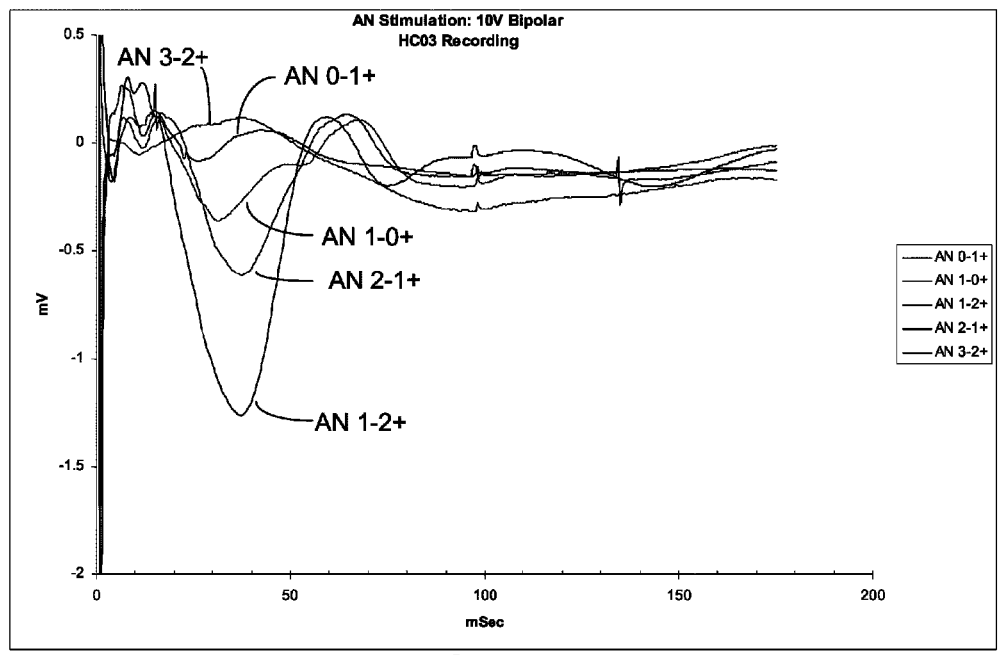

FIGS. 8A and 8B are plots illustrating example evoked potentials in the HC region resulting from the delivery of stimulation of the AN region of an ovine subject. With respect to the data shown in FIG. 8A, the example stimulation was delivered in the form of electrical stimulation pulses having voltage amplitudes of about 2 volts, about 4 volts, about 6 volts, about 8 volts, and about 10 volts. In each case, the electrical stimulation pulses had a pulse width of about 120 microseconds, and were delivered at a pulse rate of about 5 HZ. For each amplitude, the electrical stimulation was delivered to the AN of the ovine subject in single 30 second burst. In conjunction with the delivery of the electrical stimulation to the AN, brain signals in the HC of the ovine subject were monitored to determine evoked potentials.

As shown in the plot of FIG. 8A, maximum evoked potential in the HC increased as the voltage amplitude of the stimulation pulses delivered to the AN increased, with the largest evoked potential corresponding to stimulation pulses with a pulse amplitude of about 10 volts. The presence of evoked potential in the HC from delivery of stimulation to the AN indicates a physiological connection between the two regions.

The plot of FIG. 8B illustrates evoked potentials in the HC from delivery of electrical stimulation to the AN via various bi-polar electrode configurations. For FIG. 8B, the electrical stimulation delivered via the various bi-polar electrodes configuration was in the form of electrical stimulation pulses having voltage amplitudes of about 10 volts, a pulse width of about 120 microseconds, and were delivered at a pulse rate of about 5 Hz. The electrical stimulation was delivered to the AN via each bi-polar configuration in 30 second bursts. As shown in FIG. 8B, the evoked potential measured in the HC depended on the electrode configuration used to deliver stimulation to the AN. This again indicates that there is a functional relationship between the HC and the AN of a brain, and, therefore, delivery of stimulation to the AN can generate evoked responses in the HC.

Figure 9A:
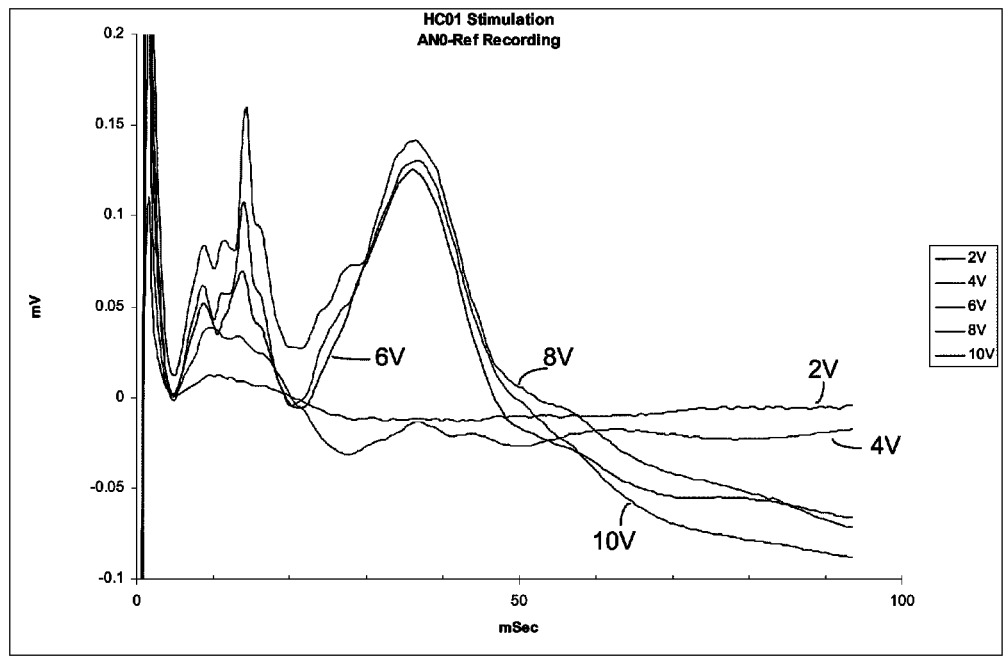
FIGS. 9A and 9B are plots illustrating example evoked potentials in the anterior thalamic nucleus region resulting from stimulation of the hippocampus region of an ovine subject.
Figure 9B:
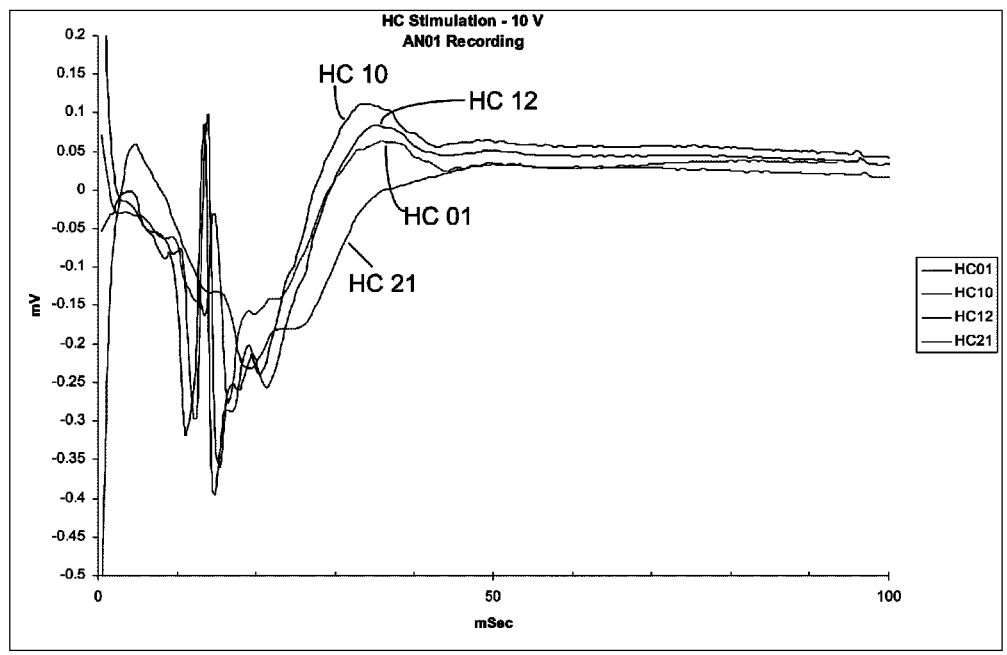

FIGS. 9A and 9B are plots illustrating example evoked potentials in the AN of a thalamus of an ovine subject by stimulation of the HC. For FIG. 9A, the stimulation was delivered to the HC of the ovine subject in the form of electrical stimulation pulses having voltage amplitudes of about 2 volts, about 4 volts, about 6 volts, about 8 volts, and about 10 volts. For each amplitude, the electrical stimulation pulses had a pulse width of about 120 microseconds, and were delivered at a pulse rate of about 5 Hz. For each amplitude, the electrical stimulation was delivered to the HC in a single 30 second burst. In conjunction with the delivery of the electrical stimulation to the HC, brain signals in the AN were monitored to determine evoked potentials.

As shown in the plot of FIG. 9A, evoked potential in the AN varied based on the voltage amplitude of the stimulation pulses delivered to the HC. Furthermore, the latency duration (e.g., a time from stimulation to a peak of an evoked potential resulting from the stimulation) indicated by signals sensed in the AN varied based on the pulse amplitude of the stimulation delivered to the HC. The HC stimulation generated shorter latency evoked potentials in the AN compared to that of the evoked potentials in the HC from delivery of stimulation pulses to the AN (shown in FIG. 8A).

The plot of FIG. 9B illustrates evoked potentials in the AN from delivery of electrical stimulation to the HC via various bi-polar electrode configurations. For FIG. 9B, the electrical stimulation delivered via the various bi-polar electrodes configuration was in the form of electrical stimulation pulses having voltage amplitudes of about 10 volts, a pulse width of about 120 microseconds, and were delivered at a pulse rate of about 5 Hz. The electrical stimulation was delivered to the HC via each bi-polar configuration for a single, 30 second burst. As shown in FIG. 9B, the evoked potential measured in the AC depended on the electrode configuration used to deliver stimulation to the HC. FIGS. 9A and 9B further indicate that there is a functional relationship between the HC and the AN of a brain, and, therefore, delivery of stimulation to the HC can generate evoked responses in the AN.

Figure 10:
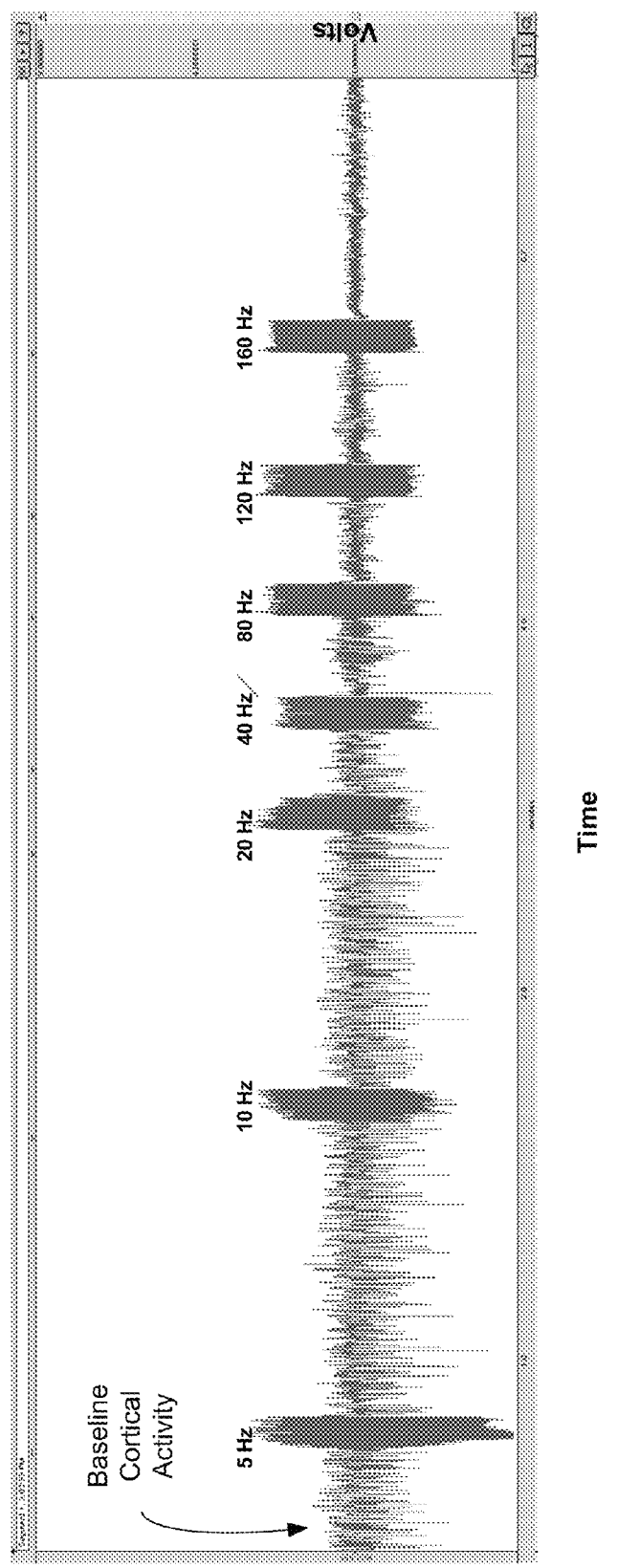
FIG. 10 is a plot illustrating example effects on cortical activity in the hippocampus region from delivery of example stimulation to the anterior thalamic nucleus region of an ovine subject at various example pulse frequencies.

FIG. 10 is a plot illustrating example effects on cortical activity in the HC by delivery of example stimulation to the AN of an ovine subject at various example stimulation pulse rates. As indicated in FIG. 10, stimulation was sequentially delivered at pulse rates of about 5 Hz, about 10 Hz, about 20 Hz, about 40 Hz, about 80 Hz, about 120 Hz, and about 160 Hz, separated by periods during which no stimulation delivered to the AN. The stimulation pulses had pulse widths of approximately 120 microseconds and pulse amplitudes of approximately 8.1 volts. For each frequency, the stimulation was delivered in a single, 10 second burst.

As shown in FIG. 10, the effect of the electrical stimulation delivered to the AN on the cortical activity in the HC of the ovine subject varied according to the pulse rate of the delivered electrical stimulation. Changes to the cortical activity are illustrated by a comparison of the cortical activity sensed in the HC during a baseline state (as labeled in FIG. 10) where the bioelectrical brain signals in the HC were not influenced by electrical stimulation, and the cortical activity sensed in the HC following delivery of electrical stimulation according to each stimulation pulse rate. As shown in FIG. 10, the delivery of relatively higher frequency stimulation to the AN significantly suppressed cortical activity in the HC in the period directly following delivery of the electrical stimulation (e.g., 40 Hz, 80 Hz, 120 Hz, 160 Hz). In general, the test stimulation indicates that effect that the stimulation had on cortical activity sensed in the HC compared to the baseline state increased as the frequency of the stimulation delivered to the AN increased. As described above, suppression of cortical activity in the HC may effectively treat one or more patient disorders, such as, e.g., seizure disorders. In other examples, stimulation therapy may increase cortical activity in the HC to effectively treat one or more patient disorders, such as, e.g., Alzheimer's disease.

Figure 11:
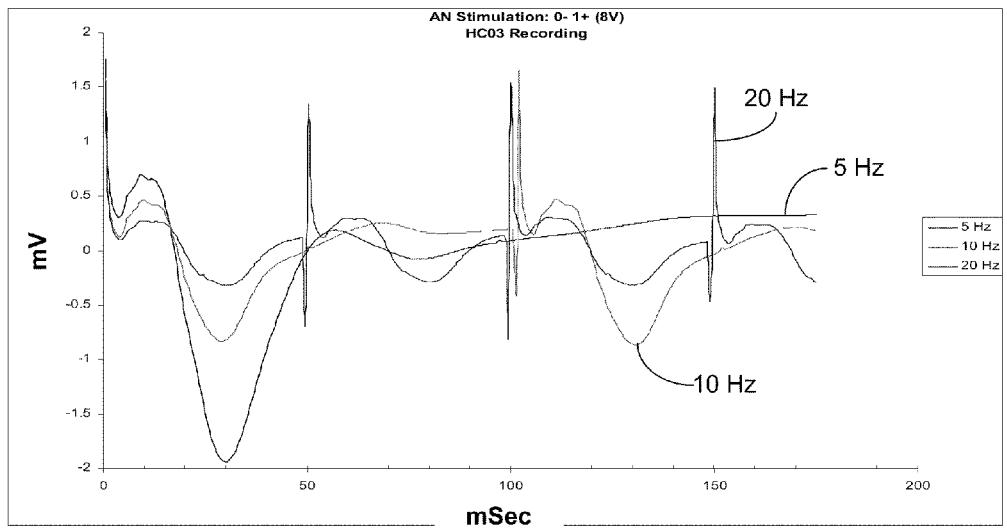
FIGS. 11 and 12 are plots illustrating example effects on evoked potentials in the hippocampus region of an ovine subject from example stimulation of the anterior thalamic nucleus region at various example pulse frequencies.
Figure 12:
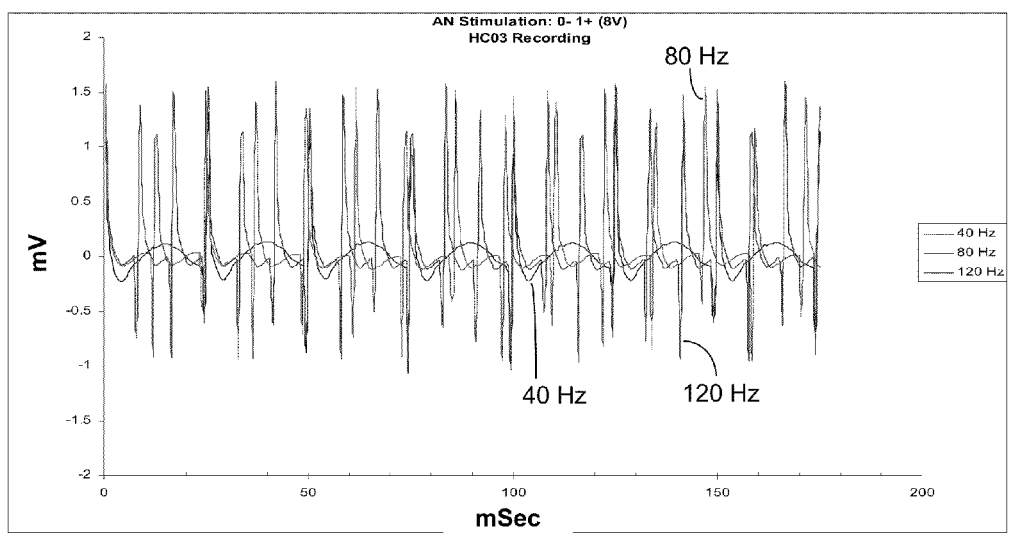

FIGS. 11 and 12 are plots illustrating measured evoked potentials in the HC at various electrical signal frequencies during delivery of electrical stimulation to the AN. FIG. 11 shows the evoked potentials recorded during stimulation of the approximately 5, 10, and 20 Hz bursts from the example stimulation shown in FIG. 10 (on an expanded time scale). FIG. 12 shows the evoked potential recorded during the approximately 40, 80, and 120 Hz bursts from the example stimulation shown in FIG. 10. FIGS. 11 and 12 suggest that, during stimulation, evoked potentials are observed with the relatively low frequency stimulation (5, 10, and 20 Hz) but not the relatively high frequency stimulation (40, 80, and 120 Hz).

Figure 13A:
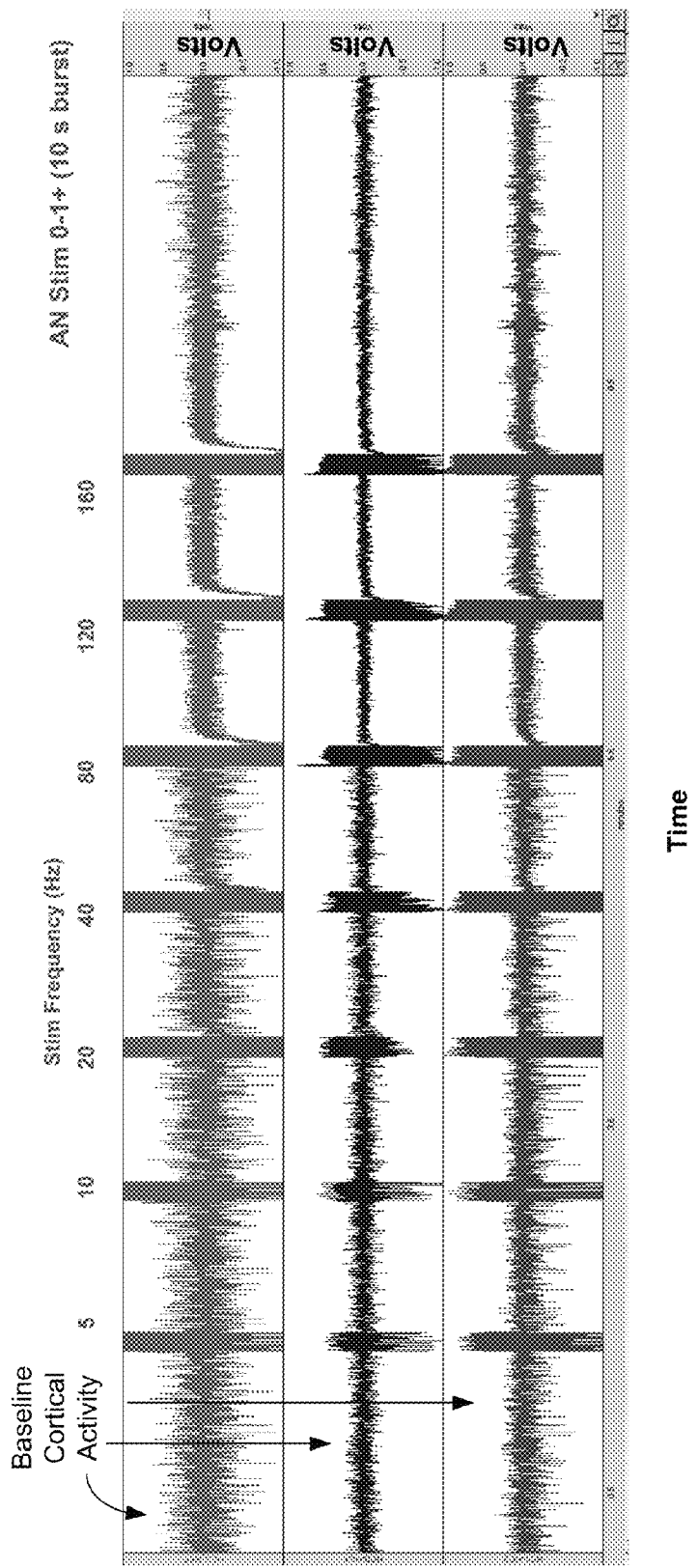
FIGS. 13A and 13B are plots illustrating example effects on cortical activity in the hippocampus region of an ovine subject from example stimulation of the anterior thalamic nucleus region at various example pulse frequencies.
Figure 13B:
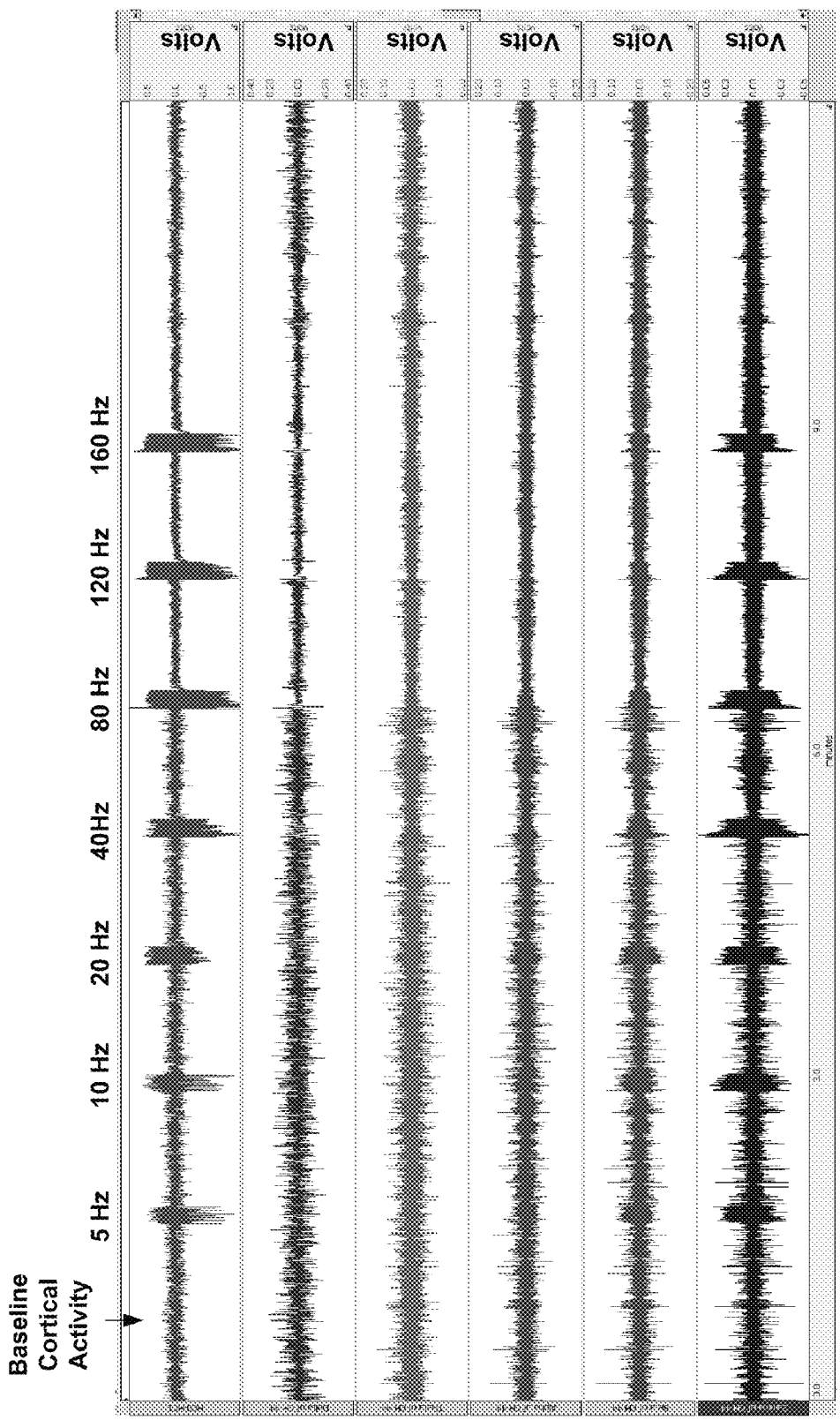

FIGS. 13A and 13B are plots illustrating example effects on cortical activity in the hippocampus region of an ovine subject from example stimulation of the anterior thalamic nucleus region at various example pulse frequencies. Similar to that of FIG. 10, stimulation was sequentially delivered to the AN at pulse rates of about 5 Hz, about 10 Hz, about 20 Hz, about 40 Hz, about 80 Hz, about 120 Hz, and about 160 Hz, separated by periods during which no stimulation delivered to the AC. At each frequency, the stimulation was delivery to the AN in 10 second bursts. The stimulation had a pulse width of approximately 120 microseconds and a pulse amplitude of approximately 10 volts.

The plot shown in FIG. 13A includes three graphs (having a relative arrangement of top, middle, and bottom) illustrating cortical activity in the HC sensed via three different bi-polar electrode configurations. As shown in FIG. 13A, the effect of AN electrical stimulation on cortical activity sensed within the HC of the ovine subject varied based on the electrode configuration for sensing bioelectrical brain signals within the HC. The electrode configuration for sensing bioelectrical brain signals within the HC of the ovine subject can affect the proximity to the AN, which, therefore, can affect the activity sensed within the HC resulting from delivery of stimulation to the AN.

The plot shown in FIG. 13B includes six graphs (referred in order from top to bottom as graphs 1 to 6) illustrating cortical activity in the HC in particular frequency bands of the sensed brain signal. The graph 1 illustrates the raw signal sensed in the HC. Graphs 2-6 illustrate the delta, theta, alpha, beta, and gamma frequency bands, respectively, of derived from the raw signal. As shown in FIG. 13B, the effect of AN electrical stimulation on cortical activity sensed within the HC of the ovine subject varied within specific frequency bands of the sensed brain signal. The effect of AN simulation on the HC can be monitored based on the raw signal and/or frequency bands within the brain signal. In some examples, one or more characteristics of a sensed brain signal within specific frequency band(s), e.g., cortical activity, may be used to define the brain state of patient.

As described above, in some examples, therapy system 10 may be configured to select at least one parameter of a therapy cycle based on a bioelectrical signal sensed within of brain 28 by sensing module 66 of IMD 16 (FIG. 3). In some examples, processor 60 of IMD 16 controls stimulation generator 64 to generate and deliver therapy to brain 28 via a selected subset of electrodes 24, 26 according to the at least one parameters of the therapy cycle. Example therapy cycle parameters may include the duration of the on cycle (e.g., the time period of a therapy cycle during which stimulation generator 64 delivers electrical stimulation signals to brain 28 via at least one of electrodes 24, 26) and the duration of the off cycle (e.g., the time period of a therapy cycle during which stimulation generator 64 withholds delivery of electrical stimulation to brain 28). Processor 60 may select the at least one parameter of a therapy cycle such that brain signals of patient 12 are maintained at a brain state effective in for treating the patient disorder throughout both the on cycle and off cycle of cycle therapy.

As discussed above, a clinician, processor 60 of IMD 16 or a processor of another device (e.g., programmer 14) can select the at least one parameter of a therapy cycle based on a washout period of stimulation therapy delivered during a particular on cycle with a particular set of therapy parameter values.

Figure 14:
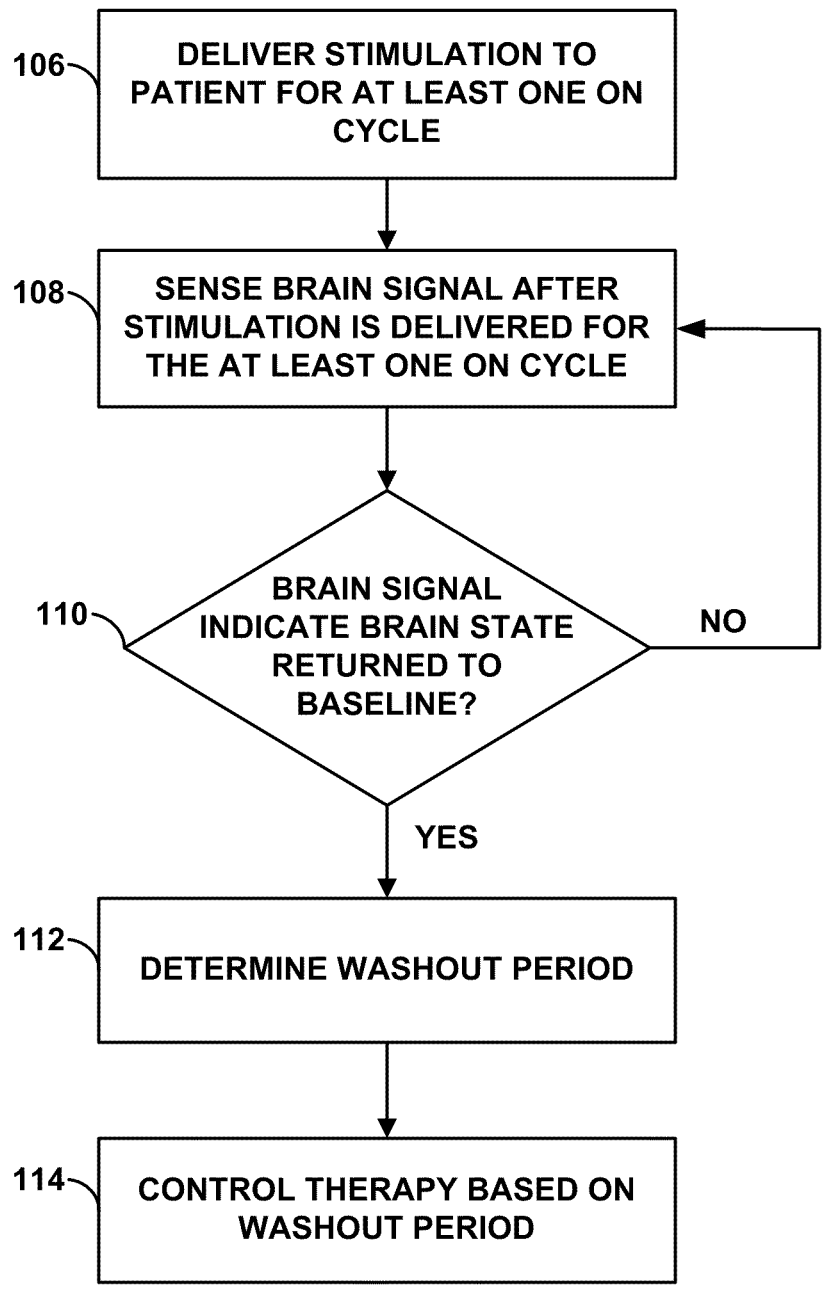
FIG. 14 is a flow diagram illustrating an example technique for determining a washout period associated with an example stimulation therapy.

FIG. 14 is a flow diagram illustrating an example technique for determining a washout period associated with example stimulation therapy. As previously described, a washout period is the period of time following delivery of therapy to patient 12 during which one or more carryover effects from the therapy delivery substantially dissipates. The end of the washout period associated with a therapy program may be the time at which at least one of the physiological effects resulting from the delivery of electrical stimulation therapy to patient 12 according to the therapy program have substantially dissipated, such that patient 12 returns to a baseline brain state. The baseline brain state may be, for example, the brain state defined by one or more characteristics of bioelectrical brain signals prior to the delivery of any therapy to patient 12. As described above, FIG. 5 illustrates an example process for determining the baseline brain state of a patient, and storing indicators of the brain state for future identification.

As shown in FIG. 14, to determine the washout period, processor 60 of IMD 16 controls stimulation generator 64 of IMD 16 to generate and deliver electrical stimulation to one or more regions of brain 28 via one or more electrodes 24, 26 for at least one on cycle (106). As described above, when active for therapy, IMD 16 may be configured to generate and deliver electrical stimulation, e.g., stimulation pulses, to brain 28 on a cyclic basis rather than a continuous basis. During an on cycle, processor 60 of IMD 16 controls stimulation generator 64 to generate and deliver electrical stimulation via one or more of electrodes 24, 26 according to stimulation parameters values define by one or more therapy programs. The stimulation therapy delivered to brain 28 of patient 12 during the on cycle may influence the bioelectrical brain signals within one or more regions of the brain 28. For example, as shown in FIGS. 7A and 7B, cortical activity (e.g., within the AN or HC) may be suppressed by delivery of electrical stimulation to one or more regions of brain 28 (e.g., to the AN or the HC) relative to baseline cortical activity exhibited prior to delivery of electrical stimulation therapy.

Following delivery of electrical stimulation to brain 28 of patient 12 for at least one on cycle (106), processor 60 controls sensing module 66 may sense one or more brain signals via sensing module 66 (108). By sensing the brain signals immediately after the termination of the at least one on cycle, processor 60 may monitor one or more characteristics of the bioelectrical brain signal to determine when the sensed brain signals indicates that the brain state of patient 12 has returned to a baseline brain state (110). Processor 60 may determine that the brain state of patient 12 has returned to the baseline brain state by comparing one or more characteristics of the sensed brain signals to one or more characteristics stored in memory 62 as indicative of the baseline brain state. If processor 60 determines that the brain state of patient has not returned to the baseline brain state, e.g., because the sensed brain signal does not exhibit the characteristics indicative of the baseline brain state, processor 60 may continue to monitor the brain signal of patient via sensing module 66 (108).

On the other hand, if processor 60 determines that the sensed brain signal indicates that the brain state of patient 12 has returned to the baseline brain state (110), then processor 60 determines the washout period associated with the electrical stimulation delivered during the at least one on cycle (112). For example, processor 60 may determine the washout period by determining the length of time between the end of the at least one on cycle and when the sensed brain signal indicated that the brain state of patient 12 had returned to the baseline state. At a later time, after determining the washout period, processor 60 controls control delivery of electrical stimulation therapy to brain 28 of patient 12 based on the determined washout period (114). For example, processor 60 can control stimulation generator 64 to generate and deliver therapy to brain 28 of patient 12 prior to the brain state of patient returning to the baseline state during subsequent therapy cycles. In some examples, as described in further detail below with respect to FIG. 15, processor 60 controls stimulation therapy in this manner by selecting an off cycle duration based on the washout period (e.g., selecting the off cycle duration to be less than the washout period duration). In other examples, processor 60 controls stimulation therapy in this manner by controlling sensing module 66 to continuously sense a brain signal of patient 12 or sense the brain signal at regular intervals, and using a termination of the washout period or some smaller duration thereof to trigger therapy delivery by stimulation generator 64 in a pseudo closed loop manner.

Processor 60 can determine the washout period after delivery of therapy to brain 28 during a single on cycle or multiple on cycles. In some examples, processor 60 may repeatedly deliver stimulation for a selected on cycle to brain 28 and determine the washout period after each on cycle based on the monitored brain signal. Processor 60 may then determine that washout period for the selected on cycle duration as the average or median of duration of each washout period.

Further details regarding washout periods, carryover effects, and techniques for determining and monitoring the same are described in U.S. Patent Application Publication No. 2006/0264957 by Giftakis et al., entitled, "ANALYZING A WASHOUT PERIOD CHARACTERISTIC FOR PSYCHIATRIC DISORDER THERAPY DELIVERY" and filed on Apr. 17, 2009, which is hereby incorporated by reference in its entirety.

Figure 15:
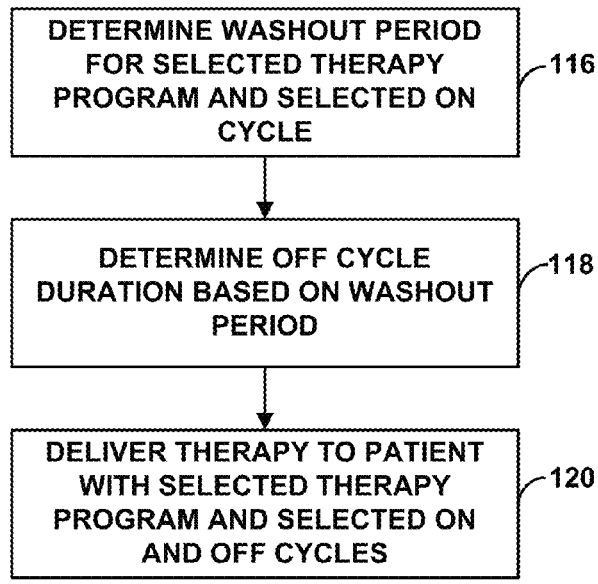
FIG. 15 is a flow diagram illustrating an example technique for selecting an off cycle duration for therapy.

FIG. 15 is a flow diagram illustrating an example technique for selecting the off cycle duration for a therapy delivered on according to a therapy cycle comprising a repeating pattern of on cycles and off cycles. As shown in FIG. 15, processor 60 determines the washout period for a selected therapy program and a selected on cycle duration (116), e.g., using the same or substantially similar process shown in FIG. 14. After determining the washout period for the therapy delivered according to the selected therapy program and on cycle, processor 60 determines the off cycle duration based on the determined washout period (118). For example, processor 60 may select an off cycle duration for the selected therapy program and on cycle duration such that the off cycle terminates and the subsequent on cycle begins at the end of the washout period, e.g., the off cycle duration may be substantially the same duration as that of the washout period. In some examples, memory 62 of IMD 16 or memory 82 of programmer 14 may store a minimum off cycle duration threshold, which may define the minimum off cycle duration for efficacious therapy delivery to patient 12. Processor 60 may, therefore, in some examples, be constricted to adjusting or selecting the off cycle duration to a value greater than or equal to the minimum off cycle duration threshold.

In some examples, processor 60 may select an off cycle duration that is less than that the duration of the washout period determined for the selected therapy program and the selected on cycle duration (116). For example, in some cases, it may be desirable to time therapy delivery to brain 28 such that the brain state does not revert to the baseline brain state (e.g., which may occur at the end of the washout period) or even a brain state within some threshold range of the baseline brain state after delivery of stimulation during the on cycle of therapy. In such examples, processor 60 may select an off cycle duration that is less than that of the washout period. For example, processor 60 may be configured to select an off cycle duration that is a preprogrammed percentage of the washout period, (e.g., approximately 50% to about 90% of the washout period). This may also allow the selected off cycle duration to include a built in buffer to account for natural variation in the washout period following respective on cycles for a particular therapy program. Because patient physiology (e.g., hydration level) is constantly changing, the effects of therapy delivery according to a particular therapy program can change over time or depending on the time of day.

In other examples, processor 60 may select an off cycle duration that is greater than that of the washout period determined for the selected therapy program and on cycle duration (116). For example, in some cases, therapeutic effects may be maintained even if the brain state of patient 12 returns to the baseline brain state after an on cycle, e.g., for some nominal period of time, before being modified by the delivery of stimulation to brain 28 by delivery of electrical stimulation during the subsequent on cycle. In such cases, processor 60 may identify an off cycle duration substantially equal to the washout period plus the amount of time that patient 12 may be at the baseline brain state while maintaining effective treatment of the patient condition.

In some examples, processor 60 may select the off cycle duration at least in part of input provided by a user. For example, during a programming session, processor 60 can communicate the washout period determined for the selected therapy program and selected on cycle and/or temporal information related to the monitored brain signal to programmer 14. Programmer 14 may present the information to a clinician, e.g., via user interface 68 (FIG. 4), and the clinician may select an off cycle duration based on a review the information regarding the washout period and/or brain signal information. The clinician may communicate the off cycle duration to processor 60 of IMD 16 via programmer 14. In view of the input received from the clinician, processor 60 may determine the off cycle duration and store the determined duration in operating instructions 78 of memory 62 (FIG. 3).

In some examples, processor 60 or processor 80 (FIG. 4) may be configured to determine the washout period for the selected therapy program and then determine one or more suggested off cycle durations based on the washout period. The one or more suggested washout periods may then be presented to a user for approval and/or selection via programmer 14 (FIG. 3). Processor 60 may then determine the off cycle duration in view of the input received from the user.

Once the off cycle duration has been determined, processor 60 may control stimulation generator 64 to generate and deliver the cycled therapy according to the selected therapy program and the selected on and off cycle durations (120). For example, when IMD 16 is active for therapy delivery, processor 60 may control stimulation generator 64 (FIG. 3) to generate and deliver stimulation to brain 28 via at least one of electrodes 24, 26 according to the selected therapy program for the selected on cycle duration, and then temporarily suspend delivery of stimulation during the following off cycle having a duration determined as described above with respect to FIG. 15. IMD 16 may resume stimulation during the subsequent on cycle that begins at the end of the off cycle.

The example technique shown in FIG. 15 may be used during a programming session to determine the off cycle duration appropriate for the particular therapy program and on cycle duration selected for the delivered therapy. Alternatively or additionally, the example process of FIG. 15 may be used periodically or continuously during the delivery of chronic therapy to patient 12 to update a previously selected off cycle duration for the therapy delivered by IMD 16 to brain 28. As described in further detail below, specific on cycle durations, as well as on cycle duration, may be determined for a selected therapy program. Additionally, unique therapy cycle parameters may be determined for each of a plurality of therapy programs rather than using a single set of therapy cycle parameters (e.g., on cycle duration, off cycle duration) for more than one therapy program that is stored by IMD 16.

Figure 16:
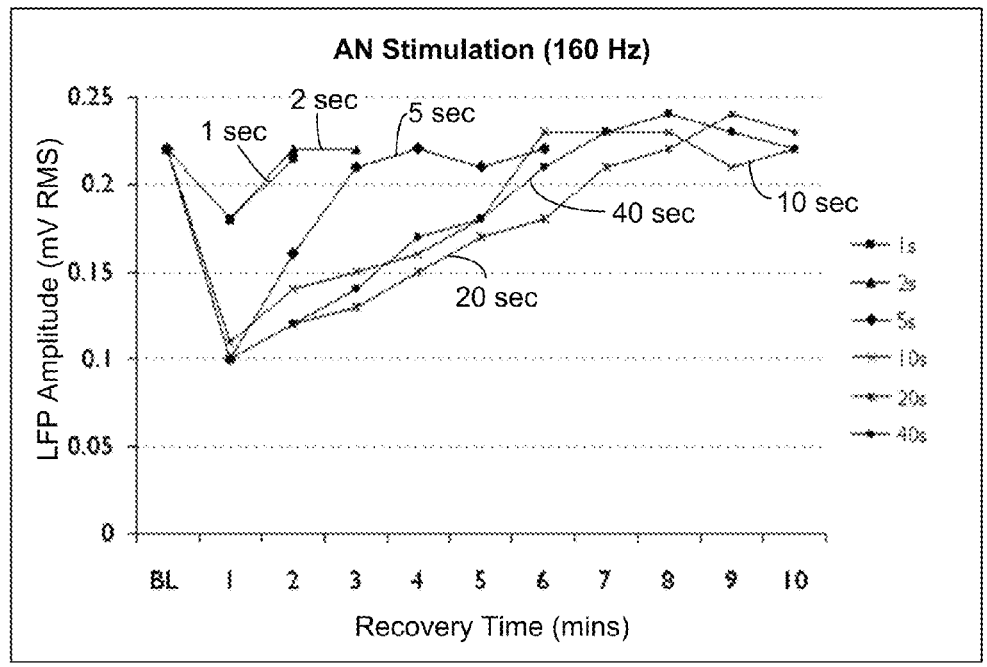
FIG. 16 is a plot illustrating example temporal effects on cortical activity in the hippocampus region of an ovine subject from example stimulation of the anterior thalamic nucleus region.

FIG. 16 is a plot illustrating example temporal effects on cortical activity in the HC of an ovine subject from delivery of stimulation to the AN of the ovine subject. In particular, the plot of FIG. 16 shows cortical activity in terms of root mean square (RMS) amplitude value for the LFP measured in the HC versus time during an off cycle (referred to in FIG. 16 as "Recovery Time") directly following delivery of electrical stimulation having a pulse frequency of approximately 160 Hz. In the example, the stimulation had a pulse width of approximately 120 microseconds and a pulse amplitude of approximately 10 volts. The electrical stimulation was delivered to the AN of the ovine subject for various on cycle durations. Specifically, as labeled in FIG. 16, the electrical stimulation was delivered to the AN in a single burst for about 2 seconds, about 5 seconds, about 10 seconds, about 20 seconds, and 40 seconds. Thus, the on cycle durations were about 2 seconds, about 5 seconds, about 10 seconds, about 20 seconds, and 40 second, respectively.

As shown in FIG. 16, the effects on brain activity (and, therefore, in some cases, brain state) from the delivery of stimulation may depend on the on cycle duration. For each of the on cycle durations trialed on the ovine subject, the therapy delivery reduced the RMS of LFP amplitude in the HC from the baseline amount of approximately 0.22 millivolts (mV). However, the washout period as well as the carryover effects on the cortical activity during the washout period, varied for each on cycle condition. For example, while an on cycle durations of about 5, 10, 20, and 40 seconds produced approximately the same maximum suppression of LFP amplitude in the HC (i.e., which indicate at least part of the carryover effect from the stimulation delivery), the washout period was different for each on cycle.

The results shown in FIG. 16 suggest that the duration of an off cycle for stimulation delivered for each of a plurality of on cycle durations may be different for each on cycle based on the differences in carryover effects and washout period for each on cycle. As such, it can be useful to select both on and off cycle durations a specific therapy program in order to select efficacious therapy cycle parameters.

Figure 17:
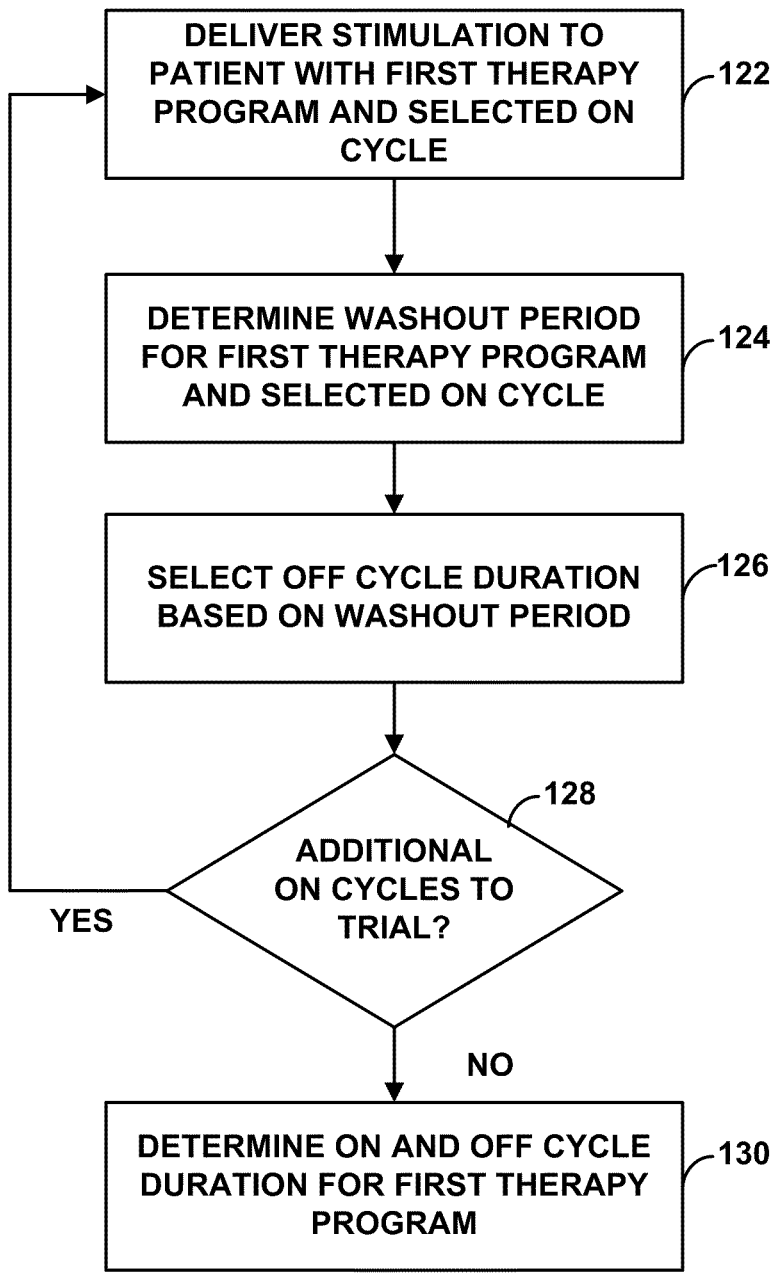
FIG. 17 is a flow diagram illustrating an example technique for selecting cycle parameters for a therapy program.

FIG. 17 is a flow diagram illustrating an example technique for selecting cycle timing parameters for a therapy program. The example technique may be used by a clinician during a programming session to trial a therapy program with various on cycle durations. For each on cycle trialed for the therapy program, an off cycle duration may be selected. A clinician may evaluate each of the on cycle/off cycle combinations selected for the therapy program, and may select the therapy cycle parameters to be used for chronic delivery of therapy.

As shown in FIG. 17, during a programming session, processor 60 can control stimulation generator 64 to generate and deliver electrical stimulation to brain 28 of patient 12 via at least one of electrodes 24, 26 according to a first therapy program and selected on cycle duration (122). As described above, the first therapy program may define stimulation parameter values, such as, e.g., a pulse rate value, a pulse amplitude value, and a pulse width value for stimulation delivered to brain 28 in the form of electrical stimulation pulses. Following the delivery of stimulation to brain 28 according to the first therapy program for a selected on cycle duration, processor 60 may determine the washout period for the first therapy program and selected on cycle (124). The washout period for the stimulation may be determined based on brain signals of patient 12 monitored via sensing module 64 of IMD 16, e.g., as described above with regard to FIG. 15. Based on the determined washout period, processor 60 may select an off cycle duration for the first therapy program and selected on cycle duration, e.g., as described with regard to FIG. 16 (126).

If there are additional on cycle durations to trial (128), processor 60 can repeat the process to determine the off cycle durations for each of the additional on cycle durations. In this manner, as the washout period and carryover effects may vary based on the on cycle duration for a therapy program defined by the first therapy program, an off cycle duration may be selected for each particular on cycle duration trialed during the programming session. Once the desired number of the on cycle durations are trialed, a user and/or processor 60 of IMD 16 may determine the on cycle and off cycle duration for the first therapy program by evaluating the plurality of different on cycle and off cycle combinations determined for each trialed on cycle.

Figure 18:
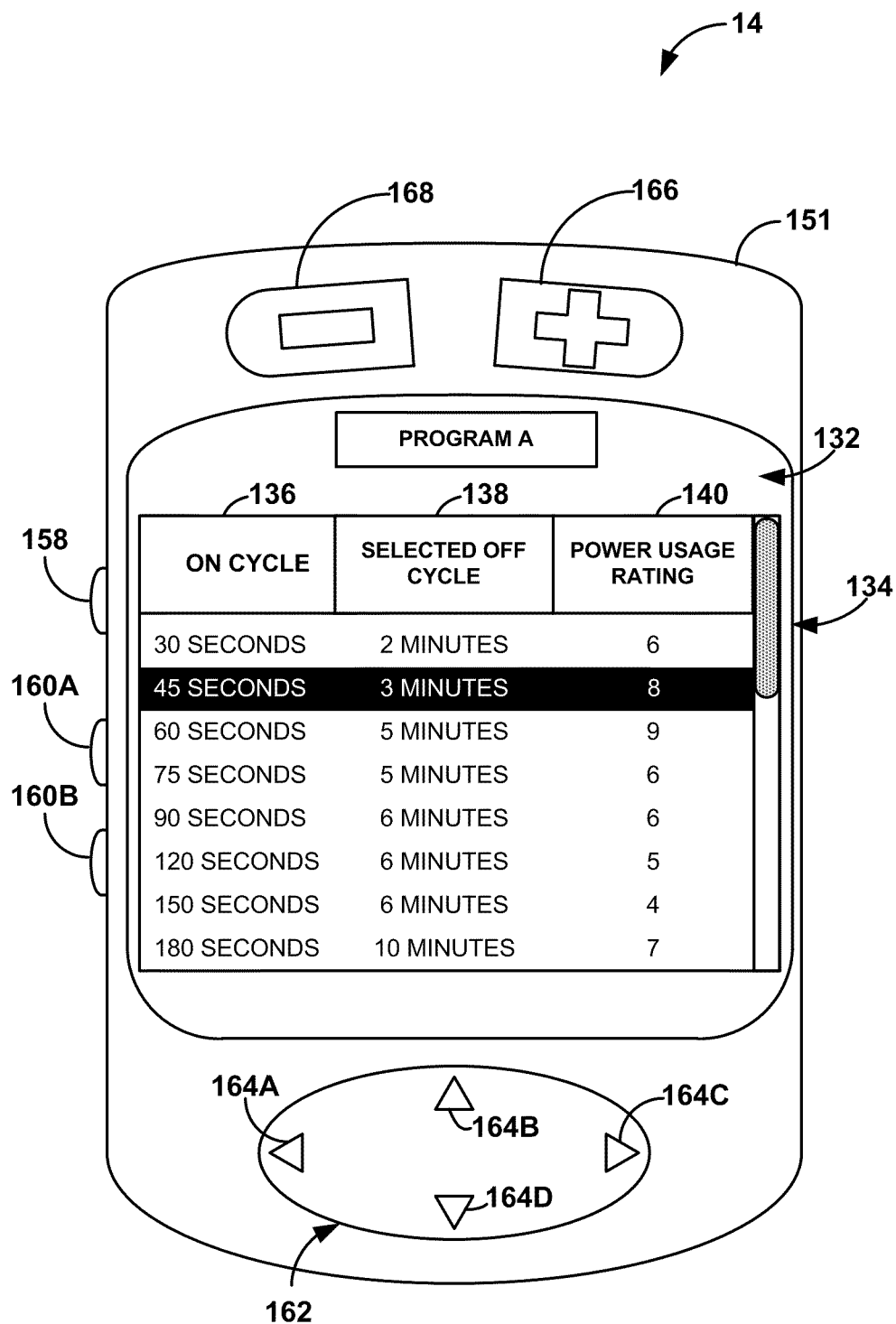
FIG. 18 is a schematic illustration of an example medical device programmer, which includes a display presenting a graphical user interface (GUI) with a list of example therapy cycle parameters for an example therapy program.

For example, after trialing a plurality of on cycle durations for a therapy program and selecting off cycle durations for each of the on cycle durations, a clinician, with the aid of programmer 14 or another computing device, may review and, e.g., order the list of on cycles trialed based on various parameters, such as a duration of the off cycle selected for the specific on cycle or a power usage rating associated with the on cycle/off cycle combination. FIG. 18 is a schematic illustration of programmer 14, which illustrates a graphical user interface (GUI) 132 presented on display 134 of programmer 14. GUI 132 includes a list of on cycles 136 tested during a programming session, which are designated by duration, along with off cycle durations 138 selected for each of the on cycles and power usage rating 140.

The power usage rating 140 may be considered an evaluation metric of the respective therapy cycle parameters, as well as therapy programs. Power using rating 140 may reflect a rating of the IMD 16 power usage when delivering therapy according to particular therapy program for given therapy cycle parameter value (e.g., on cycle and off cycle duration). For example, IMD 16 may consume more energy when generating and delivering electrical stimulation therapy according to a first therapy program for first on cycle/off cycle combination versus another on cycle/off cycle combination. Moreover the energy consumed by IMD 16 may also vary based on the therapy program defining the stimulation during an on cycle. The energy associated with each therapy program and therapy cycle parameter values may be calculated as product of the power required to generate the stimulation signals defined by the therapy program and the duration of the stimulation signal. The power required to generate the stimulation signal may generally be a product of the voltage and current needed to generate the stimulation signal. Therefore, an energy associated with a stimulation signal may be a direct function of voltage, current, and duration of the stimulation signal.

In examples in which IMD 16 is implanted within patient 12 for chronic therapy delivery, it may be desirable to minimize power consumption in order to extend the useful life of IMD 16 or minimize time between recharging of power source 36 (FIG. 2). Accordingly, the clinician may evaluate the tested therapy programs based on the respective power usages. The power usage may be, for example, rated on a numerical scale, where the lower power consumption therapy programs are provided with a higher energy efficiency rating. For example, the power usage rating presented by display 134 in the example of FIG. 18 is a numerical rating on a scale from 1 to 10, where a rating of "10" indicates a lower power usage (e.g., more power efficient) than a rating of "1." However, other types of scales are possible, and are not limited to a numerical scale or a numerical 1-10 scale.

The off cycle duration shown on display 134 in FIG. 18 is the duration of the off cycle selected for the associate on cycle duration. In other examples, programmer 14 may display other washout period or carryover effect characteristics measured for each on cycle trialed. For example, programmer 14 may display the maximum difference from a baseline brain signal for one or more brain signal characteristics during the washout period for each on cycle. In other examples, programmer 14 may display the variability of the brain signal during the washout period. In one example, the programmer 14 may display the maximum and/or average suppression of cortical activity during the washout period for each on cycle.

In addition to a washout period characteristic, in some examples, the clinician may evaluate the tested on cycles based on one or more stimulation period characteristics. The stimulation period characteristic may include a characteristic of the brain signal during the on cycle. For example, the stimulation period characteristic may include the peak, average or median amplitude of the brain signal during the on cycle, or the duration that changes to the signal from the baseline state were observed. Other physiological parameters (e.g., intracranial pressure, blood pressure, heart rate, body temperature, respiration rate, muscle activity, and the like) that are affected by stimulation delivery to brain 28 can also be used to compare the different on cycle and off cycle pairings. Therapy system 10 can include physiological sensors that sense the other physiological sensors, whereby the other physiological sensors can be incorporated with IMD 16 or physically separated from outer housing 34 and separately implanted within patient 12. Examples of other physiological parameters are described in commonly-assigned U.S. patent application Ser. No. 12/359,055 by Giftakis et al., entitled, "SEIZURE DISORDER EVALUATION BASED ON INTRACRANIAL PRESSURE AND PATIENT MOTION" and filed on Jan. 23, 2009, and U.S. Patent Application Publication No. 2006/0264957 by Giftakis et al., entitled, "ANALYZING A WASHOUT PERIOD CHARACTERISTIC FOR PSYCHIATRIC DISORDER THERAPY DELIVERY" and filed on Apr. 17, 2009, which are hereby incorporated by reference in their entireties.

In other examples, the clinician may evaluate tested therapy programs based on subjective metrics, such as a rating of the therapy delivered according to the selected cycle parameter values indicated by patient 12 in response to therapy delivery according to each on cycle and subsequent off cycle, which may be delivered for one or a plurality of therapy cycles. Patient 12 may directly provide input to programmer 14 regarding these other evaluation metrics via user interface 86 (FIG. 4) or may provide input to the clinician or another user, who may then input the information to programmer 14 or another computing device. The rating provided by patient 12 regarding the efficacy of the therapy may be a numerical rating, a sliding scale or any suitable type of rating system. In the case of Alzheimer's disease, patient 12 may provide a subjective rating of memory loss following therapy delivery by according to a selected therapy cycle parameters.

In some examples, a clinician may also evaluate tested on cycle/off cycle duration combinations based on side effects resulting from therapy delivery according to the respective cycle parameters. Side effect information that may be collected for each therapy program may include, for example, the type, duration or severity of the side effects observed during the on cycle and/or off cycle, as well as the time that the side effects became evident to patient 12. In some examples, patient 12 may provide input indicating a numerical rating of the side effects, where a higher numerical rating number indicates a relatively more severe side effect. Other techniques for rating the side effects for the trialed conditions are contemplated. In some examples, using this technique, the clinician may determine whether a specific therapy program causes a cortical change of a certain magnitude, which is associated with an adverse event. Testing at certain stimulation frequencies, voltage levels, and/or pulse widths may result in either too much cortical suppression or too much cortical excitability. As a result, the clinician may choose to treat the patient differently, based on such knowledge. For example, the clinician may choose a therapy program that produces a desired amount of cortical suppression (e.g., 60% cortical activity suppression), which may be effective for treating a seizure disorder but does not result in side effects, such as memory impairment or depression, which may occur at much higher levels of cortical suppression (e.g., 90-100%).

In some cases, an overall evaluation metric may be generated for each trialed therapy cycle condition, where the specific evaluation metrics, such as the power usage rating, washout period characteristic, carryover period characteristic, stimulation period characteristic, a patient efficacy rating and/or side effect metric are weighted according to their relative importance to the therapy evaluation. For example, the clinician may determine that the power usage metric should have twice the weight as the efficacy rating, due to the subjective nature of the efficacy rating and the relatively objective nature of the power usage metric.

In view of the therapy cycle parameters and/or evaluation metrics (e.g., power usage rating), a clinician or processor 80 of programmer 14 (or another device) may determine the desired on cycle and off cycle duration for therapy delivered according to the first therapy program (130) (FIG. 17). The determined on cycle and off cycle duration combination may be stored in operating instructions 78 of memory 62 (FIG. 3) of IMD 16 for use when processor 60 controls delivery of therapy to brain 28 of patient 12 according to the first therapy program. In addition, in some examples, the various on cycle/off cycle duration combinations may be stored in memory 64 of programmer 14 for access in the future. For example, if patient 12 determines that delivery of the first therapy according to the determined on cycle and off cycle durations do not provide effective therapy, then clinician may access the other on cycle/off cycle durations determined for the first therapy program during the trialing session to change the therapy cycle parameters of the first therapy program.

The examples process of FIG. 17 may be repeated for a plurality of therapy programs to determine therapy cycle parameter values (e.g., on cycle duration and off cycle duration) for each of the plurality of therapy programs. Once the desired number the therapy programs are trialed and therapy cycle durations are selected for each, a user and/or processor 60 of IMD 16 may evaluate the plurality therapy programs.

Figure 19:
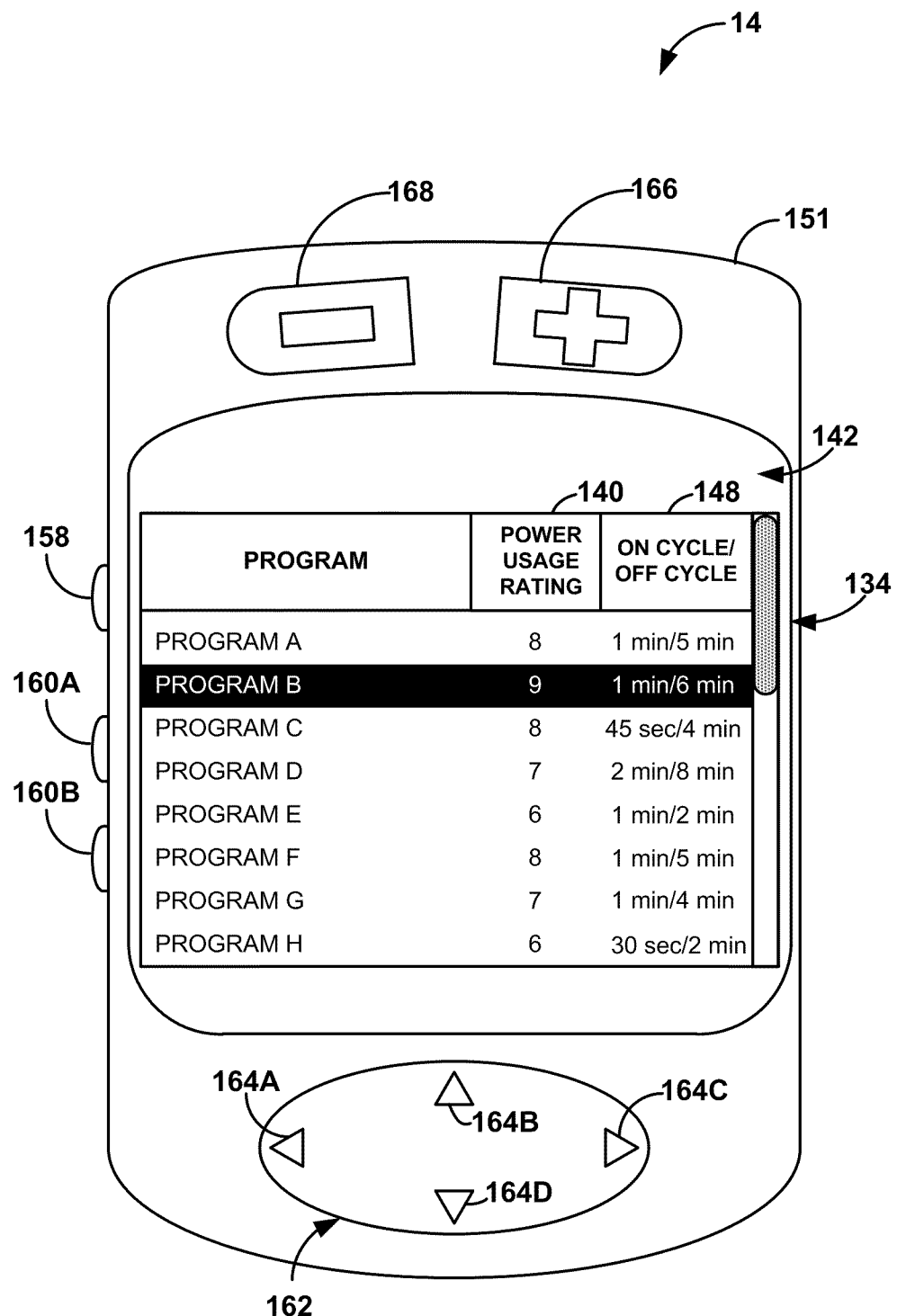
FIG. 19 is a schematic illustration of an example medical device programmer, which includes a display presenting a GUI with a list of therapy programs.

For example, after trialing a plurality of therapy programs, a clinician, with the aid of programmer 14, may order the list of programs trialed based on the therapy cycle parameters and/or other evaluation characteristics (e.g., power usage rating). FIG. 19 is a schematic illustration of programmer 14, which illustrates a GUI 142 presented on display 134 of programmer 14. GUI 142 includes a list of therapy programs tested during a programming session, along with selected on cycle/off cycle durations 1480 and power usage rating 140. GUI 142 may also include one or more evaluation characteristics previously described with regard to evaluation of different on cycle/off cycle combinations associated with a first therapy program.

Figure 25:
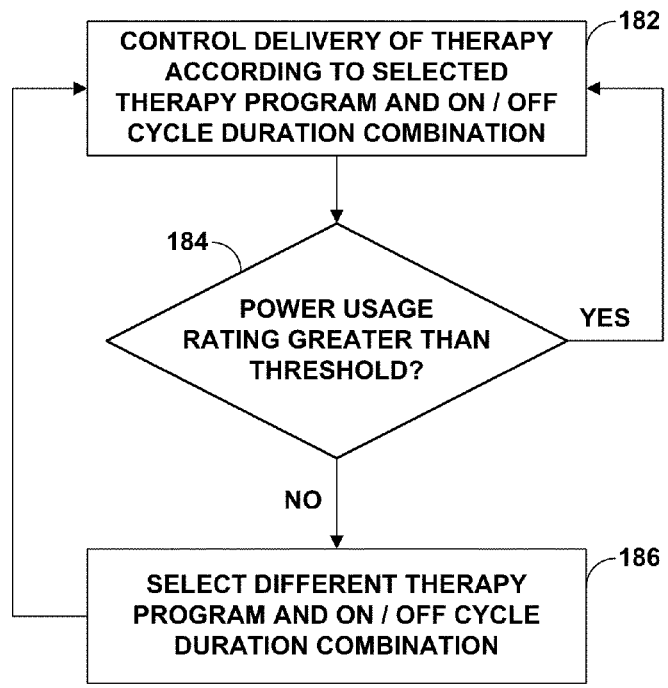
FIGS. 25 and 26 are flow diagrams illustrating example techniques for controlling delivery of therapy to a patient.

A clinician may evaluate each available therapy program to determine one or more therapy programs to use for chronic therapy delivery to treat a patient disorder. In some examples, a clinician may select therapy program(s) based on power efficiency, e.g., as reflected in the power usage rating for each program. If the effectiveness of each of therapy program varies amongst the different therapy programs, a clinician may select the therapy program with the preferred combination of power usage rating and therapeutic effectiveness. Alternatively or additionally, a clinician may select a therapy program based on the duration of either or both of the on cycle duration and off cycle duration selected for each therapy program. While examples of the disclosure are described with regard to clinician selection of therapy cycle parameters and therapy programs, in some examples, processor 60 of IMD 16 or processor 80 of programmer 14 may be configured to automatically or semi-automatically select one or more therapy cycle parameters and/or therapy programs based on one or more suitable evaluation metrics. As described below, FIG. 25 illustrates an example technique in which processor 60 and/or processor 80 may periodically or continuously evaluate a therapy program that is delivered to a patient using one or more evaluation metrics, and, in some examples, select a new therapy program for delivery to patient 12 based on the evaluation metrics associated with the therapy program currently being delivered to the patient, e.g., when such evaluation metrics indicate that one or more aspects of the present therapy program are not efficacious.

To evaluate the plurality of therapy programs, processor 80 of programmer 14 may receive input from the clinician or another user selecting one of the evaluation metric types with which to order the list of therapy programs. For example, display 134 may be a touch screen display, and the clinician may select power usage rating box 140, and processor 80 may order the list of therapy programs according to evaluation metric associated with the selected text box. In some cases, the clinician may wish to maximize the duration of the off cycle. The clinician may determine which therapy program resulted in the longest off cycle duration by ordering the list of therapy programs according to the off cycle duration.

Programmer 14 includes housing 151, power button 158, contrast buttons 160A, 160B, control pad 162 with directional buttons 164A, 164B, 164C, and 164D, increase button 166, and decrease button 168. Housing 151 may substantially enclose the components of programmer 14, such as processor 80 and memory 82. A user may depress power button 158 to turn programmer 14 on or off. Programmer 14 may include safety features to prevent programmer 14 from shutting down during a telemetry session with IMD 16 or another device in order to prevent the loss of transmitted data or the stalling of normal operation. Alternatively, programmer 14 and IMD 16 may include instructions for handling possible unplanned telemetry interruption, such as battery failure or inadvertent device shutdown.

Display 134 may be a liquid crystal display (LCD), touch screen display, or another type of monochrome or color display capable of presenting information to a user, e.g., a clinician. Contrast buttons 160A, 160B may be used to control the contrast of display 134. In addition to displaying a list of trialed therapy programs, selected on/off cycle durations and associated evaluation metrics (e.g., power usage rating), processor 80 of programmer 14 may also present information regarding the type of IMD 16, operational status of IMD 16, patient data, and operational status of programmer 14 on display 134.

Control pad 162 allows the user to navigate through items presented on display 134. For example, the clinician may press control pad 162 on any of arrows 164A-164D in order to move between items presented on display 134 or move to another screen not currently shown by display 134. For example, the clinician may depress or otherwise activate arrows 164A, 164C to navigate between screens of GUI 142, and depress or otherwise activate arrows 164B, 164D to scroll through the therapy programs presented by GUI 142. The clinician may press the center portion of control pad 162 in order to select any highlighted element in GUI 142. For example, the clinician may scroll to and select the on cycle of "Program B" which is shown to be highlighted in FIG. 19, in order to receive more information about the therapy program, such as the stimulation parameter values defined by Program B. In other examples, scroll bars, a touch pad, scroll wheel, individual buttons, a stylus (in combination with a touch screen display 134) or a joystick may perform the complete or partial function of control pad 162.

Increase button 166 and decrease button 168 provide input mechanisms for a user, such as clinician or patient 12. In general, depressing decrease button 168 one or more times may decrease the value of a highlighted therapy parameter and depressing increase button 166 one or more times may increase the value of a highlighted therapy parameter. While buttons 166, 168 may be used to control the value of any therapy parameter, the user may also utilize buttons 166, 168 to select or generate particular programs for testing during a therapy programming session. In addition, patient 12, the clinician or another user may utilize control pad 160, buttons 166, 168 or display 134 in examples in which display 134 comprises a touch screen to input information related to the efficacy of a therapy program or other evaluation metrics. Further, the clinician or another user may utilize control pad 162, buttons 166, 168 or display 134 in examples in which display 134 comprises a touch screen in order to input information related to the identification of patient brain state and/or washout period.

Programmer 14 may take other shapes or sizes not described herein. For example, programmer 14 may take the form of a clam-shell shape, similar to cellular phone designs. In any shape, programmer 14 may be capable of performing the requirements described herein. Furthermore, in other examples, the buttons of programmer 14 may perform different functions than the functions provided in FIGS. 18 and 19 as an example. In addition, other examples of programmer 14 may include different button layouts or number of buttons. For example, display 134 may be a touch screen that incorporates all user interface and user input mechanism functionality.

As described above, therapy system 10 may be configured to select at least one therapy cycle parameter, such as, e.g., on cycle duration and/or off cycle duration, based on bioelectrical brain signal(s) monitored, for example, via sensing module 66 of IMD 16. In some examples, the at least one therapy parameter value may be selected based on the washout period determined following at least one on cycle of therapy (e.g., as described for the examples of FIGS. 15 and 17). In this manner, as the washout period of therapy may vary based on the selected on cycle duration and/or therapy program, therapy cycle parameters specific to the behavior of a brain signal both during and following delivery of therapy according to particular therapy program may be selected.

In some examples, the at least one therapy cycle parameter may be selected during a programming session for one or more therapy programs to be used for chronic therapy to treat a patient disorder. Alternatively or additionally, processor 60 may be configured to automatically or semi-automatically adjust at least one therapy cycle parameters on a periodic or substantially continuous basis during chronic therapy delivery. In some examples, sensing module 66 of IMD 14 may monitor the brain signal of patient 12 via one or more of electrodes 24, 26, and processor 60 may adjust the therapy cycle parameters based on the brain state of patient 12 indicated by the monitored brain signal. For example, processor 60 may adjust the on cycle and/or off cycle duration of a therapy such that the therapy delivered to patient 12 by IMD 16 allows patient 12 to maintain a desired brain state.

As described above, in some examples, the effects of therapy delivery according to a particular therapy program may change over time. Moreover, in some examples, the efficacy of therapy delivered according to therapy program using particular therapy cycle parameters selected, for example, using one or more of the example techniques described herein, may change over time. For example, the duration of a washout period may change (e.g., increase or decrease) over time even thought processor 60 controls the therapy according to the same therapy program and selected therapy cycle parameters. In some cases, the physiological characteristics of tissue within brain 28 of patient 12 may change or the patient's underlying condition may progress or improve, which may affect the efficacy of therapy delivery.

To maintain therapeutic efficacy for therapy delivered on a chronic (e.g., non-temporary) basis, IMD 16 may be configured to adjust one or more therapy cycle parameters periodically over a period to time. For example, processor 60 and/or processor 80 may perform one or more of the example techniques described herein to select one or more therapy cycle parameters on a periodic basis to maintain effective treatment of the patient condition. Processor 60 and/or processor 80 may adjust one or more therapy cycle parameters in this manner on any suitable time basis, including, e.g., on an hourly, daily, weekly, and/or monthly basis. In this manner, system 10 may maintain effective treatment of a patient condition for therapy that is delivered to patient 12 on a cycled basis by periodically adjusting one or more therapy cycle parameters (e.g., on cycle duration and/or off cycle duration), e.g., to continuously adapt to physiological changes of patient 12 that may influence the effectiveness of the therapy over time.

Figure 20:
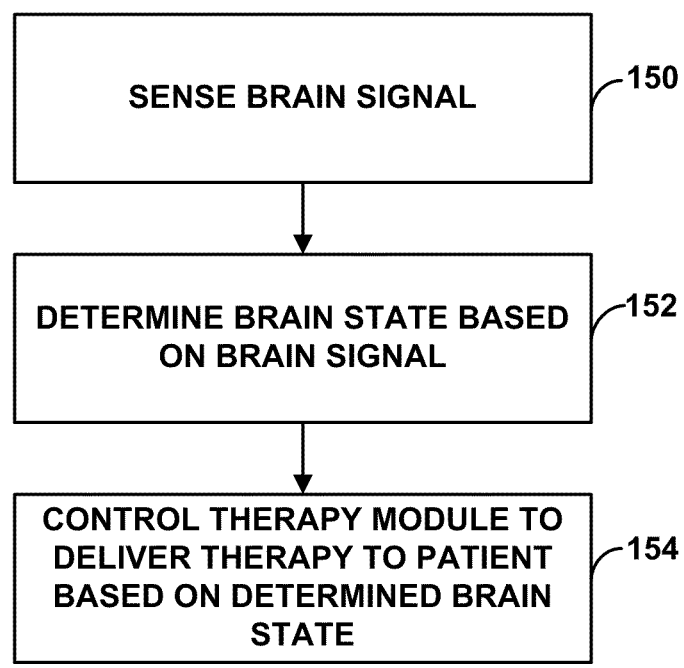
FIG. 20 is a flow diagram illustrating an example technique for controlling delivery of therapy to a patient.

FIG. 20 is a flow diagram illustrating an example technique for controlling delivery of therapy to a patient based on the brain state of patient 12. As described above, the brain state within one or more regions of brain 28 of patient 12 may be indicated by one or more characteristics of the brain signal sensed by sensing module 66 via at least one of electrodes 24, 26. One or more desirable brain states may be defined based one more characteristics of a brain signal associated with effective treatment of the patient disorder. For example, in the case of a seizure disorder, different brain states of brain 28 may be defined by the amount of cortical activity within one or more regions (e.g., AN or HC) of brain 28. A desired or target brain state may be defined by a brain signal indicating suppressed cortical activity from a baseline cortical activity value measured prior to the delivery of stimulation to brain 28.

As shown in FIG. 20, sensing module 66 of IMD 16 senses the brain signal within one or more regions of brain 28 via at least one of electrodes 24, 26 (150). Based on the brain signal sensed by sensing module 66, processor 60 determines the brain state of patient 12 (152). As described above, one or more characteristics of a brain signals, such as, e.g., time domain characteristics (e.g., an average, peak, mean or instantaneous amplitude) or a frequency domain characteristic (e.g., an energy level in one or more frequency bands), sensed by sensing module 66 may be used to characterize the brain state of patient 12. Indicators of particular brain states may be stored within brain state information 76 of memory 62 (FIG. 3). To determine the current brain state of patient 12, processor 60 may compare the sensed brain signal to the brain state information to determine brain state of patient 12 indicated by a sensed brain signal.

After determining the brain state of patient 12 indicated by the sensed brain signal, processor 60 may control the therapy module to deliver therapy to brain 28 of patient 12 based on the determined brain state (154). For example, if IMD 16 is not delivering stimulation therapy to brain 28, processor 60 may control stimulation generator 64 of the therapy module by begin delivering therapy to brain 28 of patient 12, for example, to change the brain state of patient 12 from an undesired brain state to a desired brain state.

The therapy delivered by IMD 16 may be delivered to brain 28 according to one or more therapy programs stored in memory 62 (FIG. 3) of IMD 16. Processor 60 can select the therapy program based on the brain state determined from the sensed brain signal. For example, processor 60 can select a therapy program configured to treat the particular brain state of patient determined from the brain signal. In some examples, therapy programs can be associated with predetermined brain states (e.g., predetermined brain signal characteristics) in memory 62 of IMD 16 or a memory of another device, and processor 60 can select the therapy program based on the determined brain state. In some examples, processor 60 may control delivery of therapy to patient 12 by adjusting one or more stimulation therapy parameter values, e.g., by changing therapy programs and/or adjusting one or more values defined by a therapy program. In some examples, instructions for adjusting a therapy program can be associated with predetermined brain states (e.g., predetermined brain signal characteristics) in memory 62 of IMD 16 or a memory of another device, and processor 60 can adjust one or more therapy parameter values based on the determined brain state and associated instructions. In other examples, processor 60 may control delivery of therapy to brain 28 based on the determined brain state of patient 12 by terminating or suspending the delivery of therapy being delivered to brain 28 by stimulation generator 64.

In the case of cycled therapy, if processor 60 determines that the brain state of patient 12 is an undesirable brain state during an off cycle, processor 60 may control stimulation generator 64 to generate and deliver electrical stimulation to brain 28 of patient 12 via electrodes 24, 26, e.g., by ending the off cycle, to change the brain state of patient 12 as a result of the electrical stimulation. This may, for example, restart a therapy cycle in the middle of an off cycle. Once the sensed brain signal indicates a desirable brain state of patient 12, processor 60 may control stimulation generator 64 to suspend delivery of electrical stimulation to brain 28, e.g., by adjusting the on cycle duration. In this manner, processor 60 may select or adjust one or more therapy cycle parameters of therapy based on the brain state of patient 12 determined from the sensed brain signal. Processor 60 may continue to control the delivery of therapy according to the new on cycle/off cycle duration combination, e.g., until processor 60 adjusts such parameters again using the example technique of FIG. 20.

Figure 21:
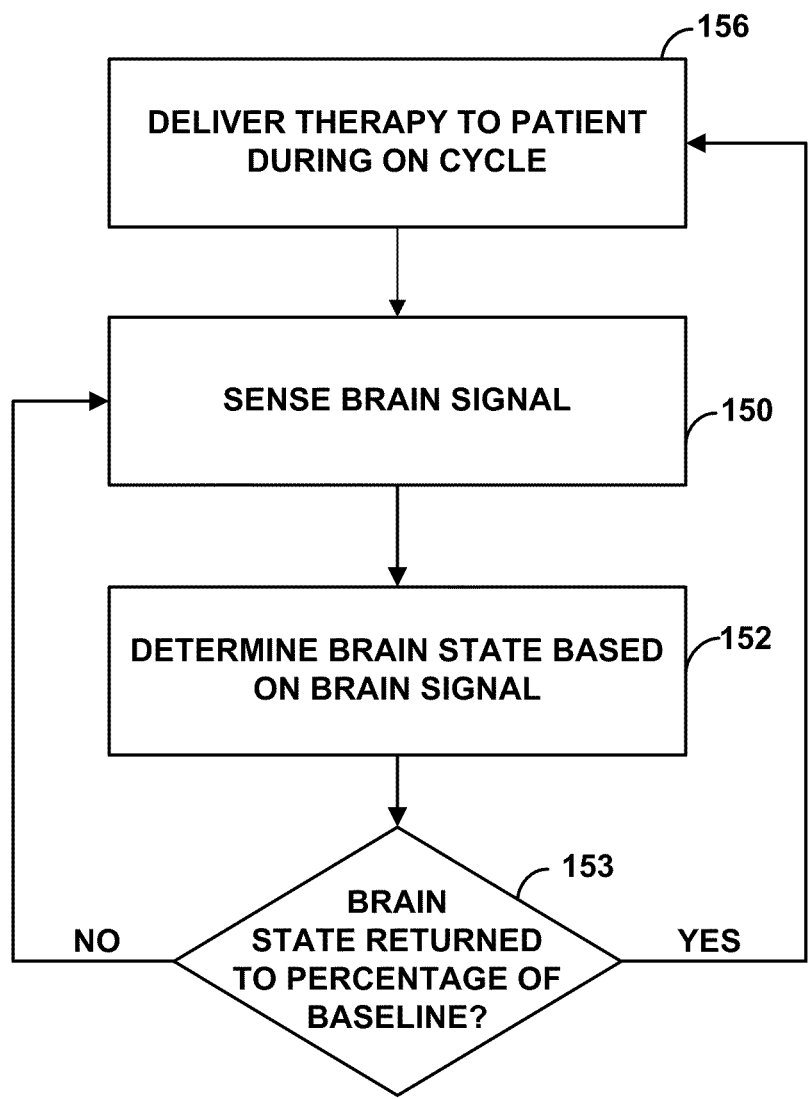
FIG. 21 is a flow diagram illustrating an example technique for controlling delivery of therapy to a patient.

FIG. 21 is a flow diagram illustrating an another example technique for controlling delivery of therapy from IMD 16 to patient 12 based on the brain state of patient 12. The example technique may be used to provide therapy to patient 12 on a cycled basis, where the therapy cycle parameters are selected based on the brain state of patient 12. For purposes of illustration, the example of FIG. 21 is described for cases in which the brain state of patient 12 is defined based on the cortical activity derived from the brain signal sensed via sensing module 66 (FIG. 3). However, other examples, including those in which the brain state of is determined by a characteristic of a brain signal other than that of cortical activity, are contemplated.

As shown in FIG. 21, during an on cycle of the therapy cycle, processor 60 controls stimulation generator 64 to generate and deliver electrical stimulation to brain 28 via one more of electrodes 24, 26 (156). Processor 60 may control stimulation generator 64 to generate and delivery electrical stimulation to brain 28 according to one or more therapy programs defining stimulation parameter values. In some examples, such as when patient 12 has a seizure disorder, the stimulation delivered to brain 28 from IMD 16 during the on cycle can be configured to suppress cortical activity within one or more regions of brain 28 from a baseline amount of cortical activity, e.g., in a manner similar to that shown for some stimulation frequency values in FIGS. 10 and 16. In other examples, such as when patient 12 as Alzheimer's disease or another form of dementia, the stimulation delivered to brain 28 of patient 12 may be configured to increase the cortical activity from a baseline amount of cortical activity. The on cycle duration may be selected such that the stimulation delivered from IMD 16 to brain 28 results in a desired level of cortical activity.

Processor 60 controls sensing module 66 to sense the brain signal of patient 12 (150) following delivery of stimulation to brain 28 during the on cycle (156). As described above, sensing module 66 may be configured to sense brains signals from one or more regions of brain 28. In some examples, sensing module 66 may sense a brain signal from the substantially the same region of brain 28 that stimulation generator 64 delivers electrical stimulation during an on cycle. For example, sensing module 66 may sense a brain signal from the HC when stimulation generator 64 delivers electrical stimulation to the HC, or may sense a brain signal from the AN when stimulation generator 64 delivers electrical stimulation to the AN. Alternatively or additionally, sensing module 66 may sense a brain signal from one or more regions different than the stimulation region. For example, sensing module 66 sensing module 66 may sense a brain signal from the HC when stimulation generator 64 delivers electrical stimulation to the AN, or may sense a brain signal from the AN when stimulation generator 64 delivers electrical stimulation to the HC.

In some examples, sensing module 66 senses a brain signal from a region within the same neurological pathway (e.g., the Circuit of Papez) as the stimulation region of brain 28. For example, sensing module 66 may be configured to sense a brain signal from the HC of brain 28 via one or more implanted sense electrodes and stimulation generator 64 may be configured to deliver electrical stimulation to the AN of brain 28 via one or more of electrodes 24, 26. Alternatively, sensing module 66 and stimulation generator 64 may sense brain signals and deliver electrical stimulation, respectively, to the AN of brain 28, for example, as the brain signal in the AN may correlate to the cortical activity within the HC. Other stimulation and sensing regions of brain 28 are contemplated. In one example, stimulation generator 64 may be configured to deliver electrical stimulation to the formix, which also forms part of the Circuit of Papez, and has neural connections to the HC.

Based on the brain signal sensed by sensing module 66 following the therapy on cycle (150), processor 60 determines the brain state of patient 12 (152). Processor 60 then determines whether or not the brain state of patient 12 has returned to within a threshold percentage of a baseline brain state (153). For example, processor 60 may compare the cortical activity from the sensed brain signal to the cortical activity associated with the baseline brain state to determine the percent difference, e.g., increase or decrease, of the sensed and baseline value. The threshold percentage may be a preprogrammed value stored in memory 62 of IMD 16.

If the percentage difference between the cortical activity of the determined and baseline brain state is not within the threshold percentage, processor 60 may continue to sense the brain signal of patient 12 via sensing module 66, e.g., to determine when the carryover effects on the cortical activity from the stimulation delivered during the on cycle have dissipated to the point that the sensed cortical activity is within the threshold percentage of the baseline cortical activity.

When processor 80 determines that the brain state of patient 12 corresponds to cortical activity that is within a threshold percentage of the baseline value, then processor 80 may initiate the next on cycle of the therapy and control stimulation generator 66 to generate and deliver stimulation to brain 28 via one or more of electrodes 24, 26 (156).

The therapy delivered to brain 28 during the on cycle (156) may return the cortical activity to a desired level. In some examples, sensing module 66 may be configured to sense the brain signal of patient 12 during the on cycle as well as during the off cycle to allow processor 60 to evaluate the effect of the stimulation delivered to patient 12 on the cortical activity within brain 28. Processor 60 may monitor the cortical activity of patient 12 during the on cycle and select the on cycle duration, e.g., by determining when to end the delivery of stimulation, when the cortical activity of brain 28 is determined to be at a targeted level. In other examples, the length of the on cycle may be a preprogrammed duration, e.g., an on cycle duration determined by trialing a variety of on cycle as previously described.

In some examples, the on cycle duration may be a programmed value that processor 60 can adjust based on the effects on the monitored brain signal from the stimulation delivered during an on cycle. For example, if processor 60 determines that the sensed cortical activity of brain 28 did not reach a targeted level (e.g., associated with a target brain state) after delivery for stimulation for a set on cycle duration, processor 60 may select a new on cycle duration, e.g., by increasing or decreasing the on cycle duration. In some examples, processor 60 may adjust the on cycle duration only after identifying a predefined number of occurrences of not reaching a target level of cortical activity. Processor 60 may continue to adjust the on cycle duration until the selected on cycle duration achieves the target level of cortical activity from the delivered stimulation. In this manner, processor 60 may select both the on cycle duration and off cycle duration based on the sensed brain signal.

In some examples, if the stimulation delivered by IMD 16 does not produce a desired effect, such as, e.g., a degree of suppression of cortical activity or increase of cortical activity, IMD 16 may initiate therapy according to a default program, which may define cycled or substantially continuous stimulation. In some examples, the default program may define a therapy known to treat or manage the disorder of patient 12 to at least some extent, and may be appropriate when IMD 16 detects that the previously delivered cycled stimulation is not producing a desired effect. One or more default programs can be stored in IMD 16, programmer 14, or another suitable device. In other examples, processor 60 and/or processor 80 may select a new therapy program stored in memory 62 and/or 82, and deliver therapy to patient 12 with the new therapy program using the same or different therapy cycle parameters, e.g., the same or different on cycle/off cycle duration combination used for the previous therapy program.

Figure 22:
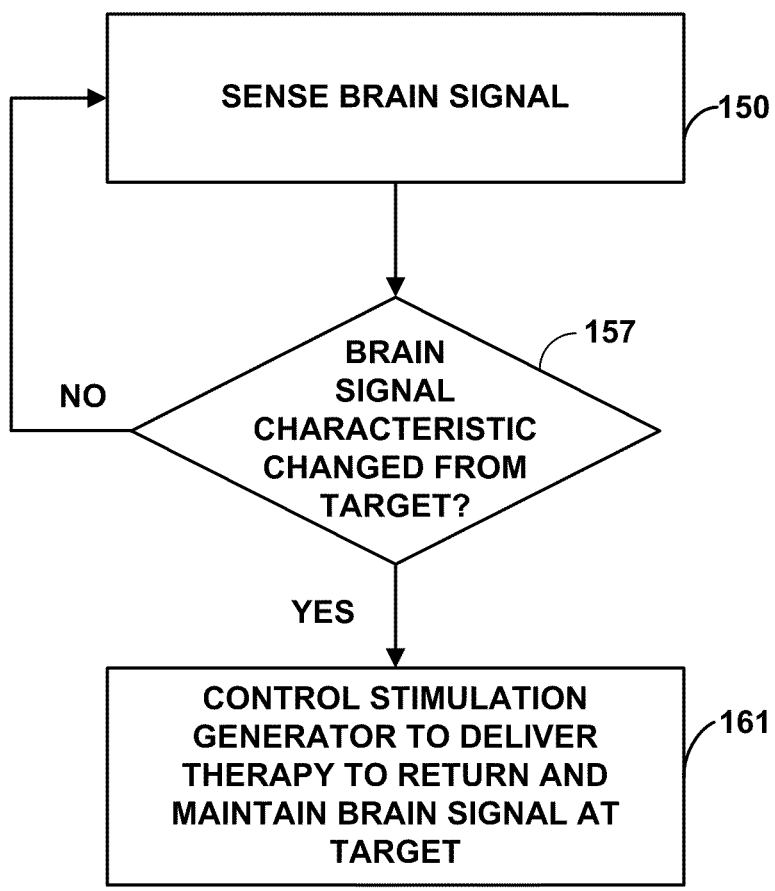
FIG. 22 is a flow diagram illustrating an example technique for controlling delivery of therapy to a patient.

FIG. 22 is a flow diagram illustrating an example technique for controlling delivery of therapy to a patient to maintain a target brain state. The example of FIG. 22 illustrates a technique for monitoring brain signals of brain 28 and delivering cycled stimulation from IMD 16 to brain 28 of patient 12 to maintain a target brain state. For ease of illustration, the target brain state is described in terms of a target level of cortical activity, where cortical activity is a characteristic (e.g., amplitude variation over time) derived from the sensed brain signal. However, any value of range of values of one or more other brain signal characteristics may be used as an indicator of the target brain state. The target brain state may be defined by one or more characteristics of a brain signal associated with effective treatment of a patient disorder.

As shown in FIG. 22, sensing module 66 of IMD 16 senses the brain signal of brain 28 via at least one of electrodes 24, 26 (150). Sensing module 66 may sense the brain signal of brain 28 prior to the delivery of therapy, during an off cycle of therapy delivered on a cycled basis, or any other suitable time period. Sensing module 66 may sense the brain signal at a time when the cortical activity of brain 28 is at a target level. The target level may be a cortical activity value or range of cortical activity values that defines a target brain state of patient 12.

Processor 60 analyzes the brain signal to determine whether the cortical activity of the sensed brain signal has changed from target cortical activity level (157). If the sensed brain signal indicates that the cortical activity of brain 28 is still at the target level, IMD 16 may continue to sense the brain signal of patient 12 using sensing module 66 (150) to monitor for changes to the cortical activity of brain 28.

If the sensed brain signal target indicates that the cortical activity has changed from the target level, processor 60 may control stimulation generator 64 to generate and deliver electrical stimulation to brain 28 of patient 12 to return and maintain the brain signal at the target level of cortical activity (161). For example, to return the cortical activity to the target level, processor 60 may initiate the delivery of therapy to patient 12 designed to change to cortical activity of brain 28 in the sensed region back to the target cortical activity level. In the case of cycled therapy, processor 60 may initiate an on cycle if the change from the target was detected during an off cycle of therapy. If the change from the target was detected during an on cycle of a therapy cycle, processor 60 may restart the on cycle, adjust one or more stimulation parameter values, or adjust the duration of the on cycle and/or off cycle. Once the brain signal returns to the target level of cortical activity, processor 60 may control delivery of therapy to patient 12 to maintain the brain signal at the target level. For example, processor 60 may control the delivery of therapy to patient 12 using one or more therapy cycle parameters selected to maintain the cortical activity at the target level.

Figure 23:
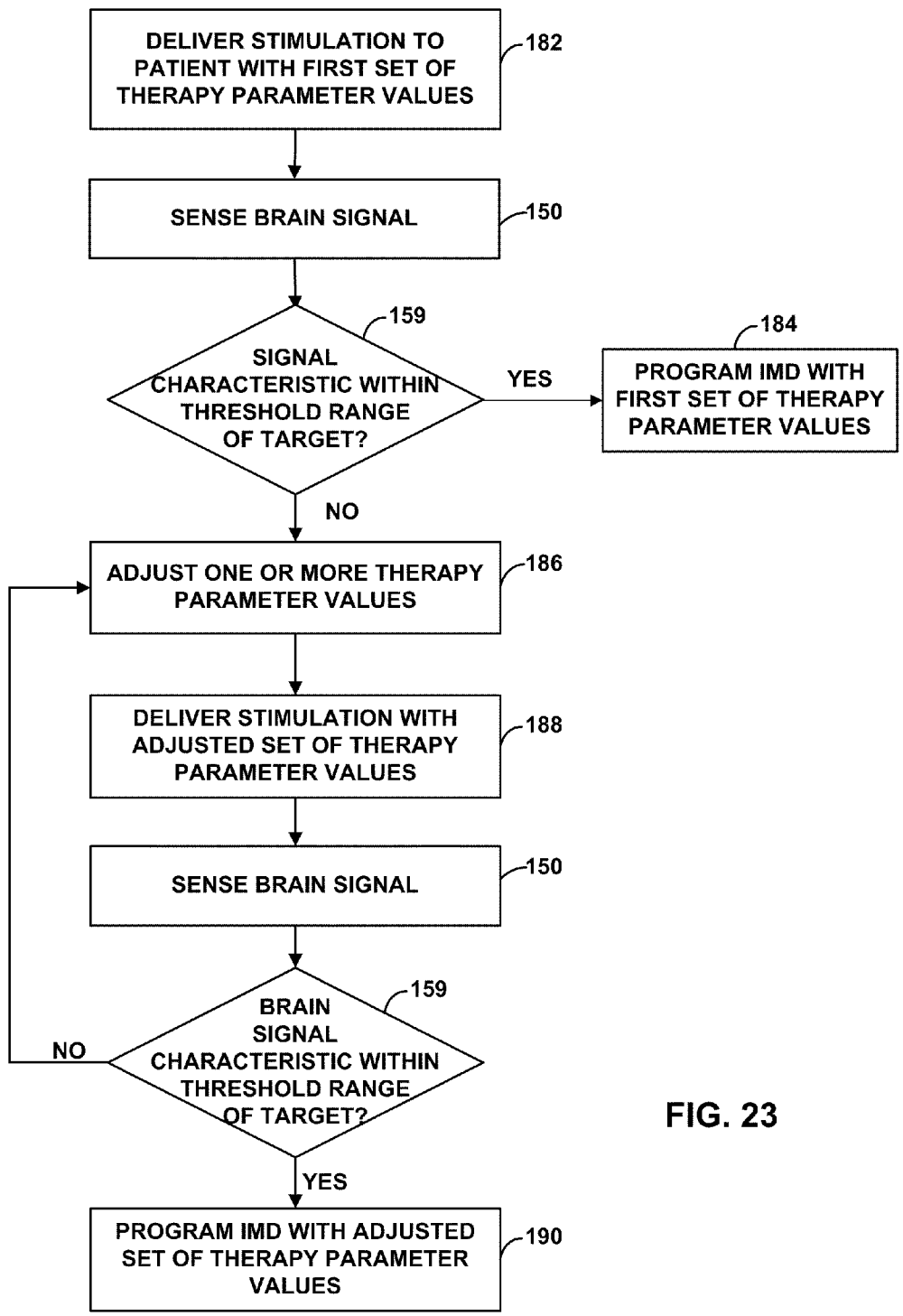
FIG. 23 is a flow diagram illustrating an example technique for programming one or more therapy parameters values of therapy program.

FIG. 23 is a flow diagram illustrating an example technique for programming one or more therapy parameters values of therapy program. In the example of FIG. 23, the stimulation parameter values defined by a therapy program may be selected such that the effect on brain 28 the delivery of stimulation according to the therapy results in a target brain state. The example technique of FIG. 23 may be used during a programming session to select suitable parameters values for one or more therapy programs. Alternatively or additionally, such a technique may be used to allow processor 60 to automatically or semi-automatically adjust one or more stimulation therapy parameters values defined by a therapy program during the delivery of chronic therapy to patient 12, e.g., if processor 60 determines that the effect of the stimulation according to a therapy program is not resulting in a target brain state when delivered to brain 28 of patient 12.

As shown in FIG. 23, processor 60 controls stimulation generator 66 to generate and deliver stimulation to brain 28 of patient 12 with a first set of therapy parameter values (182). For example, the first set of therapy parameter values may include stimulation parameter values for stimulation parameters, such as, e.g., frequency, amplitude (current or voltage), electrode configuration, and duty cycle. In the case of therapy including stimulation pulses, the therapy parameter values may include values for pulse width, pulse rate, pulse amplitude (current or voltage), and stimulation electrode configurations. Processor 60 may control the delivery of stimulation to patient 12 on a cycled basis. In such an example, stimulation generator 66 may deliver stimulation with the first set of therapy parameter values for at least one on cycle.

Sensing module 66 may sense the brain signal of patient 12 (150) to determine the effect of the stimulation delivered to patient 12 with the first set of therapy parameters. In some examples, processor 60 may evaluate one or more characteristics of the sensed brain signal, e.g., cortical activity, to determine the whether the brain signal characteristic is within a threshold range of a target value (159). The target value for the brain signal characteristic may define or otherwise be associated with a target brain state of patient 12 in which one or more symptoms of the patient condition or mitigated relative to a baseline state or in which the likelihood of an occurrence of a patient event is minimized relative to the baseline state. In some examples, the signal characteristic determined from the sensed signal may be presented to a user for evaluation by the user via programmer 14.

If the characteristic of the sensed brain signal is within a threshold range of the target value, a user may instruct processor 60 to program IMD 16 with the first set of therapy values (184). For example, a user may direct processor 60 via programmer 14 to define a first therapy program using the first set of therapy values. Processor 60 may store the first therapy program within memory 62 and may access the first therapy program in the future to control stimulation generator 66 to deliver therapy to patient 12 according to first therapy program.

If the characteristic of the sensed brain signal is not within the threshold range of the target value, a user may adjust one or more of therapy parameters values (186). For example, a user may instruct processor 60 via programmer 14 to increase or decrease the pulse rate value or another stimulation parameter value defined by the first set of therapy parameter values. For cycled therapy, a user may adjust the duration of the on cycle and/or off cycle. Any suitable methodology may be used to adjust one or more of therapy parameters. In some examples, a user may adjust the therapy parameter value(s) based on the observed effect that the first set of therapy parameters had on the signal characteristic. In other examples, a user may adjust the therapy parameters value(s) based on the effect of stimulation observed in one or more different patients being treated for the same or similar patient disorder.

Processor 60 may then control signal generator 64 to deliver stimulation to brain 28 according to the adjusted set of therapy parameter values (188). Sensing module 66 may sense the brain signal of patient 12 (150) to determine the effect of the stimulation delivered to patient 12 with the adjusted set of therapy parameters. If the characteristic of the sensed brain signal is within a threshold range of the target value, then a user may instruct processor 60 to program IMD 16 with the adjusted set of therapy values. For example, a user may direct processor 60 via programmer 14 to define a therapy program using the adjusted set of therapy values (190). Processor 60 may store the therapy program within memory 62 and may access the therapy program in the future to control stimulation generator 66 to deliver therapy to patient 12 according to adjusted set of therapy parameters.

If the characteristic of the sensed brain signal is not within the threshold range of the target value, a user may again adjust one or more of therapy parameters values (186), and sense the brain signal 150 after delivering therapy to brain 28 according to the adjusted set of parameters to determine whether or not the brain signal characteristic is within a threshold range of the target value.

Using the example technique of FIG. 23, a user may select therapy parameters that define a therapy that results a brain signal having characteristic value within a threshold range of a target value. The target value of the brain signal characteristic may define a brain state of patient 12 that is associated with effective treatment of the patient disorder. The examples technique may be repeated to define a plurality of suitable therapy programs each having a define set of therapy parameters that may be delivered to patient 12 to effectively treat a patient disorder.

FIG. 24 is a table 176 illustrating example metrics associated with therapy system 10. Processor 80 of programmer 14 (FIG. 4) may generate and present table 176 to a user, e.g., via user interface 86 (FIG. 4). The metrics presented in table 176 may relate to therapy configured to treat patient disorder by suppressing cortical activity in one or more regions of brain 28. In general, the type of metrics presented in table 176 may be modified based on the patient disorder treated by the therapy delivered to patient 12, in addition to the one or more effects that the delivered therapy has on patient 12.

In table 176, a plurality of therapy programs are listed in column 170. The level of cortical activity suppression resulting from delivered of stimulation to brain 28 of patient 12 according to a respective therapy program is listed in column 172. As described above, in some examples, a patient disorder, such as, e.g., a seizure disorder, may be effectively treated by suppressing cortical activity in one or more regions of brain 28. As such, the level of cortical activity suppression associated with each therapy program may be useful in evaluating the effectiveness of a therapy program.

The level of cortical activity suppression may be determined using any suitable methodology. In some examples, the level of cortical activity suppression may be determined based on the average level of cortical activity (e.g., as indicated by the variance in a brain signal or as indicated by a mean, median, peak, or instantaneous amplitude or frequency domain characteristic) during an off cycle compared to that of a baseline cortical activity level determined prior to the delivery of therapy to patient 12. In other examples, the level of cortical activity suppression may be calculated based on the maximum level of cortical activity suppression at any point in the therapy cycle compared to that of a baseline cortical activity level. In addition, a patient disorder such as Alzheimer's disease, e.g., may be effectively treated by enhancing cortical excitability in focal brain areas. As such, the level of cortical activity facilitation associated with each therapy program may also be useful in evaluating the effectiveness of a therapy program.

The washout period duration calculated for each therapy program in listed in column 174. The washout period duration for therapy delivered to a particular therapy program may be determined using any suitable technique. In some examples, the duration of a washout period for a particular therapy program may be determined using the example technique of FIG. 14. As the washout period duration may influence therapy cycle parameters, such as, off cycle duration, the washout period duration for each program may be useful in evaluating the effects of a therapy programs on the behavior of a brain signal.

The selected on cycle duration and off cycle duration for each program is listed in column 178 of table 176. The on cycle and off cycle duration listed in column 178 may be selected using one or more examples described herein. For example, one or more of the on cycle duration and off cycle duration may be selected based on the washout period determined for a therapy program. In some examples, at least one of the therapy cycle parameters may be selected such that the cycle therapy maintains a target brain state of patient 12, e.g., without returning to a baseline brain state. As the temporal effects on a brain signal from delivered therapy may vary depending on the stimulation parameters values defining the stimulation, the selected on cycle duration and off cycle duration may vary amongst therapy programs, as shown in the information listed in column 178 of table 176. Presenting the on cycle and off cycle durations for each program may allow a user to evaluate each of the therapy programs relative to one another.

The power usage rating for each therapy program is listed in column 180 of table 176. As described above, the power usage rating may reflect the power usage of therapy when delivered according to the particular therapy program for the selected therapy cycle parameter values. In examples in which IMD 16 is implanted within patient 12 for chronic therapy delivery, it may be desirable to minimize power consumption in order to extend the useful life of IMD 16 or minimize time between recharging of power source 36 (FIG. 2). As such, user may evaluate and compare the therapy programs listed in table 176 based on the power usage of each program reflected by the power usage rating shown in column 180.

In general, the information presented in table 176 may be useful for evaluating and comparing therapy programs based on the presented metrics. For example, a clinician may take such information into consideration when selecting a chronic therapy program for patient 12 or for generating additional therapy programs to trial on patient. In some examples, a user may be able to sort the therapy programs presented by programmer 14 according to a selected metric value. For example, upon a user selecting the power usage rating metric for sorting, processor 80 may reorganize the order of programs presented in table 176 from highest to lowest power usage rating value. In this manner, a user may easily identify the therapy programs with the most efficient power usage rating, and select those therapy programs for chronic delivery of therapy to patient 12 to treat a patient disorder.

FIG. 25 is a flow diagram illustrating an example technique for controlling delivery of therapy to a patient. According to the example technique shown in FIG. 25, processor 60 and/or processor 80 may monitor one or more evaluation metrics associated with the therapy delivered to patient to evaluate a therapy program being used to generate and deliver therapy to patient 12 to manage or treat a patient condition. In some examples, processor 60 and/or processor 80 may determine that a new therapy program should be used in place of the therapy program currently being used for the therapy being delivered to patient 12 based on the evaluation metric. Using such a technique, a therapy system such as therapy system 10 (FIG. 1) may maintain the delivery of chronic therapy to patient 12 to effectively manage or treat a patient condition over a period of time by periodically adjusting the therapy program used by processor 60 to control delivery of therapy to patient 12. For ease of description, the example technique of FIG. 25 is described with regard to therapy system 10 and processor 60 of IMD 16. However, such an example technique may be incorporated into any suitable therapy system for delivering therapy to patient 12 to manage one or more patient conditions, including, e.g., system 50 (FIG. 2) and may be implemented in whole or in part by another processor, such as processor 80 of programmer 14.

As shown in FIG. 25, processor 60 of IMD 16 may control the delivery of cycled therapy to patient 12 according to a selected therapy program for a selected on cycle/off cycle duration combination (182). The on cycle/off cycle duration may be selected using one or more of the techniques described herein to provide effective therapy to patient 12 (e.g., to reduce the frequency, duration or severity of one or more symptoms associated with the patient condition and/or reduce the frequency, duration or severity of stimulation-induced side effects). During the delivery of the therapy from IMD 16 to patient 12, one more evaluation metrics may be monitored by processor 60 and/or processor 80. Example evaluation metrics may include one or more of those metrics described above with regard to FIGS. 14, 15, and 24. For ease of description, the example of FIG. 25 is described with regard to the power usage rating. However, any suitable evaluation metric may be utilized.

As described above, the power usage rating may be considered an evaluation metric of the respective therapy cycle parameters, as well as therapy programs. A power usage rating may reflect a rating of the IMD 16 power usage when delivering therapy according to particular therapy program for given therapy cycle parameter value (e.g., on cycle and off cycle duration). The power usage for a given therapy program and on cycle/off cycle duration combination may be, for example, rated on a numerical scale, where the lower power consumption therapy programs are provided with a higher power usage rating. For example, the power usage rating may be a numerical rating on a scale from 1 to 10, where a rating of "10" indicates a lower power usage (e.g., more power efficient) than a rating of "1." However, other types of scales are possible, and are not limited to a numerical scale or a numerical 1-10 scale.

As processor 60 and/or processor 80 may automatically and/or semi-automatically adjust the therapy cycle parameters, e.g., using one or more of the example techniques described herein, during the delivery of chronic therapy to patient 12, the power usage rating (or other evaluation metric) for a particular therapy program may change over time. Such changes may or may not be desirable, e.g., with regard to the power usage of the therapy delivered to patient by IMD 16. For example, in the case of adjustment that increases the on cycle duration and/or decreases the off cycle duration for a particular therapy program, the power usage of IMD 16 may increase beyond that provided when the therapy program was originally selected for therapy. In such cases, if may be desirable to adjust the therapy program used for therapy delivery to a different therapy program that requires less power usage to manage the patient condition.

In the example of FIG. 25, processor 60 monitors the power usage rating of the therapy being delivered to patient 12 to determine whether or not the power usage rating is greater than a predetermined threshold value (184). The threshold value may be a preprogrammed value that generally reflects some minimum power efficacy (or maximum power usage) desired for the therapy being delivered to patient 12 to manage the patient condition. For purposes of illustration, as described above, a power usage rating may be expressed on a numerical scale, where the higher the numerical value reflects lower power usage (e.g., more power efficient). In such a case, if processor 60 determines that the power usage rating is greater than the threshold value for the selected therapy program and on cycle/off cycle duration combination (184), processor 60 may continue controlling the therapy to patient 12 according the selected program and selected on cycle/off cycle duration combination (182). Conversely, if processor 60 determines that the power usage rating is not greater than the threshold value for the selected therapy program and on cycle/off cycle duration combination (184), processor 60 may discontinue the use of the present therapy program and select a new therapy program for therapy delivery (186).

In some examples, processor 60 may discontinue use of a therapy program and select a new program after the first occurrence of the power usage not being greater than the threshold value. Alternatively, processor 60 and/or processor 80 may discontinue use of a therapy program and select a new program only after multiple occurrences of the power usage not being greater than the threshold value. For example, processor 60 may store occurrences of such a condition within memory 62 and discontinue the use of the current therapy program and select a new therapy program once the number of occurrences has reached a predefined value. After processor 60 determines that the power usage rating is not greater than a threshold value, e.g., during a particular time period, processor 60 may increment a counter.

Processor 60 may determine whether the number of occurrences of the power usage rating not being greater than the threshold value is greater than or equal to a predetermined number. The predetermined number may be stored within memory 82 of programmer 14 or a memory of another device, and may indicate the threshold number of times the power usage rating may not be greater than the threshold value before determining that a particular therapy program or program group is not power efficient. The predetermined number may be determined by a clinician, e.g., based on past patient data or based on clinician knowledge. For example, the clinician may determine that if the power usage rating associated with a particular therapy program or group was not greater than the threshold value at least ten times within a particular time range, the therapy program or group is relatively power inefficient and a therapy adjustment may be desirable.

If the number of times the power usage rating associated with a particular therapy program or group was not greater than the threshold value, processor 60 may control the adjustment of therapy. In the example shown in FIG. 25, therapy to patient 12 may be adjusted by, for example, switching therapy programs or therapy program groups, adjusting one or more therapy parameter values, or adjusting therapy cycle parameters (186).

Processor 60 (and/or processor 80) may select a different therapy program according to instructions stored in memory 62 and/or memory 82 (186). In some examples, if information regarding available therapy programs relative to one or more evaluation metrics is available (e.g., based on some prior evaluation of therapy programs such as that shown in the examples of FIGS. 19 and 24), processor 60 may select the different therapy program based on the evaluation metrics. For example, processor 60 and/or processor 80 may select the therapy program with the highest power usage rating that is different than the therapy program that is being discontinued. In other examples, processor 60 and/or processor 80 may trial existing therapy programs until a therapy program that meets the desired power usage criteria in found. For a selected therapy program, the on cycle/off cycle duration for the therapy may be predefined or selected after the therapy program is selected to replace an existing therapy program (186). In some examples, one or more on cycle/off cycle durations may be selected for the therapy program using one or more techniques described herein.

If processor 60 and/or processor 80 is unable to identify a therapy program and on cycle/off cycle duration combination that meets the desired criteria (power usage rating in the example of FIG. 25), processor 60 and/or processor 80 may control therapy according to the therapy program and on cycle/off cycle duration combination associated with the greatest power usage rating (least amount of power usage). In other examples, processor 60 and/or processor 80 may control the delivery of therapy to patient 12 according to some default therapy program which may or may not be delivered on a cyclic basis. In some examples, processor 60 and/or processor 80 may control the delivery of therapy to patient 12 according to the original therapy program that was found to not satisfy the power usage rating threshold (184).

In other examples of the technique shown in FIG. 25, processor 60 may use multiple evaluation metrics rather than a single evaluation metric to determine when to discontinue use of a therapy program and select a different program. Power usage is only one example of an evaluation metric that may be employed by therapy system 10 to periodically change the therapy program used to deliver therapy to patient 12. In general, the evaluation metric used in the example of FIG. 25 may be a gauge of power usage, therapeutic efficacy, or other variable that is suitable for determining when a new therapy program should be selected.

In addition to, or as an alternative to, power usage rating, evaluation metrics such as cortical actively suppression, washout period duration, on cycle duration, and/or off cycle duration may be used to determine when to change the therapy program used by processor 60 to control the therapy delivered to patient 12. For example, processor 60 and/or processor 80 may discontinue a therapy program and select a new therapy program if the off cycle and/or off cycle duration for the present therapy program is greater than a maximum duration. Similarly, processor 60 and/or processor 80 may discontinue a therapy program and select a new therapy program if the on cycle duration and/or washout period duration for the present therapy program is less than a minimum duration. In some examples, processor 60 and/or processor 80 may discontinue a therapy program and select a new therapy program if the cortical activity suppression provided by the present therapy program is less than a minimum percent value of suppression relative to a baseline level of cortical activity. Evaluation metrics other than those described above are contemplated.

Figure 26:
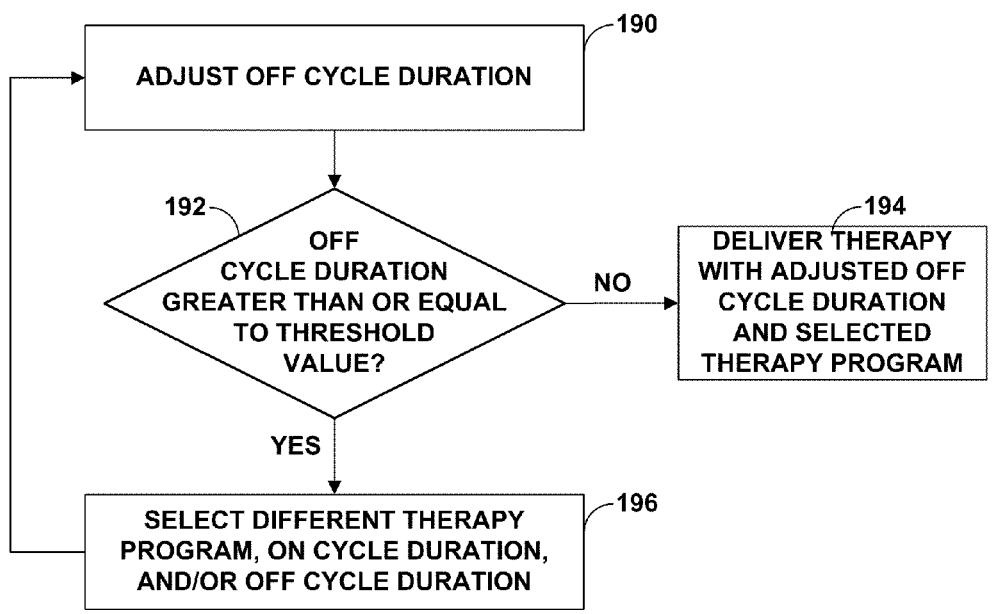

FIG. 26 is a flow diagram of an example technique that processor 60 of IMD 16, processor 80 of programmer 14 or a processor of another device may implement to control therapy delivery by IMD 16. FIG. 26 is described with respect to processor 60 of IMD 16. However, in other examples, processor 80 of programmer 14 or a processor of another device may implement any part of the technique shown in FIG. 26.

As discussed above, e.g., with respect to FIGS. 14, 15, and 17, processor 60 of IMD 16 may adjust an off cycle duration with which stimulation generator 64 delivers electrical stimulation to a target tissue site of patient 12. For example, as discussed with respect to FIG. 15, for a selected therapy program and a selected on cycle duration, processor 60 may select an off cycle duration that is less than that the duration of the washout period determined for the selected therapy program and the selected on cycle duration. Other techniques for adjusting an off cycle duration are also contemplated.

In accordance with the technique shown in FIG. 26, after adjusting the off cycle duration for a selected therapy program using the techniques described above or any other suitable technique (190), processor 60 determines whether the off cycle duration is greater than or equal to a threshold value (192). The threshold value may be stored by memory 62 of IMD 16, memory 82 of programmer 14 or a memory of another device. In some examples, a clinician may select the threshold value to indicate the maximum off cycle duration that may be implemented to control therapy delivery without adversely affecting the efficacy of therapy delivery. For example, in the case of a seizure disorder, the threshold value may indicate the maximum off cycle duration at which seizures of patient 12 are substantially suppressed or minimized (e.g., the frequency, duration, and/or severity are minimized). In the case of Alzheimer's disease, the maximum off cycle duration at which the symptoms of Alzheimer's are substantially suppressed or mitigated.

If processor 60 determines that the off cycle duration is not greater than or equal to the threshold value, processor 60 may control stimulation generator 64 to deliver therapy to patient 12 via the adjusted off cycle duration and the selected therapy program (194). On the other hand, if processor 60 determines that the off cycle duration is greater than or equal to the threshold value, processor 60 may adjust therapy so as to adjust the off cycle duration. In the example shown in FIG. 26, processor 60 selects a different therapy program, e.g., using the techniques described above with respect to FIG. 25, determines a new on cycle duration or determines a new off cycle duration. In examples in which processor 60 determines a new on cycle duration, processor 60 may determine a new on cycle duration for the selected therapy program or for a different therapy program. By increasing or otherwise adjusting the on cycle duration, the corresponding off cycle duration may be affected. In examples in which processor 60 determines a new off cycle duration, processor 60 may determine the off cycle to be used with the selected therapy program or with a different therapy program that has been selected. In examples in which processor 60 determines the off cycle to be used with the selected therapy program, processor 60 may merely decrease the off cycle duration to a value less than or equal to the threshold value.

In some examples, processor 60 of IMD 16, processor 80 of programmer 14 or a processor of another device may implement a technique similar to that shown in FIG. 26 to determine whether an on cycle duration is suitable for providing efficacious therapy patient 12. However, rather than determining if the on cycle duration is greater than or equal to a threshold value, processor 60 may determine if the on cycle duration is less than or equal to a threshold value that indicates a minimum on cycle duration that may be implemented to control therapy delivery without adversely affecting the efficacy of therapy delivery. For example, a certain minimum amount of therapy may be delivered to patient 12 to achieve certain efficacious results. In such a technique, if processor 60 determines that the on cycle duration is less than or equal to a threshold value, processor 60 may adjust at least one of a therapy program, the on cycle duration or the off cycle duration. On the other hand, if processor 60 determines that the on cycle duration is greater than the threshold value, processor 60 may deliver therapy to patient 12 according to the selected therapy program and the on cycle duration selected for the therapy program.

Although some examples of the disclosure include delivering therapy to the brain of a patient and monitoring brain signals of a patient to select therapy parameters that may include cycled therapy parameters, examples are not limited to only the selection of cycled therapy parameters based on monitored brain signals. A therapy system, such as, e.g., system 10 (FIG. 1) may be configured to monitor brain signals of a patient in conjunction with the delivery of therapy to patient to evaluate the effects of the therapy on the brain signals of patient 12. Such example techniques may be utilized for programming of non cycled therapy program parameters and/or during delivery of chronic non-cycled therapy to select one or more therapy parameters, such as, e.g., pulse width, pulse amplitude, pulse rate, and/or stimulation electrode configuration (e.g., selection of one or more electrodes with which stimulation therapy is delivered and the respective polarity of the selected electrodes). In some cases, the influence that delivery of non-cycled therapy has on a brain signal of the patient may be monitored to evaluate the efficacy of the therapy parameter values of the delivered therapy (e.g., efficacy can include the mitigation of patient symptoms or patient events and, in some cases, the efficacy balanced with side effects). For example, non-cycled therapy may be delivered to a patient according to a therapy program, and the influence on the brain signal from the therapy (e.g., change in cortical activity) may be analyzed to determine whether or not the therapy program had the desired effect on the brain signal of a patient. Such a technique may be used to evaluate different therapy programs. In some examples, specific stimulation parameters may be analyzed based on the effect of therapy according to a selected value has the brain signal of a patient.

In some examples, therapy parameters may be adjusted, e.g., automatically or semi-automatically, by the medical device based on the behavior of the brain signal sensed during the non-cycled therapy. For example, if during chronic stimulation therapy it is determined that the patient's cortical activity level is approaching a baseline brain state or has reverted to a baseline brain state for a sustained period of time, indicating ineffective treatment, the device may automatically switch to another therapy program. Examples of automatic switching of therapy programs based on seizure occurrence are described in U.S. Patent Publication No. 2009/0082641 by Giftakis et al., entitled "PATIENT EVENT INDICATION" and filed on Sep. 23, 2008, which is hereby incorporated by reference in its entirety. In addition to or instead of automatically switching therapy programs based on patient input indicating the occurrence of a patient event (e.g., a seizure onset), as described in U.S. Patent Publication No. 2009/0082641, IMD 16 or another device can automatically switch therapy programs based on the number of patient events detected based on the patient's cortical activity level (e.g., as indicated by the bioelectrical brain signals and predetermined threshold values or ranges of signal characteristics associated with the patient events). Such adjustments may be intended to modulate the cortical activity, which may dynamically change with progression or improvement of the patient's condition. This is analogous to changing dosage levels of a prescription drug when the severity of the patient's condition changes. During the non-cycled therapy, the device may also temporarily suspend delivery of stimulation at periodic intervals, for the purpose of assessing stimulation effects on cortical activity in the absence of the prescribed therapy.

The techniques described in this disclosure, including those attributed to programmer 14, IMD 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 60 of IMD 16 and/or processor 80 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

In one aspect, the disclosure relates to a system comprising means for monitoring a brain signal of a patient, means for selecting at least one parameter of a therapy cycle on the monitored brain signal of the patient, and means for controlling delivery of the therapy to the patient according to the at least one selected parameter of the therapy cycle, wherein the at least one parameter of the therapy cycle includes at least one of an on cycle duration or an off cycle duration.

In one example system, the means for monitoring the brain signal of the patient comprises means for monitoring the brain signal of the patient during an off cycle of the therapy, the means for selecting the at least one parameter of the therapy cycle based on the brain signal of the patient comprises means for comparing the monitored brain signal of the patient during the off cycle to a baseline brain signal; and means for automatically adjusting at least one of the off cycle duration or the on cycle duration based on the comparison of the monitored brain signal of the patient to the baseline brain signal. In one example, the means for comparing the monitored brain signal of the patient during the off cycle of the therapy to the baseline brain signal comprises means for determining whether a characteristic of the monitored brain signal is within a threshold range of the baseline brain signal.

In one example, such a system further comprises means for controlling delivery of the therapy to the patient according to a first therapy program for a first on cycle duration, wherein the means for monitoring the brain signal of the patient comprises means for monitoring the brain signal of the patient following the first on cycle duration; and means for determining a washout period for the therapy based on the monitored brain signal of the patient following the first on cycle duration, wherein the means for selecting at least one parameter of the therapy cycle based on the monitored brain signal of the patient comprises means for selecting at least one parameter of the therapy cycle based on the washout period determined for the therapy.

In one example, such a system further comprises means for controlling delivery of therapy according to a plurality of therapy programs, wherein the means for monitoring the brain signal of the patient comprises means for monitoring the brain signal after delivery of therapy for each of the therapy programs; and means for determining a washout period for each of the therapy programs based on the monitored brain signal, wherein the means for selecting at least one parameter of the therapy cycle based on the monitored brain signal of the patient comprises means for selecting the at least one parameter of the therapy cycle for each therapy program based on the washout period for the respective therapy program.

In one example, such a system further comprises means for controlling delivery of therapy to the patient according to a first therapy program defining at least one therapy parameter value during at least one on cycle, wherein the means monitoring the brain signal of the patient comprises means for monitoring the brain signal of the patient following the delivery of therapy during the at least one on cycle; and means for adjusting the at least one therapy parameter value defined by the therapy program based on the monitored brain signal.

In one example system, the means for controlling delivery of the therapy to the patient comprises means for controlling delivery of therapy to a first location within a brain of the patient that is different from a second location within the brain in which the means for monitoring monitors the brain signal.

In one example system, the means for monitoring the brain signal of a patient comprises means for monitoring at least one of an electroencephalogram (EEG) signal, an electrocorticogram (ECoG) signal, a local field potential (LFP) sensed from within one or more regions of a brain of the patient or an action potential signal from the brain of the patient.

In one example system, the means for controlling delivery of therapy comprises means for controlling delivery of therapy to at least one of an anterior thalamic nucleus, internal capsule, cingulate, formix, mammillary bodies, mammillothalamic tract, subgenual component of the cingulate cortex, cortex, vagal nerve, or hippocampus of the patient.

In one example system, the means for monitoring the brain signal of the patient comprises means for monitoring the brain signal within one of an anterior thalamic nucleus or hippocampus of a brain of the patient, and the means for controlling delivery of the therapy to the patient comprises means for controlling therapy delivery to the other of the anterior thalamic nucleus or hippocampus of the brain of the patient.

In one example system, the means for monitoring the brain signal of the patient comprises means for monitoring the brain signal within one of an anterior thalamic nucleus or hippocampus of a brain of the patient and the means for controlling delivery of the therapy to the patient comprises means for controlling therapy delivery to the same of the anterior thalamic nucleus or hippocampus of the brain of the patient.

In one example system, the means for selecting the at least one parameter of the therapy cycle comprises means for selecting a first on cycle; means for delivering therapy to the patient according to the first on cycle; means for selecting a first off cycle based on the delivery of stimulation according to the first on cycle; means for selecting a second on cycle; means for delivering therapy to the patient according to the second on cycle; means for selecting a second off cycle based on the delivery of stimulation according to the second on cycle; and means for selecting a first combination comprising the first on cycle and the first off cycle or a second combination comprising the second on cycle and the second off cycle.

In one example system, the means for selecting the at least one parameter of the therapy cycle comprises means for selecting a plurality of on cycles; means for delivering therapy to the patient according to each on cycle of the plurality of on cycles; means for selecting respective off cycles for each on cycle of the plurality of on cycles based on the delivery of stimulation according to each on cycle of the plurality of on cycles; and means for selecting at least one of the on cycles of the plurality of on cycles and the respective off cycle as the at least one parameter of the therapy cycle.

In one example system, the means for selecting the at least one parameter of the therapy cycle comprises means for selecting an on cycle; means for delivering therapy to the patient according to the on cycle and each of a plurality of off cycles; and means for selecting the on cycle and at least one off cycle of the plurality of off cycles as the at least one parameter of the therapy cycle based on the delivery of therapy to the patient according to the on cycle and each of a plurality of off cycles.

Various examples have been described. These and other examples are within the scope of the following claims.

The invention claimed is:

1. A method comprising:
monitoring a brain signal of a patient;
determining a brain state of the patient based on the monitored brain signal;
comparing the determined brain state of the patient to a baseline brain state;
selecting at least one of an on cycle duration or an off cycle duration of a therapy cycle based on the comparison; and
controlling delivery of therapy to the patient according to the at least one selected parameter of the therapy cycle, wherein selecting the at least one of the on cycle duration or the off cycle duration of the therapy cycle based on the comparison comprises selecting the at least one of the on cycle duration or the off cycle duration such that the delivery of therapy maintains the brain signal of the patient within a threshold degree of the baseline brain state.

2. The method of claim 1, wherein monitoring the brain signal of the patient comprises monitoring the brain signal of the patient during an off cycle of the therapy, and wherein determining the brain state comprises determining the brain state of the patient based on the brain signal monitored during the off cycle of the therapy.

3. The method of claim 1, wherein comparing the determined brain state of the patient to the baseline brain state comprises determining whether a characteristic of the determined brain state is within the threshold degree of the baseline brain state.

4. The method of claim 1, further comprising controlling delivery of the therapy to the patient according to a first therapy program for a first on cycle duration, wherein monitoring the brain signal of the patient comprises monitoring the brain signal of the patient following the first on cycle duration, wherein comparing the determined brain state of the patient to the baseline brain state comprises determining a washout period for the therapy based on the monitored brain signal following the first on cycle duration, and wherein selecting the at least one of the on cycle duration or the off cycle duration of the therapy cycle based on the comparison comprises selecting the at least one parameter of the therapy cycle based on the washout period determined for the therapy.

5. The method of claim 1, further comprising
controlling delivery of therapy according to a plurality of therapy programs, wherein monitoring the brain signal of the patient comprises monitoring the brain signal after delivery of therapy according to each therapy program of the plurality of therapy programs, wherein comparing the determined brain state of the patient to the baseline brain state comprises determining a washout period for each therapy program of the plurality of therapy programs based on the respective monitored brain signal, and wherein selecting the at least one of the on cycle duration or the off cycle duration of the therapy cycle based on the comparison comprises selecting the at least one parameter of the therapy cycle for each therapy program of the plurality of therapy programs based on the washout period determined for the respective therapy program.

6. The method of claim 1, further comprising:
controlling delivery of therapy to the patient according to a first therapy program defining at least one therapy parameter value during at least one on cycle, wherein monitoring the brain signal of the patient comprises monitoring the brain signal of the patient following the delivery of therapy during the at least one on cycle; and
adjusting the at least one therapy parameter value defined by the therapy program based on the comparison of the determined brain state to the baseline brain state.

7. The method of claim 1, wherein therapy is delivered to the patient at a first location within a brain of the patient that is different from a second location within the brain in which the brain signal is monitored.

8. The method of claim 1, wherein monitoring the brain signal comprises monitoring at least one of an electroencephalogram (EEG) signal, an electrocorticogram (ECoG) signal, a local field potential (LFP) sensed from within one or more regions of a brain of the patient or an action potential signal from the brain of the patient.

9. The method of claim 1, wherein the therapy is delivered to at least one of an anterior thalamic nucleus, internal capsule, cingulate, fornix, mammillary bodies, mammillothalamic tract, subgenual component of the cingulate cortex, cortex, vagal nerve, or hippocampus of the patient.

10. The method of claim 1, wherein monitoring the brain signal of the patient comprises monitoring the brain signal within one of an anterior thalamic nucleus or hippocampus of a brain of the patient and controlling delivery of the therapy to the patient comprises controlling therapy delivery to the other of the anterior thalamic nucleus or hippocampus of the brain of the patient.

11. The method of claim 1, wherein monitoring the brain signal of the patient comprises monitoring the brain signal within one of an anterior thalamic nucleus or hippocampus of a brain of the patient and controlling delivery of the therapy to the patient comprises controlling therapy delivery to the same of the anterior thalamic nucleus or hippocampus of the brain of the patient.

12. The method of claim 1, wherein selecting the at least one of the on cycle duration or the off cycle duration of the therapy cycle comprises:
selecting a first on cycle;
controlling delivery of therapy to the patient according to the first on cycle;
selecting a first off cycle based on the delivery of therapy according to the first on cycle;
selecting a second on cycle;
controlling delivery of therapy to the patient according to the second on cycle;
selecting a second off cycle based on the delivery of therapy according to the second on cycle; and
selecting a first combination comprising the first on cycle and the first off cycle or a second combination comprising the second on cycle and the second off cycle.

13. The method of claim 1, wherein selecting the at least one of the on cycle duration or the off cycle duration of the therapy cycle comprises:
selecting a plurality of on cycles;
controlling delivery of therapy to the patient according to each on cycle of the plurality of on cycles;
selecting respective off cycles for each on cycle of the plurality of on cycles based on the delivery of therapy according to each on cycle of the plurality of on cycles; and
selecting at least one of the on cycles of the plurality of on cycles and the respective off cycle as the at least one parameter of the therapy cycle.

14. The method of claim 1, wherein selecting the at least one of the on cycle duration or the off cycle duration of the therapy cycle comprises:
selecting an on cycle;
controlling delivery of therapy to the patient according to the on cycle and each of a plurality of off cycles; and
selecting the on cycle and at least one off cycle of the plurality of off cycles as the at least one parameter of the therapy cycle based on the delivery of therapy to the patient according to the on cycle and each of a plurality of off cycles.

15. The method of claim 1, further comprising periodically adjusting the at least one selected parameter of the therapy cycle based at least in part on the brain signal monitored following the selection of the at least one parameter.

16. The method of claim 1, wherein selecting the at least one of the on cycle duration or the off cycle duration such that the delivery of therapy maintains the brain signal of the patient within the threshold degree of the baseline brain state comprises selecting the at least one of the on cycle duration or the off cycle duration such that the delivery of therapy prevents the brain state of the patient from returning to the baseline brain state.

17. The method of claim 1, wherein selecting the at least one of the on cycle duration or the off cycle duration such that the delivery of therapy maintains the brain signal of the patient within the threshold degree of the baseline brain state comprises selecting the at least one of the on cycle duration or the off cycle duration such that the delivery of therapy maintains the brain state of the patient at an activity level below the baseline brain state.

18. A system comprising:
a sensing module configured to monitor a brain signal within a brain of a patient;
a therapy module configured to delivery therapy to the patient; and
a processor configured to determine a brain state of the patient based on the monitored brain signal and to compare the determined brain state of the patient to a baseline brain state, and further configured to select at least one of an on cycle duration or an off cycle duration of a therapy cycle based on the comparison, and control the therapy module to deliver the therapy to the patient according to the at least one selected parameter of the therapy cycle, wherein the processor is configured to select the at least one of the on cycle duration or the off cycle duration such that the delivery of therapy maintains the brain signal of the patient within a threshold degree of the baseline brain state.

19. The system of claim 18, wherein the sensing module is configured to monitor the brain signal of the patient during an off cycle of the therapy, and wherein the processor is configured to determine the brain state based on the brain signal monitored during the off cycle of the therapy.

20. The system of claim 18, wherein the processor is configured to determine whether a characteristic of the determined brain state is within the threshold degree of the baseline brain state.

21. The system of claim 18, wherein the processor is configured to control delivery of the therapy to the patient according to a first therapy program for a first on cycle duration, wherein the sensing module is configured to monitor the brain signal of the patient following the first on cycle duration, and the processor is configured to determine a washout period for the therapy according to the first therapy program based on the brain signal monitored following the first on cycle duration, and select the at least one of the on cycle duration or the off cycle duration of the therapy cycle based on the washout period determined for the therapy according to the first therapy program.

22. The system of claim 18, wherein the processor is configured to control delivery of therapy according to a plurality of therapy programs, wherein the sensing module is configured to monitor the brain signal after delivery of therapy according to each therapy program of the plurality of therapy programs, and the processor is configured to determine a washout period for each therapy program of the plurality of therapy programs based on the respective monitored brain signal, and select the at least one of the on cycle duration or the off cycle duration of the therapy cycle for each therapy program based on the washout period determined for respective therapy programs.

23. The system of claim 18, wherein the processor is configured to monitor the brain signal of the patient following the delivery of therapy during the at least one on cycle and adjust the at least one therapy parameter value defined by the therapy program based on the comparison of the determined brain state to the baseline brain state.

24. The system of claim 18, wherein the therapy module is configured to deliver the therapy to the patient at a first location within a brain of the patient that is different from a second location within the brain in which the brain signal is monitored by the sensing module.

25. The system of claim 18, wherein the sensing module is configured to monitor the brain signal by at least monitoring at least one of an electroencephalogram (EEG) signal, an electrocorticogram (ECoG) signal, a local field potential (LFP) sensed from within one or more regions of a brain of the patient or an action potential signal from the brain of the patient.

26. The system of claim 18, wherein the therapy module is configured to deliver the therapy to at least one of an anterior thalamic nucleus, internal capsule, cingulate, fornix, the mammillary bodies, the mammillothalamic tract, subgenual component of the cingulate cortex, cortex, vagal nerve, or hippocampus of the patient.

27. The system of claim 18, wherein the sensing module is configured to monitor the brain signal of the patient within one of an anterior thalamic nucleus or hippocampus of a brain of the patient, and the processor is configured to control the therapy module to deliver the therapy to the other of the anterior thalamic nucleus or hippocampus of the brain of the patient.

28. The system of claim 18, wherein the sensing module is configured to monitor the brain signal of the patient within one of an anterior thalamic nucleus or hippocampus of a brain of the patient, and the processor is configured to control the therapy module to deliver the therapy to the same of the anterior thalamic nucleus or hippocampus of the brain of the patient.

29. The system of claim 18, wherein the processor is configured to:
select a first on cycle;
control the therapy module to deliver therapy to the patient according to the first on cycle;
select a first off cycle based on the delivery of therapy according to the first on cycle;
select a second on cycle;
control the therapy module to deliver therapy to the patient according to the second on cycle;
select a second off cycle based on the delivery of therapy according to the second on cycle; and
select a first combination comprising the first on cycle and the first off cycle or a second combination comprising the second on cycle and the second off cycle.

30. The system of claim 18, wherein the processor is configured to select a plurality of on cycles;
control the therapy module to deliver therapy to the patient according to each on cycle of the plurality of on cycles;
select respective off cycles for each on cycle of the plurality of on cycles based on the delivery of therapy according to each on cycle of the plurality of on cycles; and
select at least one of the on cycles of the plurality of on cycles and the respective off cycle as the at least one parameter of the therapy cycle.

31. The system of claim 18, wherein the processor is configured to:
select an on cycle;
control the therapy module to deliver therapy to the patient according to the on cycle and each of a plurality of off cycles; and
select the on cycle and at least one off cycle of the plurality of off cycles as the at least one parameter of the therapy cycle based on the delivery of therapy to the patient according to the on cycle and each of a plurality of off cycles.

32. The system of claim 18, wherein the processor is configured to periodically adjust the at least one selected parameter of the therapy cycle based at least in part on the brain signal monitored following the selection of the at least one parameter.

33. The system of claim 18, wherein the processor is configured to select the at least one of the on cycle duration or the off cycle duration such that the delivery of therapy prevents the brain state of the patient from returning to the baseline brain state.

34. The system of claim 18, wherein the processor is configured to select the at least one of the on cycle duration or the off cycle duration such that the delivery of therapy maintains the brain state of the patient at an activity level below the baseline brain state.

35. A system comprising:
means for monitoring a brain signal of a patient;
means for determining a brain state of the patient based on the monitored brain signal;
means for comparing the determined brain state of the patient to a baseline brain state;
means for selecting at least one of an on cycle duration or an off cycle duration of a therapy cycle based on the comparison; and
means for controlling delivery of the therapy to the patient according to the at least one selected parameter of the therapy cycle,
wherein the means for selecting the at least one of the on cycle duration or the off cycle duration of the therapy cycle based on the comparison comprises means for selecting the at least one of the on cycle duration or the off cycle duration such that the delivery of therapy maintains the brain signal of the patient within a threshold degree of the baseline brain state.

36. A non-transitory computer-readable storage medium comprising instructions that cause a programmable processor to:
monitor a brain signal of a patient;

determine a brain state of the patient based on the monitored brain signal;

compare the monitored brain state of the patient to a baseline brain state;

select at least one of an on cycle duration or an off cycle duration of a therapy cycle based on the determined brain state; and control delivery of therapy to the patient according to the at least one selected parameter of the therapy cycle, wherein the at least one of an on cycle duration or an off cycle duration is selected such that the delivery of therapy maintains the brain signal of the patient within a threshold degree of the baseline brain state.

* * * * *